US010766873B2

(12) United States Patent
Bourdoulous et al.

(10) Patent No.: US 10,766,873 B2
(45) Date of Patent: Sep. 8, 2020

(54) ZUCLOPENTHIXOL HYDROCHLORIDE DERIVATIVES AND EBSELEN DERIVATIVES AS ERBB2 INHIBITORS

(71) Applicants: Centre National de la Recherche Scientifique (CNRS), Paris (FR); Institut National de la Sante et de la Recherche Medicale (INSERM), Paris (FR); Universite Paris Descartes, Paris (FR)

(72) Inventors: Sandrine Bourdoulous, Gagny (FR); Camille Faure, Paris (FR)

(73) Assignees: Centre National de la Recherche Scientifique (CNRS) (FR); Institut National de la Sante et de la Recherche Medicale (INSERM) (FR); Universite Paris Descartes (FR)

( * ) Notice: Subject to any disclaimer, the term of this patent is extended or adjusted under 35 U.S.C. 154(b) by 0 days.

(21) Appl. No.: 16/069,049

(22) PCT Filed: Jan. 11, 2017

(86) PCT No.: PCT/EP2017/050471
§ 371 (c)(1),
(2) Date: Jul. 10, 2018

(87) PCT Pub. No.: WO2017/121755
PCT Pub. Date: Jul. 20, 2017

(65) Prior Publication Data
US 2019/0031639 A1  Jan. 31, 2019

(30) Foreign Application Priority Data
Jan. 11, 2016  (EP) ..................... 16305019

(51) Int. Cl.
| *C07D 335/20* | (2006.01) |
| *A61K 31/41* | (2006.01) |
| *A61K 31/497* | (2006.01) |
| *A61P 35/00* | (2006.01) |
| *C07D 275/04* | (2006.01) |
| *C07D 279/24* | (2006.01) |
| *C07D 293/12* | (2006.01) |
| *C07D 405/06* | (2006.01) |
| *C07D 409/06* | (2006.01) |

(52) U.S. Cl.
CPC ............ *C07D 335/20* (2013.01); *A61K 31/41* (2013.01); *A61K 31/497* (2013.01); *A61P 35/00* (2018.01); *C07D 275/04* (2013.01); *C07D 279/24* (2013.01); *C07D 293/12* (2013.01); *C07D 405/06* (2013.01); *C07D 409/06* (2013.01)

(58) Field of Classification Search
CPC .. C07D 275/04; C07D 279/24; C07D 293/12; C07D 335/20; C07D 405/06; C07D 409/06; A61K 31/41; A61K 31/497
See application file for complete search history.

(56) References Cited

U.S. PATENT DOCUMENTS

2002/0193371 A1  12/2002  Telerman et al.
2004/0072824 A1   4/2004  Telerman et al.

FOREIGN PATENT DOCUMENTS

| WO | 02096400 A1 | 12/2002 |
| WO | 2008002641 A2 | 1/2008 |
| WO | 2009158526 A2 | 12/2009 |
| WO | 2012097054 A1 | 7/2012 |
| WO | 2014055634 A1 | 4/2014 |

OTHER PUBLICATIONS

Product Monograph, Clopixol, Sep. 13, 2011 (Year: 2011).*
Ford et al., Cancer Research, 50, 1748-1756, Mar. 15, 1990. (Year: 1990).*
Hoeferlin et al., J Surg. Sci. Dec. 2013 ;1(1): 3-7. (Year: 2013).*
Behmoaram et al., "Focal Adhesion Kinase-Related Proline-Rich Tyrosine Kinase 2 and Focal Adhesion Kinase are Co-Overexpressed in Early-Stage and Invasive ErbB-2-Positive Breast Cancer and Cooperate for Breast Cancer Cell Tumorigenesis and Invasiveness", The American Journal of Pathology, vol. 173, No. 5, Nov. 2008, pp. 1540-1550.
Bijian et al., "Synthesis and Biological Activity of Novel Organoselenium Derivatives Targeting Multiple Kinases and Capable of Inhibiting Cancer Progression to Metastases", European Journal of Medicinal Chemistry, vol. 48, Feb. 2012, pp. 143-152.

(Continued)

*Primary Examiner* — Jean P Cornet
(74) *Attorney, Agent, or Firm* — Lerner, David, Littenberg, Krumholz & Mentlik, LLP

(57) ABSTRACT

The present invention relates to compounds of the following general formula (I) or (II): or a pharmaceutically acceptable salt and/or solvate thereof, for use in the treatment and/or in the prevention of ErbB2 dependent cancers, and pharmaceutical compositions containing such compounds.

14 Claims, 31 Drawing Sheets
Specification includes a Sequence Listing.

(56) References Cited

OTHER PUBLICATIONS

Chen et al., "Selective and Cell-Active Inhibitos of the USP1/UAF1 Deubiquitinase Complex Reverse Cisplatin Resistance in Non-small Cell Lung Cancer Cells", Chemistry & Biology, vol. 18, No. 11, Nov. 2011, pp. 1390-1400.
Choi et al., "Potential Inhibition of PDK1/Akt Signaling by Phenothiazines Suppresses Cancer Cell Proliferation and Survival", Annals of the New York Academy of Sciences, vol. 1138, No. 1, Sep. 2008, pp. 393-403.
Database Biosis [Online] Biosciences Information Service, Philadelphia, PA, US; May 2001 (May 2001), Xia Xianmin et al: "Ebp1, an ErbB-3 binding protein, interacts with Rb and affects Rb transcriptional regulation", XP002767953, Database accession No. PREV200100220478 abstract.
Database Medline [Online] US National Library of Medicine (NLM), Bethesda, MD, US; Sep. 1996 (Sep. 1996), Cardillo M et al: "Heregulin induces increase in sensitivity of an erbB-2-overexpressing breast cancer cell type to lysis by lymphokine-activated killer cells.", XP002758416, Database accession No. NLM8917631 abstract.
Engman et al., "Diaryl Chalcogenides as Selective Inhibitors of Thioredoxin Reductase and Potential Antitumor Agents", Anticancer Research, Sep. 1997, pp. 4599-4605.
Fen Jing et al., "Synthesis and In Vitro Antiproliferative Evaluation of Novel Hybrids from 1,3,4-Thiadiazole and Benzisoselenazolone", Chemical and Pharmaceutical Bulletin, vol. 63, No. 6, Jun. 2015, pp. 431-437.
Ford et al., "Cellular and Biochemical Characterization of Thioxanthenes for Reversal of Multidrug Resistance in Human and Murine Cell Lines", Cancer Research, vol. 50, No. 6, Mar. 1990, pp. 1748-1756.
Gopinath et al., "Benzisothiazolones Arrest the Cell Cycle at the G2/M Phase and Induce Apoptosis in HeLa Cells", MedChemComm, vol. 4, No. 4, Feb. 2013, pp. 749-752.
International Search Report for PCT/EP Application No. 2017050471, dated Apr. 19, 2017.
Matsson et al., "A Global Drug Inhibition Pattern for the Human ATP-Binding Cassette Transporter Breast Cancer Resistance Protein (ABCG2)", Journal of Pharmacology and Experimental Therapeutics, vol. 323, No. 1, Oct. 2007, pp. 19-30.
Pajeva et al., "Molecular Modeling of Phenothiazines and Related Drugs as Multidrug Resistance Modifiers: A comparative Molecular Field Analysis Study", Journal of Medicinal Chemistry, vol. 41, No. 11, May 1998, pp. 1815-1826.
Sayegh et al., "Identification of Small Molecule Inhibitors of Jumonji AT-Rich Interactive Domain 1B (JARID1B) Histone Demethylase by a Sensitive High Throughput Screen", Journal of Biological Chemistry, Feb. 2013, pp. 9408-9417.
Tuynder et al., "Translationally Controlled Tumor Protein is a Target of Tumor Reversion", Proceedings of the National Academy of Sciences, vol. 101, No. 43, Oct. 2004, pp. 15364-15369.
Wilson et al., "High-Throughput Screen Identifies Novel Inhibitors of Cancer Biomarker x-Methylacyl Coenzyme A Racemase (AMACR/P504S)", Molecular Cancer Therapeutics, Mar. 2011, pp. 825-838.
Xianmin et al., "Ebp1, an ErbB-3 Binding Protein, Interacts With Rb and Affects Rb Transcriptional Regulation", Journal of Cellular Physiology, vol. 187, May 2001, pp. 209-217.
Zong et al., "Harnessing the lysosome-Dependent Antitumor Activity of Phenothiazines in Human Small Cell Lung Cancer", Cell Death & Disease, Mar. 2014, pp. 1-11.
O'Brien, et al., "Targeting PI3K/mTOR Overcomes Resistance to HER2-Targeted Therapy Independent of Feedback Activation of AKT", American Association for Cancer Research, Jul. 1, 2014, pp. 3507-3520.

* cited by examiner

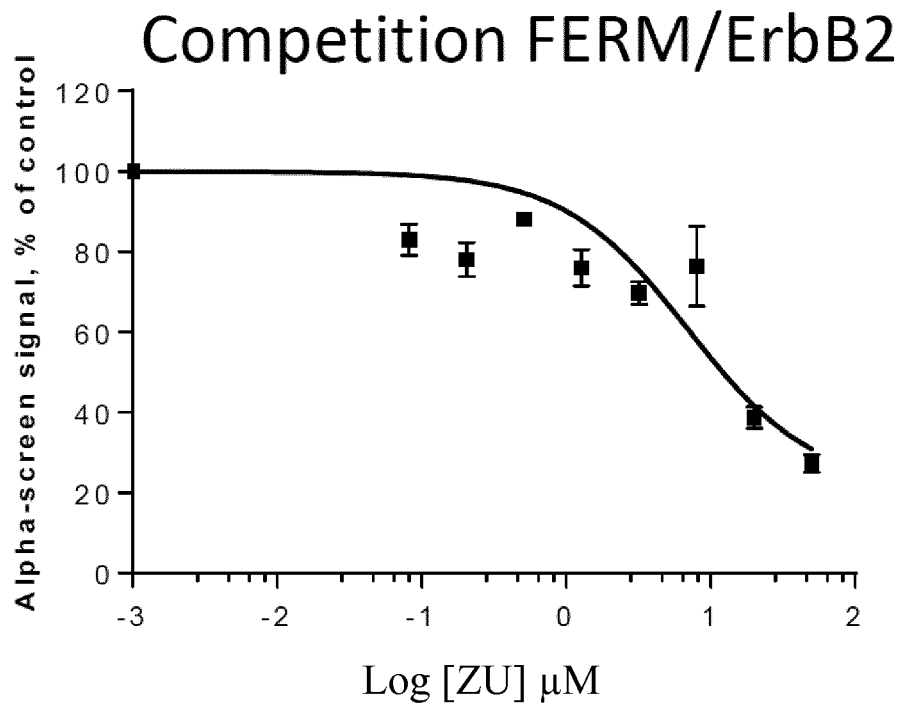
Fig. 1A
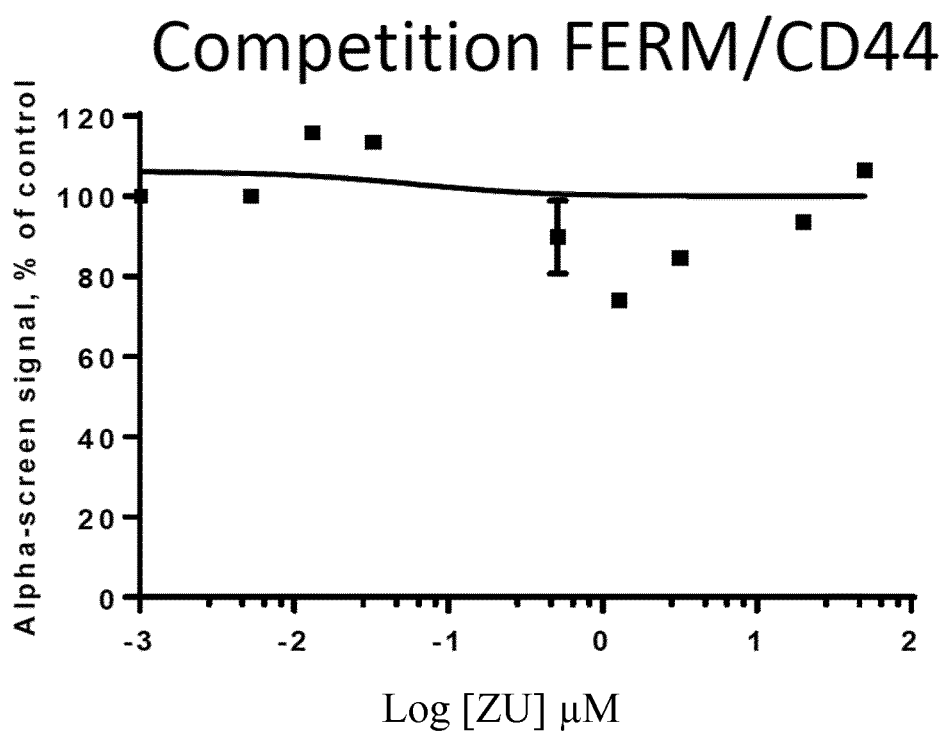
Fib. 1B

ZUCLOPENTHIXOL HYDROCHLORIDE DERIVATIVES AND EBSELEN DERIVATIVES AS ERBB2 INHIBITORS

CROSS-REFERENCE TO RELATED APPLICATIONS

The present application is a national phase entry under 35 U.S.C. § 371 of International Application No. PCT/EP2017/050471, filed Jan. 11, 2017, published as International Publication No. WO 2017/121755 A1, which claims priority from European Patent Application No. 16305019.8, filed Jan. 11, 2016, all of which are incorporated herein by reference.

TECHNICAL FIELD

The present invention relates to two families of potent and selective ErbB2/HER2 inhibitory compounds: Zuclopenthixol hydrochloride derivatives and Ebselen derivatives. In particular, the present invention relates to Zuclopenthixol hydrochloride derivatives and Ebselen derivatives for use in the treatment and/or in the prevention of ErbB2/HER2-dependent cancers.

BACKGROUND INFORMATION

Breast cancer is the most frequently diagnosed cancer and the leading cause of cancer death in women worldwide, accounting for 23% (1.38 million) of the total new cancer cases and 14% (458,400) of the total cancer deaths in 2008. About half the breast cancer cases and 60% of the deaths are estimated to occur in economically developing countries. The rate of incidence observed in France is among the strongest in Europe and is in constant increase.

20-30% of primary human breast cancers are due to the deregulated expression of ErbB2/HER2 or the expression of mutated or truncated forms of ErbB2/HER2: it represents approximately 8,000 patients a year in France and 450,000 patients a year worldwide. ErbB2/HER2 overexpression or abnormally activated is associated with a poor diagnosis, tumors with deregulated ErbB2/HER2 having been shown to grow faster, to be more aggressive and to be less sensitive to chemotherapy or to hormonotherapy. ErbB2/HER2 deregulation is also associated with disease recurrence. Then, so called ErbB2/HER2 dependent cancers constitute a very specific group of cancer of an utmost interest in public health. Only 25% of the treated patients respond to the actual therapies. The actual strategies aiming at targeting the extracellular domain (anti-HER2 antibody therapies Herceptin/trastuzumab and pertuzumab from Roche/Genentech, USA) or the kinase activity of the receptor (small molecule tyrosine kinase inhibitors, lapatinib/Tykerb, GSK, USA) have proven to exhibit limited actions. In particular, these molecules have no potent action on the mutated and truncated forms of HER2. Concerning trastuzumab, 66% to 88% of treated patients never respond to treatment (i.e. present a "primary resistance") and among the one-third of the treated patients that respond to this agent, a disease progression on average in less than one year (i.e. develop an "acquired resistance") is generally observed. Trastuzumab emtansine (also known as T-DM1) has been recently developed and is a novel antibody-drug conjugate that contains the antibody trastuzumab and DM1, a microtubule-inhibitory maytansinoid, linked through a thioether bond. Upon binding to HER2, T-DM1 is then internalized and degraded in lysosomes to release DM1-containing cytotoxic components which cause inhibition of cell division and cell growth, and eventually cell death. Primary resistance of HER2-positive metastatic breast cancer to T-DM1 appears to be relatively infrequent, but most patients treated with T-DM1 develop acquired drug resistance, by mechanisms related to trastuzumab resistance combined to some related to DM1 resistance (upregulation of multi-drug resistance transporters or altered microtubule dynamics for examples) (Li G et al. Trastuzumab-DM1: mechanisms of action and mechanisms of resistance 2010).

Treatments with small molecule tyrosine kinase inhibitors (e.g. lapatinib) are often associated to increased toxicity due to a non-specific inhibition of promiscuous ErbB and non-ErbB kinases by these agents, limiting the extent to which they can be used safely. The median duration of response to lapatinib was less than one year, and a majority of trastuzumab-pre-treated patients (~80%) failed to respond.

The efficacy of current treatments is limited by the development of therapeutic resistance mainly attributed to the expression of $p95^{HER2}$, as this highly active truncated form of HER2 lacks the recognition site for trastuzumab. However, therapeutic resistance to HER2 specific treatment or occurrence of metastasis can also be due to point mutations in HER2 protein sequence: for instance, K753E mutation and resistance to lapatinib or V777L and resistance to trastuzumab [Zuo et al. *Clin Cancer Res* 2016, 22(19), 4859-4869].

There is therefore an urgent need for the development of alternative approaches that would specifically target ErbB2/HER2 to reduce the risk of toxicity and also work efficiently on mutated and truncated forms of ErbB2 resistant to the current treatments of ErbB2 cancers.

It was previously shown that interaction of the FERM domain of the ERM family members (Ezrin, Moesin, Radixin) and of the related member Merlin with the juxtamembrane domain of ErbB2 prevents ErbB2 activation. This interaction stabilizes ErbB2 in a catalytically repressed state by exerting a molecular constraint on the juxtamembrane domain of ErbB2, restricting access of the kinase domain to substrate tyrosines (WO/2011/036211). A High Throughput Screening assay based on the disruption of the interaction between the juxtamembrane domain of HER2 and the Ezrin FERM domain was then set up to identify small molecule inhibitors which will behave as the FERM domain to actively block ErbB2 (FR1452246).

BRIEF SUMMARY OF THE INVENTION

The applicants of the present invention have thus discovered two families of potent and selective small-molecule inhibitors of ErbB2 that mimic the effect of the FERM domain of the ERM proteins on ErbB2: these compounds directly bind to the juxtamembrane domain of ErbB2, inhibit ErbB2 activation in gastric, ovarian and breast cancer cells overexpressing ErbB2 and selectively inhibit ErbB2-dependent cell proliferation. Furthermore, they inhibit the growth of human tumors overexpressing ErbB2 in murine orthotopic xenograft models and in vitro the growth of human breast cancer cells with a characterized resistance status to trastuzumab. It was further demonstrated that these molecules are able to target mutated ErbB2 implicated in tumors aggressiveness and resistance. Furthermore these molecules specifically block the ligand-independent activation of ErbB2 and do not interfere with physiological ErbB2 activation in heterodimers with the other ErbB family members.

These compounds thus appear to be very attractive for therapeutic interventions on cancers with deregulated expression of ErbB2.

"ErbB2" and "HER2" are used herein interchangeably in the present invention.

A first object of the invention is a compound of the following general formula (I):

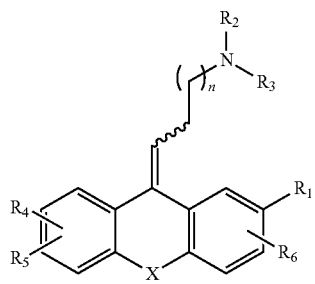

(I)

or a pharmaceutically acceptable salt and/or solvate thereof, wherein:

X is a sulfur atom or an oxygen atom;

$R_1$ is hydrogen atom, halo, —CN, —$NO_2$, —NO, —CHO, —$NR_7R_8$, —$CO_2R_9$, —$SO_2R_{10}$, —$SO_2NR_{11}R_{12}$, —$OR_{13}$, —$COR_N$, —$SR_{15}$, —$CONR_{16}R_{17}$, —$SO_2(O)R_{18}$ or a group selected from saturated ($C_1$-$C_6$)alkyl, unsaturated ($C_2$-$C_6$)alkyl and aryl, said group being optionally substituted with one or several groups selected from halo, —$CF_3$, —CN and —$SO_2NR_{19}R_{20}$;

$R_2$ and $R_3$ form together with the nitrogen atom to which they are chemically linked, an heterocycle or an heteroaryl group, optionally substituted with one or several groups selected from halo, —$CO_2R_{21}$, and a ($C_1$-$C_6$)alkyl group optionally substituted with one or several groups selected from halo, —$OR_{22}$, —$SR_{23}$, —$S(O)R_{24}$, —$SO_2R_{25}$, —$SO_2NR_{26}R_{27}$, —$OC(O)R_{28}$, —$NR_{29}COR_{30}$, —$NR_{31}CONR_{32}R_{33}$, —$NR_{34}C(O)OR_{35}$, —$CO_2R_{36}$, —$CONR_{37}R_{38}$, —$OCO_2R_{39}$, —$OCONR_{40}R_{41}$, —$COR_{42}$, —$NO_2$, _$CF_3$, and —CN;

$R_4$, $R_5$ and $R_6$ are, independently of one another, hydrogen atom, halo, —CN, —$NO_2$, —NO, —CHO, —$NR_{43}R_{44}$, —$CO_2R_{45}$, —$S(O)R_{46}$, —$SO_2R_{47}$, —$SO_2NR_{48}R_{49}$, —$OCOR_{50}$, —$NR_{51}COR_{52}$, —$NR_{53}CO(O)R_{54}$, —$NR_{55}CONR_{56}R_{57}$, —$CO_2R_{58}$, —$OR_{59}$, —$COR_{60}$, —$SR_{61}$, —$CONR_{62}R_{63}$, —$OCONR_{64}R_{65}$, —$SO_2(O)R_{66}$, or a group selected from saturated ($C_1$-$C_6$)alkyl, unsaturated ($C_2$-$C_6$)alkyl and aryl, said group being optionally substituted with one or several groups selected from halo, —$CF_3$, —CN, and —$SO_2NR_{67}R_{68}$;

$R_7$ to $R_{68}$ are, independently of one another, a hydrogen atom or a ($C_1$-$C_{10}$)alkyl, aryl or aryl($C_1$-$C_6$)alkyl group, said group being optionally substituted with one or several groups selected from halo, —OH, —$CF_3$, —CN, and —$SO_2NR_{69}R_{70}$; with the proviso that $R_{21}$ is not an hydrogen atom.

$R_{69}$ and $R_{70}$ are independently of one another, a hydrogen atom or a ($C_1$-$C_{10}$)alkyl, aryl or aryl($C_1$-$C_6$)alkyl group; and n is an integer selected from 1 to 6;

for use in the treatment and/or in the prevention of ErbB2-dependent cancers.

A second object of the invention is a compound of the following general formula (II):

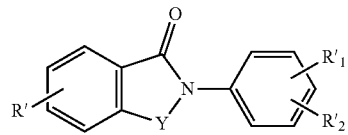

(II)

or a pharmaceutically acceptable salt and/or solvate thereof, wherein:

Y is Se═O or a sulfur atom, preferably Y'Se═O;

$R'_1$ and $R'_2$ are, independently of one another, H, halo, ($C_1$-$C_6$)alkyl, CN, $CF_3$, CHO, $CO_2R'_4$, $SO_2R'_5$, $SO_2NR'_6R'_7$, $COR'_8$, $CONR'_9R'_{10}$, $SO_2OR'_{11}$;

$R'_3$ is H, halo, ($C_1$-$C_6$)alkyl, $OR'_{12}$, $NR'_{13}R'_{14}$, $SR'_{15}$, $S(O)R'_{16}$, $SO_2R'_{17}$, $SO_2NR'_{18}R'_{19}$, $OCOR'_{20}$, $NR'_{21}COR'_{22}$, $NR'_{23}CONR'_{24}R'_{25}$, $NR'_{26}C(O)OR'_{27}$, $CO_2R'_{28}$, $CONR'_{29}R'_{30}$, $OCO_2R'_{31}$, $OCONR'_{32}R'_{33}$, $COR'_{34}$, nitro ($NO_2$), cyano (CN); and $R'_4$ to $R'_{34}$ are, independently of one another, H or a ($C_1$-$C_6$)alkyl, aryl or aryl($C_1$-$C_6$)alkyl group, said group being optionally substituted with one or several groups selected from halo;

for use in the treatment and/or in the prevention of ErbB2-dependent cancers.

Definitions

For the purpose of the invention, the term "pharmaceutically acceptable" is intended to mean what is useful to the preparation of a pharmaceutical composition, and what is generally safe and non-toxic, for a pharmaceutical use.

The term "pharmaceutically acceptable salt or solvate" is intended to mean, in the framework of the present invention, a salt or solvate of a compound which is pharmaceutically acceptable, as defined above, and which possesses the pharmacological activity of the corresponding compound.

The Pharmaceutically Acceptable Salts Comprise:

(1) acid addition salts formed with inorganic acids such as hydrochloric, hydrobromic, sulfuric, nitric and phosphoric acid and the like; or formed with organic acids such as acetic, benzenesulfonic, fumaric, glucoheptonic, gluconic, glutamic, glycolic, hydroxynaphtoic, 2-hydroxyethanesulfonic, lactic, maleic, malic, mandelic, methanesulfonic, muconic, 2-naphtalenesulfonic, propionic, succinic, dibenzoyl-L-tartaric, tartaric, p-toluenesulfonic, trimethylacetic, and trifluoroacetic acid and the like, and (2) base addition salts formed when an acid proton present in the compound is either replaced by a metal ion, such as an alkali metal ion, an alkaline-earth metal ion, or an aluminium ion; or coordinated with an organic or inorganic base. Acceptable organic bases comprise diethanolamine, ethanolamine, N-methylglucamine, triethanolamine, tromethamine and the like. Acceptable inorganic bases comprise aluminium hydroxide, calcium hydroxide, potassium hydroxide, sodium carbonate and sodium hydroxide.

Acceptable solvates for the therapeutic use of the compounds of the present invention include conventional solvates such as those formed during the last step of the preparation of the compounds of the invention due to the presence of solvents. As an example, mention may be made of solvates due to the presence of water (these solvates are also called hydrates) or ethanol.

Within the meaning of this invention, "stereoisomers" is intended to designate diastereoisomers or enantiomers.

These are therefore spatial isomers. Stereoisomers which are not mirror images of one another are thus designated as "diastereoisomers," and stereoisomers which are non-superimposable mirror images are designated as "enantiomers". Traditionally, double bond stereochemistry is described as either cis (Latin, on this side) or trans (Latin, across), in reference to the relative position of substituents on either side of a double bond.

The terms "$(C_1-C_6)$alkyl" and "saturated $(C_1-C_6)$alkyl", as used in the present invention, both refer to a straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The terms "$(C_1-C_{10})$alkyl", as used in the present invention, refers to a straight or branched saturated hydrocarbon chain containing from 1 to 10 carbon atoms including, but not limited to, methyl, ethyl, n-propyl, iso-propyl, n-butyl, iso-butyl, sec-butyl, t-butyl, n-pentyl, n-hexyl, n-heptyl, n-octyl, n-nonyl, n-decyl, and the like.

The term "unsaturated $(C_2-C_6)$alkyl", as used in the present invention, refers to a straight or branched unsaturated hydrocarbon chain containing from 2 to 6 carbon atoms and comprising at least one double or triple bond, notably one double bond, including, but not limited to, ethenyl, propenyl, butenyl, pentenyl, hexenyl and the like. It can be in particular an allyl group.

The term "aryl", as used in the present invention, refers to an aromatic hydrocarbon group comprising preferably 6 to 10 carbon atoms and comprising one or more, notably 1 or 2, fused rings, such as, for example, a phenyl or naphtyl group. Advantageously, it will be a phenyl group.

The term "aryl-$(C_1-C_6)$alkyl", as used in the present invention, refers to an aryl group as defined above bound to the molecule via a $(C_1-C_6)$alkyl group as defined above. In particular, the aryl-$(C_1-C_6)$alkyl group is a benzyl group.

The term "heterocycle" as used in the present invention refers to a saturated, unsaturated or aromatic hydrocarbon monocycle or polycycle (comprising fused, bridged or spiro rings), such as a bicycle, in which one or more, advantageously 1 to 4, and more advantageously 1 or 2, carbon atoms have each been replaced with a heteroatom selected from nitrogen, oxygen and sulphur atoms, and notably being a nitrogen atom. Advantageously, the heterocycle comprises 5 to 15, notably 5 to 10 atoms in the ring(s). Each ring of the heterocycle has advantageously 5 or 6 members.

According to a particular embodiment, the heterocycle is a saturated, unsaturated or aromatic hydrocarbon monocycle or bicycle (comprising fused, bridged or spiro rings, notably fused rings), each cycle having 5 or 6 members and 1 to 4, notably 1 or 2, carbon atoms having each been replaced with a nitrogen or oxygen atom, notably a nitrogen atom.

A heterocycle can be notably thiophene, furan, pyrrole, imidazole, pyrazole, oxazole, isoxazole, thiazole, isothiazole, triazoles (1,2,3-triazole and 1,2,4-triazole), benzofuran, indole, benzothiophene, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, piperidine, piperazine, triazinane, morpholine, pyrrolidine, dihydropyridines, dihydropyrimidines (notably 1,2-dihydropyrimidine), dihydropyridazines, dihydropyrazines, dihydrotriazines, tetrahydropyridines, tetrahydropyrimidines, tetrahydropyridazines, tetrahydropyrazines, tetrahydrotriazines, etc. In particular, the heterocycle is piperidine or piperazine.

The term "nitrogen-containing heterocycle" as used in the present invention refers to a heterocycle as defined above containing at least one nitrogen atom.

Such a nitrogen-containing heterocycle is thus a saturated, unsaturated or aromatic hydrocarbon monocycle or polycycle (comprising fused, bridged or spiro rings), such as a bicycle, in which one or more, advantageously 1 to 4, and more advantageously 1 or 2, carbon atoms have each been replaced with a heteroatom selected from nitrogen, oxygen and sulphur atoms, at least one of the heteroatom(s) being a nitrogen atom, and notably all the heteroatoms are nitrogen. Advantageously, the heterocycle comprises 5 to 15, notably 5 to 10 atoms in the ring(s). Each ring of the heterocycle has advantageously 5 or 6 members.

According to a particular embodiment, the heterocycle is a saturated, unsaturated or aromatic hydrocarbon monocycle or bicycle (comprising fused, bridged or spiro rings, notably fused rings), each cycle having 5 or 6 members, in which one carbon atom has been replaced with a nitrogen atom and optionally 1 to 3, notably 1, additional carbon atom(s) has/have each been replaced with a nitrogen or oxygen atom, notably a nitrogen atom.

A nitrogen-containing heterocycle can be notably pyrrole, imidazole, pyrazole, oxazole, isoxazole, thiazole, isothiazole, triazoles (1,2,3-triazole and 1,2,4-triazole), indole, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, piperidine, piperazine, triazinane, morpholine, pyrrolidine, dihydropyridines, dihydropyrimidines (notably 1,2-dihydropyrimidine), dihydropyridazines, dihydropyrazines, dihydrotriazines, tetrahydropyridines, tetrahydropyrimidines, tetrahydropyridazines, tetrahydropyrazines, tetrahydrotriazines, etc. In particular, the heterocycle is piperidine or piperazine.

The term "heteroaryl" as used in the present invention refers to an aromatic heterocycle as defined above.

According to a particular embodiment, the heteroaryl is an aromatic hydrocarbon monocycle or bicycle (i.e. comprising two fused rings), each cycle having 5 or 6 members, notably 6 members, and 1 to 4, notably 1 or 2, carbon atoms having each been replaced with a nitrogen or oxygen atom, notably a nitrogen atom.

A heteroaryl can be notably thiophene, furan, pyrrole, imidazole, pyrazole, oxazole, isoxazole, thiazole, isothiazole, triazoles (1,2,3-triazole and 1,2,4-triazole), benzo furan, indole, benzothiophene, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, etc.

The term "nitrogen-containing heteroaryl" as used in the present invention refers to an aromatic nitrogen-containing heterocycle as defined above.

According to a particular embodiment, the nitrogen-containing heteroaryl is an aromatic hydrocarbon monocycle or bicycle (i.e. comprising two fused rings), each cycle having 5 or 6 members, notably 6 members, in which one carbon atom has been replaced with a nitrogen atom and optionally 1 to 3, notably 1, additional carbon atom(s) has/have each been replaced with a nitrogen or oxygen atom, notably a nitrogen atom.

A nitrogen-containing heteroaryl can be notably pyrrole, imidazole, pyrazole, oxazole, isoxazole, thiazole, isothiazole, triazoles (1,2,3-triazole and 1,2,4-triazole), indole, benzimidazole, indazole, benzoxazole, benzisoxazole, benzothiazole, benzisothiazole, pyridine, pyrimidine, pyridazine, pyrazine, triazine, quinoline, isoquinoline, quinoxaline, quinazoline, etc.

The term "halogen", abbreviated "halo", as used in the present invention, refers to a fluorine, bromine, chlorine or iodine atom.

The term "ErbB2 dependent cancer" as used in the present invention refers to any cancer case for which cancer cells exhibiting a deregulation of ErbB2 gene (also called HER2) have been identified, in opposition to "ErbB2-independent" or "ErbB2 negative" cancer. More particularly said deregulation can correspond to an amplification of ErbB2/HER2 gene. This amplification can be detected at the genetic level, or at the protein level. For example, guidelines emitted by the American society of Clinical Oncology/College of American Pathologists (ASCO/CAP) for breast cancer set several cut-offs for determining the ErbB2 status of breast cancer.

These guidelines prescribe that a cancer should be considered as "ErbB2 dependent" or "ErbB2 positive" if, for the primary site and if possible for the metastatic site:
  a uniform and intense membrane staining of more than 30% of invasive tumor cells is observed in immunochemistry (IHC), or
  i) a FISH amplified ratio of HER2 to CEP17 (chromosome 17 centromere) superior or equal to 2.0 (dual probe testing) or ii) a FISH amplified ratio of HER2 to CEP17 (chromosome 17 centromere) inferior to 2.0 (dual probe testing) with an average HER2 copy number of at least 6 copies per nucleus (single probe testing) is determined, or iii) a single probe average of at least 6 signals for the HER2 copy number per cells.

Besides, a cancer is considered as "ErbB2-independent" or "ErbB2 negative" when, for the primary site and if possible for the metastatic site:
  in IHC, no staining or a weak incomplete membrane staining, or a weak but complete membrane staining is observed in less than 10% of cells, or
  the FISH HER2/CEP17 ratio inferior to 2 with an average copy number of HER2 inferior to 4 signals per cells is noticed (dual probe testing), or an average copy number of HER2 inferior to 4 signals per cell is noticed (in cases where a single probe is used).

The HER2 status will be considered as equivocal (then a new test should be performed) when, for the primary site and, if possible, for the metastatic site:
  in IHC, i) an incomplete labelling of circumferential membrane and/or weak/moderate labelling is noticed but within superior to 10% of the invasive tumor cells or ii) a complete and intense labelling of circumferential membrane is noticed but for 10% or less of the invasive tumor cells, or
  the FISH HER2/CEP17 ratio inferior to 2 with an average copy number of HER2 of at least 4 signals but less than 6 signals per cell is noticed (dual probe testing), or an average copy number of HER2 of at least 4 signals but less than 6 signals per cell is noticed (in cases where a single probe is used).

Deregulation of HER2 gene can also correspond to activating mutations in HER2 gene disregarding its copy number, leading to an increase of the tyrosine kinase activity of the ErbB2/HER2. For example, said activating mutations can be V659E, G309A, D769H, D769Y, V777L, P780ins, V842I, R896C, K753E or L755S and can be detected by Polymerase Chain Reaction or any sequencing technique [Bose et al. Cancer Discov. 2013, 3(2), 224-237; Zuo et al. Clin Cancer Res 2016, 22(19), 4859-4869]. Also, both an amplification of ErbB2 gene and a somatic activating mutation can be detected in the same case of cancer.

Well known molecular biology tests other than Fish or IHC, using negative and positive control cells with an established HER2 status, can be used for determining the HER2 status of a cancer by way of comparison, as for example Enzyme-Linked Immunosorbent Assays, Western blotting assays, Polymerase Chain Reaction etc. . . .

DETAILED DESCRIPTION OF THE INVENTION

Zuclopenthixol Hydrochloride Derivatives

According to a particular embodiment of the first object of the present invention, in the compound of the general formula (I) or a pharmaceutically acceptable salt and/or solvate thereof for use in the treatment and/or in the prevention of ErbB2-dependent cancers, $R_1$ is hydrogen atom, halo, —CN, —NO$_2$, —NO, —CHO, —NR$_7$R$_8$, —CO$_2$R$_9$, —SO$_2$R$_{10}$, —SO$_2$NR$_{11}$R$_{12}$, —COR$_N$, —CONR$_{16}$R$_{17}$, —SO$_2$(O)R$_{18}$ or a group selected from saturated (C$_1$-C$_6$)alkyl, unsaturated (C$_1$-C$_6$)alkyl and aryl, said group being optionally substituted with one or several groups selected from halo, —CF$_3$, —CN and —SO$_2$NR$_{19}$R$_{20}$; R$_7$ to R$_{12}$, R$_{14}$ and R$_{16}$ to R$_{20}$ being as defined above.

In particular, $R_1$ is hydrogen atom, halo, —CN, —CHO, —NR$_7$R$_8$, —CO$_2$R$_9$, —SO$_2$R$_{10}$, —SO$_2$NR$_{11}$R$_{12}$, —COR$_N$, —CONR$_{16}$R$_{17}$, —SO$_2$(O)R$_{18}$ or a group selected from saturated (C$_1$-C$_6$)alkyl, unsaturated (C$_1$-C$_6$)alkyl and aryl, said group being optionally substituted with one or several groups selected from halo, —CF$_3$, —CN and —SO$_2$NR$_{19}$R$_{20}$; R$_7$ to R$_{12}$, R$_{14}$ and R$_{16}$ to R$_{20}$ being as defined above.

In particular, $R_1$ is hydrogen atom, halo, —CN, —CHO, —NR$_7$R$_8$, —CO$_2$R$_9$, —SO$_2$R$_{10}$, —SO$_2$NR$_{11}$R$_{12}$, —COR$_N$, —CONR$_{16}$R$_{17}$, —SO$_2$(O)R$_{18}$ or a group selected from saturated (C$_1$-C$_6$)alkyl and unsaturated (C$_1$-C$_6$)alkyl, said group being optionally substituted with one or several groups selected from halo, —CF$_3$, —CN and —SO$_2$NR$_{19}$R$_{20}$; R$_7$ to R$_{12}$, R$_{14}$ and R$_{16}$ to R$_{20}$ being as defined above, preferably R$_7$ to R$_{12}$, R$_{14}$ and R$_{16}$ to R$_{20}$ each represent, independently of one another, a (C$_1$-C$_{10}$)alkyl group, more preferably a (C$_1$-C$_6$)alkyl group.

Advantageously, $R_1$ is notably hydrogen atom, halo, preferably Cl or F, —CN, —SO$_2$NR$_{11}$R$_{12}$ or —CF$_3$; R$_{11}$ and R$_{12}$ being as defined above, preferably R$_{11}$ and R$_{12}$ each represent, independently of one another, a (C$_1$-C$_{10}$)alkyl group, more preferably a (C$_1$-C$_6$)alkyl group.

More advantageously, $R_1$ is a hydrogen atom, —Cl, —SO$_2$N(CH$_3$)$_2$ or —CF$_3$.

$R_1$ is notably hydrogen atom, Cl or —CF$_3$.

In the above definitions of $R_1$, the (C$_1$-C$_6$)alkyl is preferably methyl or ethyl.

In the above definitions of $R_1$, the aryl is preferably phenyl.

In the above definitions of $R_1$, the halo is preferably Cl or F.

In a preferred embodiment, in the compound of the general formula (I), $R_2$ and $R_3$ form together with the nitrogen atom to which they are chemically linked, an heterocycle or an heteroaryl group, substituted with one or several (C$_1$-C$_6$)alkyl group optionally substituted with one or several groups selected from —OR$_{22}$, —SR$_{23}$, —S(O)R$_{24}$, —SO$_2$R$_{25}$, —SO$_2$NR$_{26}$R$_{27}$, —OC(O)R$_{28}$, —NR$_{29}$COR$_{30}$, —NR$_{31}$CONR$_{32}$R$_{33}$, —NR$_{34}$C(O)OR$_{35}$, —CO$_2$R$_{36}$, —CONR$_{37}$R$_{38}$, —OCO$_2$R$_{39}$, —OCONR$_{40}$R$_{41}$, —COR$_{42}$, —NO$_2$, and —CN; R$_{22}$ to R$_{42}$ being as defined above. As shown in examples, compounds according to this embodiment exhibit a non-toxic profile against normal epithelial cell.

In particular, $R_2$ and $R_3$ form together with the nitrogen atom to which they are chemically linked, an heterocycle or an heteroaryl group, substituted with one or several ($C_1$-$C_6$) alkyl group optionally substituted with one or several groups selected from —$OR_{22}$, —$SR_{23}$, —$S(O)R_{24}$, —$SO_2R_{25}$, —$SO_2NR_{26}R_{27}$, —$OC(O)R_{28}$, —$NR_{29}COR_{30}$, —$NR_{31}CONR_{32}R_{33}$, —$NR_{34}C(O)OR_{35}$, —$CONR_{37}R_{38}$, —$OCO_2R_{39}$, —$OCONR_{40}R_{41}$, —$COR_{42}$, —$NO_2$ and —CN; $R_{22}$ to $R_{42}$ being as defined above. As shown in examples, besides being non-toxic against normal endothelial cells, compounds according to this embodiment allow a potent inhibition of the ErbB2 activation.

In particular, $R_2$ and $R_3$ form together with the nitrogen atom to which they are chemically linked, an heterocycle or an heteroaryl group, substituted with one ($C_1$-$C_6$)alkyl group optionally substituted with one or several groups selected from —$OR_{22}$, —$SR_{23}$, —$S(O)R_{24}$, —$SO_2R_{25}$, —$SO_2NR_{26}R_{27}$, —$OC(O)R_{28}$, —$NR_{29}COR_{30}$, —$NR_{31}CONR_{32}R_{33}$, —$NR_{34}C(O)OR_{35}$, —$CO_2R_{36}$, —$CONR_{37}$, $R_{38}$, —$OCO_2R_{39}$, —$OCONR_{40}R_{41}$, —$COR_{42}$, —$NO_2$ and —CN; $R_{22}$ to $R_{42}$ being as defined above.

In particular, $R_2$ and $R_3$ form together with the nitrogen atom to which they are chemically linked, an heterocycle or an heteroaryl group, substituted with one ($C_1$-$C_6$)alkyl group optionally substituted with one or several groups selected from —$OR_{22}$, —$SR_{23}$, —$S(O)R_{24}$, —$SO_2R_{25}$, —$SO_2NR_{26}R_{27}$, —$OC(O)R_{28}$, —$NR_{29}COR_{30}$, —$NR_{31}CONR_{32}R_{33}$, —$NR_{34}C(O)OR_{35}$, —$CONR_{37}R_{38}$, —$OCO_2R_{39}$, —$OCONR_{40}R_{41}$, —$COR_{42}$, —$NO_2$ and —CN; $R_{22}$ to $R_{42}$ being as defined above.

Notably, $R_2$ and $R_3$ form together with the nitrogen atom to which they are chemically linked, an heterocycle or an heteroaryl group, substituted with one ($C_1$-$C_6$)alkyl group optionally substituted with one or several groups selected from —$OR_{22}$, —$SR_{23}$, —$S(O)R_{24}$, —$SO_2R_{25}$, —$SO_2NR_{26}R_{27}$, —$OC(O)R_{28}$, —$OCO_2R_{39}$ and —$COR_{42}$; and $R_{22}$ to $R_{28}$, $R_{39}$ and $R_{42}$ are, independently of one another, a hydrogen atom or a ($C_1$-$C_{10}$)alkyl group.

In particular, $R_2$ and $R_3$ form together with the nitrogen atom to which they are chemically linked, an heterocycle or an heteroaryl group, substituted with one ($C_1$-$C_6$)alkyl group substituted with one or several groups selected from —$OR_{22}$, —$SR_{23}$, —$S(O)R_{24}$, —$SO_2R_{25}$, —$SO_2NR_{26}R_{27}$, —$OC(O)R_{28}$, —$OCO_2R_{39}$ and —$COR_{42}$; and $R_{22}$ to $R_{28}$, $R_{39}$ and $R_{42}$ are, independently of one another, a hydrogen atom or a ($C_1$-$C_{10}$)alkyl group.

In particular, $R_2$ and $R_3$ form together with the nitrogen atom to which they are chemically linked, an heterocycle or an heteroaryl group, substituted with one ($C_1$-$C_6$)alkyl group substituted with one group selected from —$OR_{22}$, —$SR_{23}$, —$S(O)R_{24}$, —$SO_2R_{25}$, —$SO_2NR_{26}R_{27}$, —$OC(O)R_{28}$, —$OCO_2R_{39}$ and —$COR_{42}$; and $R_{22}$ to $R_{28}$, $R_{39}$ and $R_{42}$ are, independently of one another, a hydrogen atom or a ($C_1$-$C_{10}$)alkyl group.

In particular, $R_2$ and $R_3$ form together with the nitrogen atom to which they are chemically linked, an heterocycle or an heteroaryl group, substituted with one ($C_1$-$C_6$)alkyl group optionally substituted with one group selected from —$OR_{22}$ and —$OC(O)R_{28}$; and $R_{22}$ and $R_{28}$ are, independently of one another, a hydrogen atom or a ($C_1$-$C_{10}$)alkyl group.

Notably, $R_2$ and $R_3$ form together with the nitrogen atom to which they are chemically linked, an heterocycle or an heteroaryl group, substituted with one ($C_1$-$C_6$)alkyl group substituted with one group selected from —$OR_{22}$ and —$OC(O)R_{28}$; and $R_{22}$ and $R_{28}$ are, independently of one another, hydrogen atom or a ($C_1$-$C_{10}$)alkyl group.

In the above definitions of $R_2$ and $R_3$, the heterocycle or heteroaryl formed by group $R_2$ and $R_3$ is preferably selected from piperazine and piperidine.

In the above definitions of $R_2$ and $R_3$, the ($C_1$-$C_6$)alkyl is preferably methyl or ethyl.

In the above definitions of $R_2$ and $R_3$, $R_{22}$ and $R_{28}$ are preferably, independently of one another, a hydrogen atom or a ($C_1$-$C_6$)alkyl group; more preferably, $R_{22}$ is a hydrogen atom, and $R_{28}$ is a ($C_1$-$C_6$)alkyl group, notably a methyl group.

In the compound of general formula (I), $R_4$, $R_5$ and $R_6$ represent in particular, independently of one another, hydrogen atom, halo, —CN, —$NO_2$, —NO, —CHO, —$NR_{43}R_{44}$, —$CO_2R_{45}$, —$SO_2R_{47}$, —$SO_2NR_{48}R_{49}$, —$OR_{59}$, —$COR_{60}$, —$SR_{61}$, —$CONR_{62}R_{63}$, —$SO_2(O)R_{66}$, or a group selected from saturated ($C_1$-$C_6$)alkyl, unsaturated ($C_1$-$C_6$)alkyl and aryl, said group being optionally substituted with one or several groups selected from halo, —$CF_3$, —CN and —$SO_2NR_{67}R_{68}$; $R_{43}$ to $R_{45}$, $R_{47}$ to $R_{49}$, $R_{59}$ to $R_{63}$ and $R_{66}$ being as defined above.

Notably, $R_4$, $R_5$ and $R_6$ represents in particular, independently of one another, hydrogen atom, halo or ($C_1$-$C_6$)alkyl, preferably hydrogen atom or ($C_1$-$C_6$)alkyl, more preferably hydrogen atom.

In the definitions of $R_4$, $R_5$ and $R_6$ above, the ($C_1$-$C_6$)alkyl is preferably methyl or ethyl.

In the above definitions of $R_7$ to $R_{68}$, the aryl is preferably phenyl.

In the above definitions of $R_7$ to $R_{68}$, the ($C_1$-$C_{10}$)alkyl is preferably ($C_1$-$C_6$)alkyl, more preferably methyl or ethyl.

In a preferred embodiment, in the compound of general formula (I), X is a sulfur atom.

The stereoisomers of the compound of general formula (I) are also a part of the present invention.

Therefore, the bond represented by the symbol ⌇ in the compound of general formula (I), means that said compound can be in cis or trans configuration, i.e. said compound can be of the following formula (Ia) or (Ib):

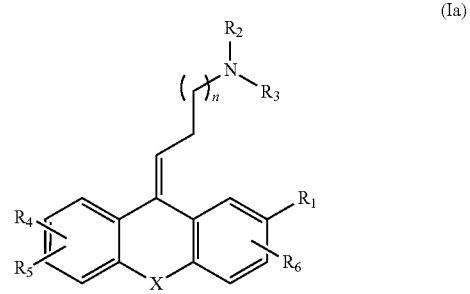
(Ia)

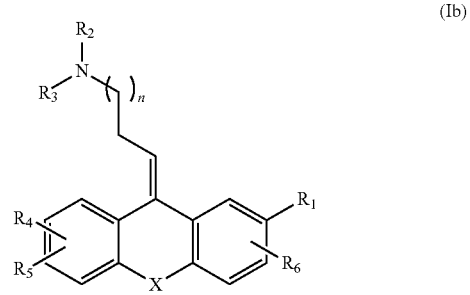
(Ib)

In particular, the compound of general formula (I) is in cis configuration, i.e. the compound is of general formula (Ia).

In a first embodiment, a compound for use according to the invention corresponds to formula (Ia), wherein:

X is a sulfur atom;

$R_1$ is a hydrogen atom, halo, —CN, —CHO, —$NR_7R_8$, —$CO_2R_9$, —$SO_2R_{10}$, —$SO_2NR_{11}R_{12}$, —$COR_{14}$, —$CONR_{16}R_{17}$, —$SO_2(O)R_{18}$ or a group selected from saturated ($C_1$-$C_6$)alkyl and unsaturated ($C_1$-$C_6$)alkyl, said group being optionally substituted with one or several groups selected from halo, —$CF_3$, —CN and —$SO_2NR_{19}R_{20}$; wherein $R_7$ to $R_{12}$, $R_{14}$ and $R_{16}$ to $R_{20}$ each represent, independently of one another, a ($C_1$-$C_6$)alkyl group;

$R_2$ and $R_3$ form together with the nitrogen atom to which they are chemically linked, a piperidine or piperazine group, substituted with one ($C_1$-$C_6$)alkyl group optionally substituted with one or several groups selected from —$OR_{22}$, —$SR_{23}$, —$S(O)R_{24}$, —$SO_2R_{25}$, —$SO_2NR_{26}R_{27}$, —$OC(O)R_{28}$, —$NR_{29}COR_{30}$, —$NR_{31}CONR_{32}R_{33}$, —$NR_{34}C(O)OR_{35}$, —$CONR_{37}R_{38}$, —$OCO_2R_{39}$, —$OCONR_{40}R_{41}$, —$COR_{42}$, —$NO_2$ and —CN; wherein $R_{22}$ to $R_{35}$ and $R_{37}$ to $R_{42}$ each represent, independently of one another, a ($C_1$-$C_6$)alkyl group; and $R_4$, $R_5$ and $R_6$ are, independently of one another, a hydrogen atom, halo or a ($C_1$-$C_6$)alkyl group.

In a second embodiment, a compound for use according to the invention corresponds to formula (Ia), wherein:

X is a sulfur atom;

$R_1$ is —Cl, —F, —CN, —$SO_2NR_{11}R_{12}$ or —$CF_3$; wherein $R_{11}$ and $R_{12}$ each represent, independently of one another, a ($C_1$-$C_6$)alkyl group;

$R_2$ and $R_3$ form together with the nitrogen atom to which they are chemically linked, a piperazine group, substituted with one ($C_1$-$C_6$)alkyl group optionally substituted with one group selected from —$OR_{22}$ and —OC(O)$R_{28}$; wherein $R_{22}$ and $R_{28}$ are, independently of one another, a hydrogen atom or a ($C_1$-$C_6$)alkyl group; and $R_4$, $R_5$ and $R_6$ each represent a hydrogen atom.

Preferably, the compound of general formula (I) can be selected from Zuclopenthixol (referred to as ZU) and derivative compounds ZU1, ZU2, ZU3 and ZU5, described in the experimental part below, and the pharmaceutically acceptable salts and solvates thereof. More preferably, the compound of general formula (I) is ZU, or a pharmaceutically acceptable salt and solvate thereof.

As shown in the experimental section, the compounds of general formula (I) are efficient in:

selectively inhibiting in vitro cell proliferation (2D and 3D culture systems) of several ErbB2-dependent cancer cell lines, whereas no inhibition is noticed for ErbB2 in-dependent cancer cell lines or non-cancerous cells, inhibiting in vivo the growth of human tumors overexpressing ErbB2 in murine orthotopic xenograft models, inhibiting in vitro the growth of human cells expressing ErbB2 mutated forms characterized by a resistance to ErbB2 dependent cancer treatments and/or implicated in tumors aggressiveness.

specifically blocking the ligand-independent activation of ErbB2 and do not interfere with physiological ErbB2 activation in heterodimers with the other ErbB family members.

Consequently, preferably, the present invention is directed to the compound of general formula (I) as defined above for use in the treatment of ErbB2-dependent cancers.

As mentioned above said ErbB2-dependent cancers comprise cancers for which an amplification of ErbB2 gene or an activated form of the protein is detected in cancerous cells from the patient.

In particular, the present invention is also directed to the compound of general formula (I) as defined above for use in the treatment of an ErbB2-dependent cancer resistant to a ErbB2 dependent cancer specific treatment.

More particularly, the present invention is also directed to the compound of general formula (I) as defined above for use in the treatment of an ErbB2-dependent cancer resistant to immunotherapy targeting the external domain of ErbB2. Even more particularly, said ErbB2 dependent cancer are resistant to trastuzumab and/or pertuzumab based therapies.

In particular, the present invention is also directed to the compound of general formula (I) as defined above for use in the treatment of an ErbB2-dependent cancer, wherein the deregulation of ErbB2 gene corresponds to activating mutations V777L or V842I.

In another aspect, the present invention is directed to the compound of general formula (I) as defined above for use in the treatment of ErbB2-dependent cancers resistant to inhibitor of tyrosine kinase therapies.

Compounds of general formula (I), in particular commercially available ZU, ZU1 and ZU2, are known in the art to cross blood brain barrier. This makes the use of these compounds of an even more particular interest in the treatment or prevention of ErbB2 positive brain metastasis, for which therapeutic options are highly limited because of the restricted permeability of the blood brain barrier to most of the circulating compounds.

The present invention is also directed to the compound of general formula (I) as defined above for use in the prevention and/or treatment of ErbB2-dependent cancers metastasis, preferably for use in the prevention of ErbB2-dependent cancers metastasis, in particular brain metastasis.

The present invention also relates to a method for the treatment and/or the prevention of ErbB2-dependent cancers comprising the administration to a person in need thereof of an effective dose of a compound of formula (I) as defined above. In particular the present invention also relates to a method for the treatment of ErbB2-dependent cancers and/or for the prevention and/or treatment of ErbB2-dependent cancers metastasis, preferably for the prevention of ErbB2-dependent cancers metastasis, in particular brain metastasis, comprising the administration to a person in need thereof of an effective dose of a compound of formula (I) as defined above.

The present invention also relates to the use of a compound of formula (I) as defined above, for the manufacture of a drug for the treatment and/or the prevention of ErbB2-dependent cancers. In particular the present invention also relates to the use of a compound of formula (I) as defined above, for the manufacture of a drug for the treatment of ErbB2-dependent cancers and/or for the prevention and/or treatment of ErbB2-dependent cancers metastasis, preferably for the prevention of ErbB2-dependent cancers metastasis, in particular brain metastasis.

The ErbB2-dependent cancers may be particularly lung cancer, in particular non-small-cell lung cancer, ovarian cancer, stomach cancer, bladder cancer, uterine cancer, in particular uterine serous cancer, pancreas cancer, liver cancer, kidney cancer, gastroeosophageal cancer, gastric cancer, colorectal cancer, female genital tract cancer, endometrial cancer, anal cancer, breast cancer or neurofibroma. The ErbB2-dependent cancers may be more particularly colorectal, anal cancers, neurofibroma, endometrial, gastroesophageal, gastric, ovarian, pancreatic and breast cancers, even more particularly gastric, ovarian and breast cancers, notably breast cancer.

Ebselen Oxide Derivatives

According to a particular embodiment of the second objet of the present invention, in the compound of the general formula (II), $R'_1$ and $R'_2$ are, independently of one another, hydrogen atom, halo, $(C_1-C_6)$alkyl, CN or $CF_3$.

In particular, $R'_1$ is a hydrogen atom and $R'_2$ is hydrogen atom, halo, $(C_1-C_6)$alkyl, CN or $CF_3$, preferably hydrogen atom, halo or $(C_1-C_6)$alkyl.

In the above definitions of $R'_1$ and $R'_2$, the $(C_1-C_6)$alkyl is preferably methyl or ethyl.

In a preferred embodiment, in the compound of the general formula (II), $R'_3$ is hydrogen atom, halo, $(C_1-C_6)$alkyl, $OR'_{12}$, $NR'_{13}R'_{14}$, $SR'_{15}$, $S(O)R'_{16}$, $SO_2R'_{17}$, $CO_2R'_{28}$, $COR'_{34}$, nitro $(NO_2)$, cyano (CN); $R'_{12}$ to $R'_{17}$, $R'_{28}$ and $R'_{34}$ being as defined above, preferably $R'_{12}$ to $R'_{17}$, $R'_{28}$ and $R'_{34}$ are, independently of one another, a hydrogen atom or a $(C_1-C_6)$alkyl group.

$R'_3$ is notably H, halo or $(C_1-C_6)$alkyl, preferably H.

According to a particular embodiment, in the compound of the general formula (II), Y is Se=O.

Therefore, said compound is of the following formula (IIa):

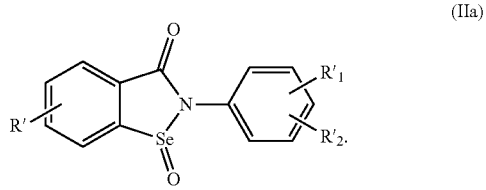

(IIa)

In a first embodiment, a compound for use according to the invention corresponds to formula (IIa), wherein:
$R'_1$ and $R'_2$ are, independently of one another, H, halo, $(C_1-C_6)$alkyl, CN, $CF_3$, CHO, $CO_2R'_4$, $SO_2R'_5$, $SO_2NR'_6R'_7$, $COR'_8$, $CONR'_9R'_{10}$ or $SO_2OR'_{11}$;
$R'_3$ is H, halo, $(C_1-C_6)$alkyl, $OR'_{12}$, $NR'_{13}R'_{14}$, $SR'_{15}$, $S(O)R'_{16}$, $SO_2R'_{17}$, $SO_2NR'_{18}R'_{19}$, $OCOR'_{20}$, $NR'_{21}COR'_{22}$, $NR'_{23}CONR'_{24}R'_{25}$, $NR'_{26}C(O)OR'_{27}$, $CO_2R'_{28}$, $CONR'_{29}R'_{30}$, $OCO_2R'_{31}$, $OCONR'_{32}R'_{33}$, $COR'_{34}$, nitro $(NO_2)$ or cyano (CN); and
$R'_4$ to $R'_{34}$ are, independently of one another, H or a $(C_1-C_6)$alkyl, aryl or aryl$(C_1-C_6)$alkyl group, said group being optionally substituted with one or several halo.

In a second embodiment, a compound for use according to the invention corresponds to formula (IIa), wherein:
$R'_1$ and $R'_2$ are, independently of one another, hydrogen atom, halo, $(C_1-C_6)$alkyl, CN or $CF_3$; and
$R'_3$ is hydrogen atom, halo, $(C_1-C_6)$alkyl, $OR'_{12}$, $NR'_{13}R'_{14}$, $SR'_{15}$, $S(O)R'_{16}$, $SO_2R'_{17}$, $CO_2R'_{28}$, $COR'_{34}$, nitro $(NO_2)$, cyano (CN); wherein $R'_{12}$ to $R'_{17}$, $R'_{28}$ and $R'_{34}$ are, independently of one another, a hydrogen atom or a $(C_1-C_6)$alkyl group.

In a third embodiment, a compound for use according to the invention corresponds to formula (IIa), wherein:
$R'_1$ is a hydrogen atom and $R'_2$ is a hydrogen atom, halo or $(C_1-C_6)$alkyl; and
$R'_3$ is H, halo or $(C_1-C_6)$alkyl, preferably H.

The compound of general formula (II) can particularly be selected from Ebselen oxide (referred to as EB1) and derivative compounds EB2 and EB3, described in the experimental part below and the pharmaceutically acceptable salts and solvates thereof.

In a particular embodiment, the compound of general formula (IIa) is Ebselen oxide (referred to as EB1), or a pharmaceutically acceptable salt and/or solvate thereof.

As Shown in the Experimental Section, the Compounds of General Formula (IIa) are Efficient in:
- selectively inhibiting in vitro cell proliferation (2D and 3D culture systems) of several ErbB2-dependent cancer cell lines, whereas no inhibition is noticed for ErbB2 non-dependent cancer cell lines or non-cancerous cells,
- inhibiting in vivo the growth of human tumors overexpressing ErbB2 in murine orthotopic xenograft models,
- inhibiting in vitro the growth of human cells expressing ErbB2 mutated forms characterized by a resistance to ErbB2 dependent cancer treatments and/or implicated in tumors aggressiveness.
- specifically blocking the ligand-independent activation of ErbB2 and do not interfere with physiological ErbB2 activation in heterodimers with the other ErbB family members.

Accordingly, in one particular embodiment, the present invention is directed to the compound of general formula (II) as defined above for use in the treatment of ErbB2-dependent cancers.

According to another particular embodiment, the present invention is directed to the compound of general formula (IIa) as defined above for use in the treatment of ErbB2-dependent cancers.

As mentioned above said ErbB2-dependent cancers comprise cancers for which an amplification of ErbB2 gene or an activated form of the protein is detected in cancerous cells from the patient.

In particular, the present invention is also directed to the compound of general formula (II), preferably formula (IIa) as defined above, for use in the treatment of an ErbB2-dependent cancer resistant to a ErbB2 dependent cancer specific treatment.

More particularly, the present invention is also directed to the compound of general formula (II), preferably formula (II) as defined above, for use in the treatment of an ErbB2 dependent cancer resistant to immunotherapy targeting the external domain of ErbB2. Even more particularly, said ErbB2 dependent cancer are resistant to trastuzumab and/or pertuzumab based therapies.

In particular, the present invention is also directed to the compound of general formula (II), preferably formula (IIa) as defined above, for use in the treatment of an ErbB2-dependent cancer, wherein the deregulation of ErbB2 gene corresponds to activating mutations V777L or V842I.

In another aspect, the present invention is directed to the compound of general formula (II), preferably formula (IIa) as defined above, for use in the treatment of ErbB2-dependent cancers resistant to inhibitor of tyrosine kinase therapies.

The present invention is also directed to the compound of general formula (II) as defined above for use in the prevention and/or treatment of ErbB2-dependent cancers metastasis, preferably for use in the prevention of ErbB2-dependent cancers metastasis, in particular brain metastasis.

The present invention is also directed to the compound of general formula (IIa) as defined above for use in the prevention and/or treatment of ErbB2-dependent cancers metastasis, preferably for use in the prevention of ErbB2-dependent cancers metastasis, in particular brain metastasis.

The present invention also relates to a method for the treatment and/or the prevention of ErbB2-dependent cancers comprising the administration to a person in need thereof of an effective dose of a compound of formula (II) as defined above. In particular the present invention also relates to a method for the treatment of ErbB2-dependent cancers, and/or for the prevention and/or treatment of ErbB2-dependent cancers metastasis, preferably for the prevention of ErbB2-dependent cancers metastasis, in particular brain metastasis, comprising the administration to a person in need thereof of an effective dose of a compound of formula (II) as defined above.

The present invention also relates to a method for the treatment and/or the prevention of ErbB2-dependent cancers comprising the administration to a person in need thereof of an effective dose of a compound of formula (IIa) as defined above. In particular the present invention also relates to a method for the treatment of ErbB2-dependent cancers and/or for the prevention and/or treatment of ErbB2-dependent cancers metastasis, preferably for the prevention of ErbB2-dependent cancers metastasis, in particular brain metastasis, comprising the administration to a person in need thereof of an effective dose of a compound of formula (IIa) as defined above.

The present invention also relates to the use of a compound of formula (II) as defined above, for the manufacture of a drug for the treatment and/or the prevention of ErbB2-dependent cancers. In particular the present invention also relates to the use of a compound of formula (II) as defined above, for the manufacture of a drug for the treatment of ErbB2-dependent cancers and/or for the prevention and/or treatment of ErbB2-dependent cancers metastasis, preferably for the prevention of ErbB2-dependent cancers metastasis, in particular brain metastasis.

The present invention also relates to the use of a compound of formula (IIa) as defined above, for the manufacture of a drug for the treatment and/or the prevention of ErbB2-dependent cancers. In particular the present invention also relates to the use of a compound of formula (IIa) as defined above, for the manufacture of a drug for the treatment of ErbB2-dependent cancers and/or for the prevention and/or treatment of ErbB2-dependent cancers metastasis, preferably for the prevention of ErbB2-dependent cancers metastasis, in particular brain metastasis.

The ErbB2-dependent cancers may be particularly lung cancer, in particular non-small-cell lung cancer, ovarian cancer, stomach cancer, bladder cancer, uterine cancer, in particular uterine serous cancer, pancreas cancer, liver cancer, kidney cancer, gastroeosophageal cancer, gastric cancer, colorectal cancer, female genital tract cancer, endometrial cancer, anal cancer, breast cancer or neurofibroma. The ErbB2-dependent cancers may be more particularly colorectal, anal cancers, neurofibroma, endometrial, gastroesophageal, gastric, ovarian, pancreatic and breast cancers, even more particularly breast cancer.

Pharmaceutical Composition

The present invention also relates to a pharmaceutical composition comprising at least one compound of formula (I) or of formula (II) as defined above and at least one pharmaceutically acceptable excipient, for use in the treatment and/or in the prevention of ErbB2-dependent cancers.

The present invention also relates to a pharmaceutical composition comprising at least one compound of formula (IIa) as defined above and at least one pharmaceutically acceptable excipient, for use in the treatment and/or in the prevention of ErbB2-dependent cancers.

The pharmaceutical compositions according to the invention may be formulated notably for oral administration or for injection, preferably for intramuscular injection, wherein said compositions are intended for mammals, including humans.

The pharmaceutical composition can be administered orally by means of tablets and gelatin capsules.

When a solid composition is prepared in the form of tablets, the main active ingredient is mixed with a pharmaceutical vehicle such as gelatin, starch, lactose, magnesium stearate, talc, gum arabic and the like. The tablets may be coated with sucrose or with other suitable materials, or they may be treated in such a way that they have a prolonged or delayed activity and they continuously release a predetermined amount of active principle.

A preparation in gelatin capsules is obtained by mixing the active ingredient with a diluent and pouring the mixture obtained into soft or hard gelatin capsules.

For administration by injection, aqueous suspensions, isotonic saline solutions or sterile and injectable solutions which contain pharmacologically compatible dispersing agents and/or wetting agents are used.

The active ingredient may be administered in unit dosage forms of administration, in mixture with standard pharmaceutical carriers, to animals or to humans. The compounds of the invention as active ingredients may be used in doses ranging between 0.01 mg and 1000 mg per day, given in a single dose once per day or administered in several doses throughout the day, for example twice a day in equal doses. The dose administered per day advantageously is between 5 mg and 500 mg, even more advantageously between 10 mg and 200 mg. It may be necessary to use doses outside these ranges as determined by the person skilled in the art.

The active ingredient may be administered intramuscularly. With this formulation, the dose administered advantageously is between 50 mg and 800 mg every one to six weeks, more advantageously between 100 mg and 600 mg, every two to four weeks.

The pharmaceutical compositions according to the invention may further comprise at least one other active ingredient, such as an anticancer agent.

The present invention relates also to a pharmaceutical composition comprising:
(i) at least one compound of formula (I) and/or of formula (II) as defined above, and
(ii) at least one other active ingredient, such as an anticancer agent,
as a combination product for simultaneous, separate or sequential use.

The Present Invention Relates also to a Pharmaceutical Composition Comprising:
(i) at least one compound of formula (IIa) as defined above, and
(ii) at least one other active ingredient, such as an anticancer agent, as a combination product for simultaneous, separate or sequential use.

An anticancer agent according to the invention refers to any agent of use in cancer treatment, and particularly, to any chemotherapeutic agent, as well as to any antibody directed to extracellular part of ErbB2 or any inhibitor of tyrosine kinase based therapy.

According to one particular embodiment, the present invention is directed to the pharmaceutical composition as defined above for use in the treatment of ErbB2-dependent cancers.

The present invention is also directed to the pharmaceutical composition as defined above for use in the prevention and/or treatment of ErbB2-dependent cancers metastasis, preferably for use in the prevention of ErbB2-dependent cancers metastasis, in particular brain metastasis.

The present invention also relates to a method for the treatment and/or the prevention of ErbB2-dependent cancers comprising the administration to a person in need thereof of an effective dose of the pharmaceutical composition as defined above. In particular the present invention also relates to a method for the treatment of ErbB2-dependent cancers and/or for the prevention and/or treatment of ErbB2-dependent cancers metastasis, preferably for the prevention of ErbB2-dependent cancers metastasis, in particular brain metastasis, comprising the administration to a person in need thereof of an effective dose of the pharmaceutical composition as defined above.

The present invention also relates to the use of the pharmaceutical composition as defined above, for the manufacture of a drug for the treatment and/or the prevention of ErbB2-dependent cancers. In particular the present invention also relates to the use of the pharmaceutical composition as defined above, for the manufacture of a drug for the treatment of ErbB2-dependent cancers and/or for the prevention and/or treatment of ErbB2-dependent cancers metastasis, preferably for the prevention of ErbB2-dependent cancers metastasis, in particular brain metastasis.

The ErbB2-dependent cancers may be particularly lung cancer, in particular non-small-cell lung cancer, ovarian cancer, stomach cancer, bladder cancer, uterine cancer, in particular uterine serous cancer, pancreas cancer, liver cancer, kidney cancer, gastroeosophageal cancer, gastric cancer, colorectal cancer, female genital tract cancer, endometrial cancer, anal cancer, breast cancer or neurofibroma. The ErbB2-dependent cancers may be more particularly colorectal, anal cancers, neurofibroma, endometrial, gastroesophageal, gastric, ovarian, pancreatic and breast cancers, even more particularly gastric, ovarian and breast cancers, notably breast cancer.

The examples which follow illustrate the invention without limiting its scope in any way.

Figure 13A:
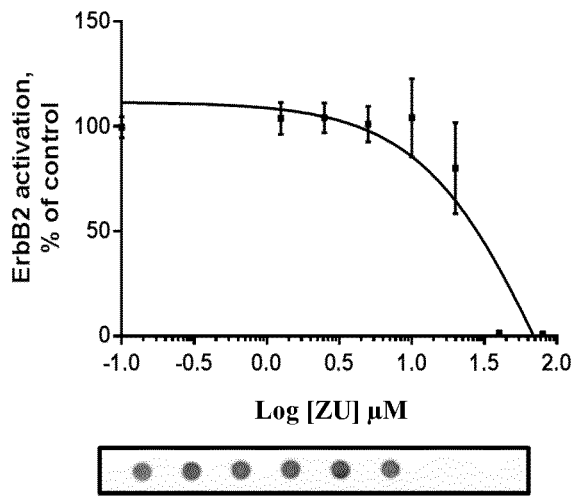
Figure 13B:
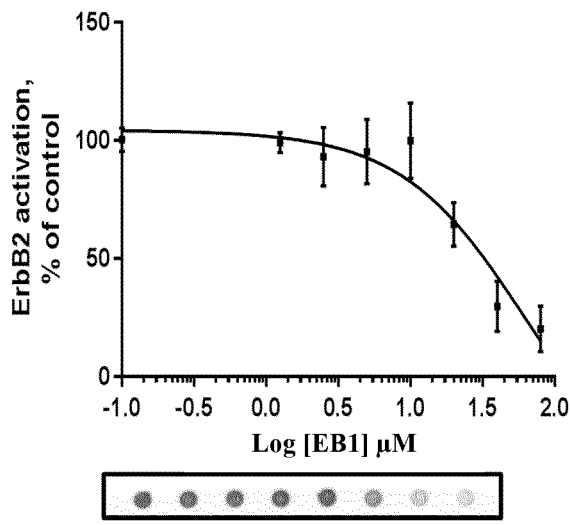
Figure 13C:
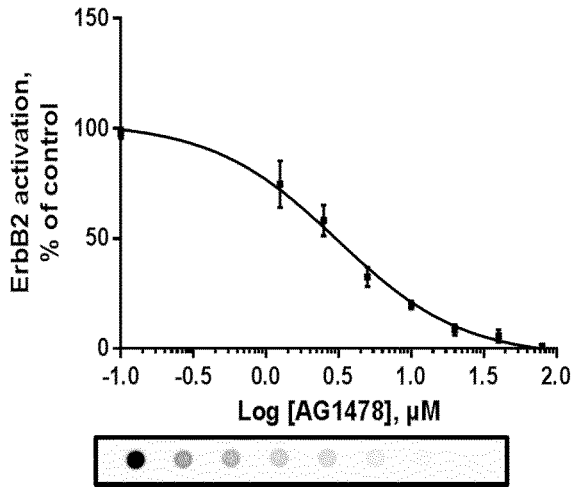

FIG. 13. represents the effect of (A) compound ZU, (B) compound EB1 and (C) AG1478 on ErbB2 activation measured by dot blot analysis of ErbB2 phosphorylation in N87 cells.

Figure 14A:
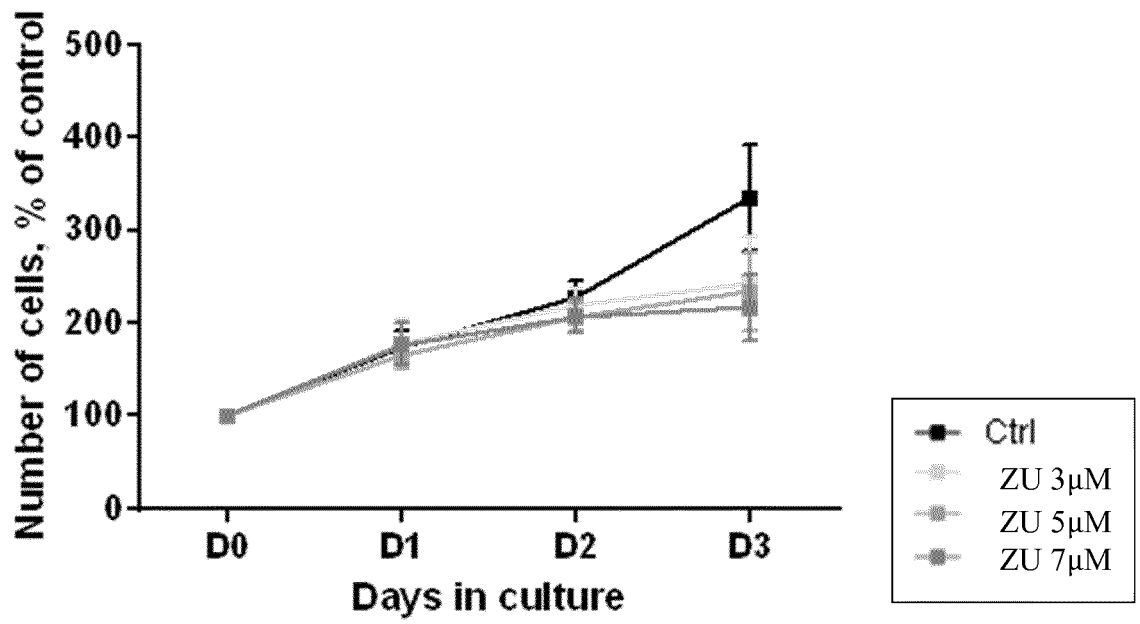
Figure 14B:
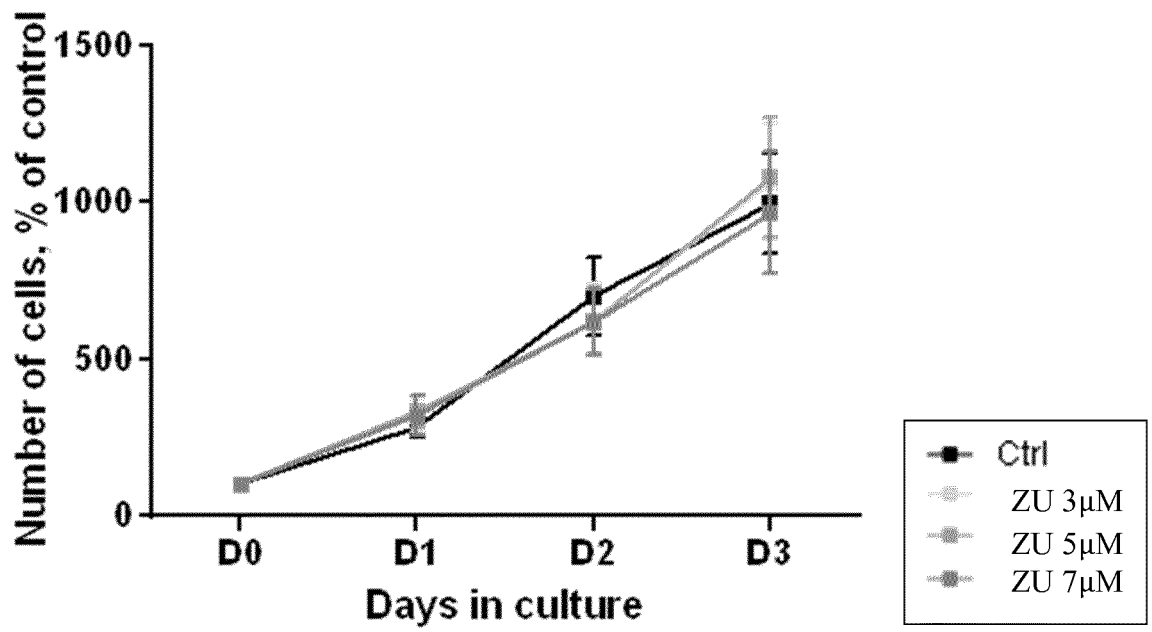

FIG. 14. represents the specific inhibition of the ErbB2-dependent cell proliferation of (A) N87 by ZU measured by MTT assays as compared to an absence of inhibition of the proliferation of the ErbB2-independent (B) MDA-MB-231 cell line.

Figure 15A:
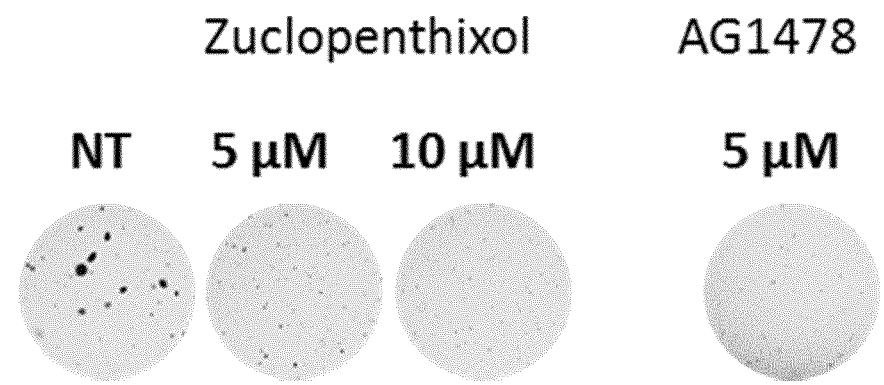
Figure 15B:
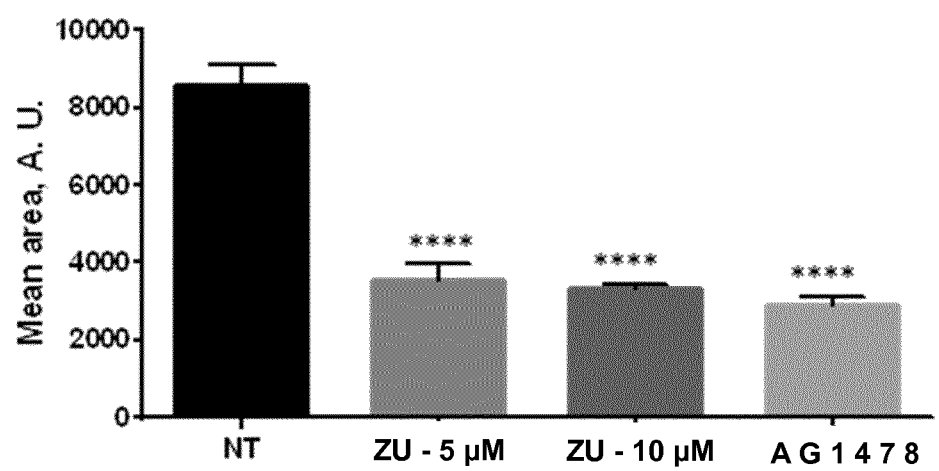

FIG. 15. represents the inhibition of the anchorage-independent growth of N87 (A-B) by compound ZU measured in soft agar assays. AG1478, a tyrosine kinase inhibitor of the EGFR family members was used as a control. (A) displays representative photographs of the colonies; (B) shows the colony mean area measured for each treatment condition (One way ANOVA: F(3, 6)=170.9, Dunnet's Post Hoc Test, ****p<0.0001)

Figure 16A:
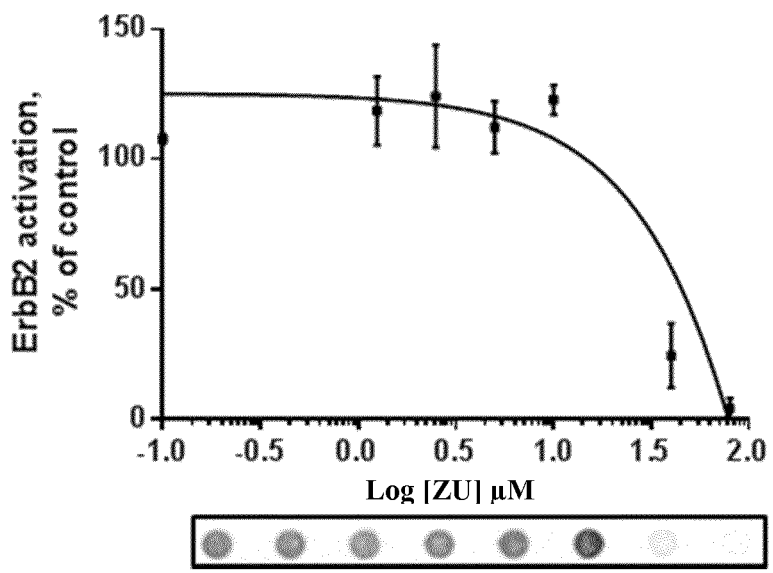
Figure 16B:
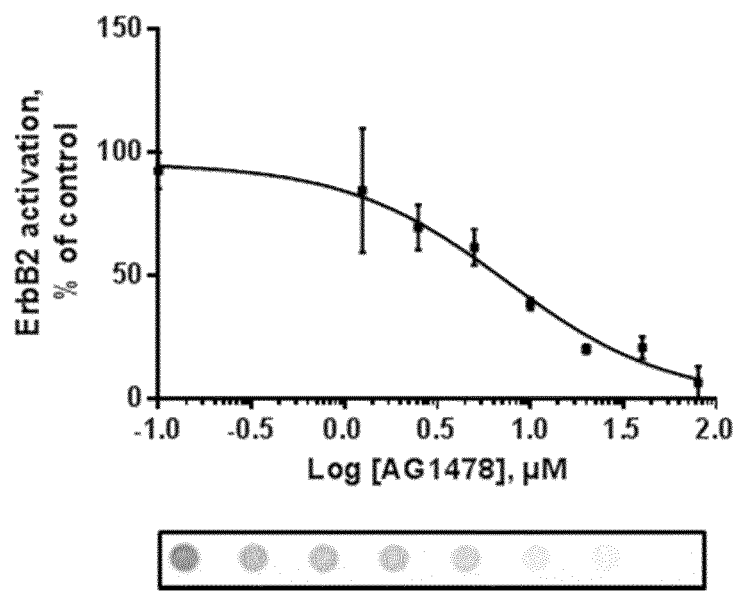

FIG. 16. represents the effect of (A) compound ZU and (B) AG1478 on ErbB2 activation measured by dot blot analysis of ErbB2 phosphorylation in SKOV3 cells.

Figure 17A:
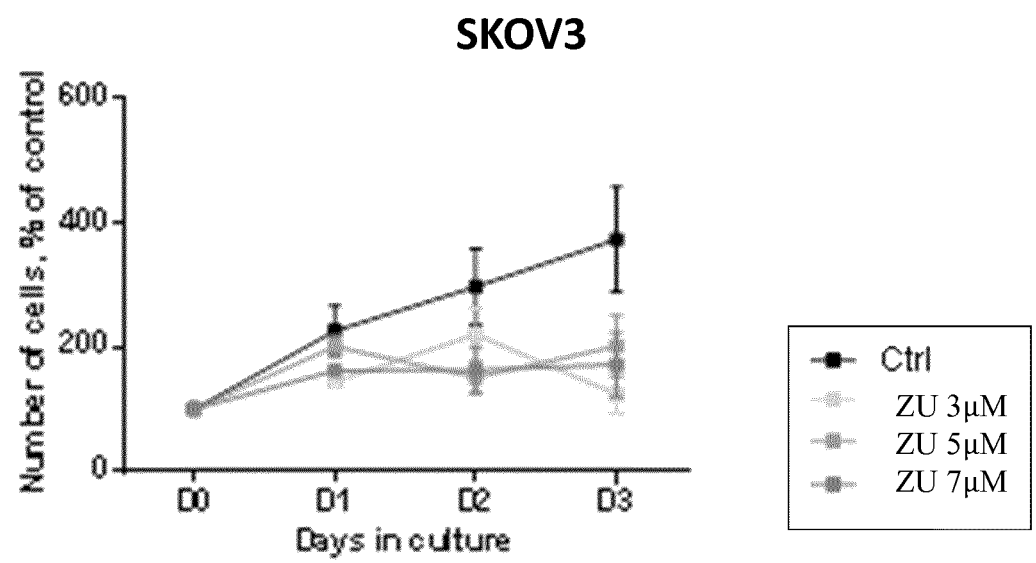
Figure 17B:
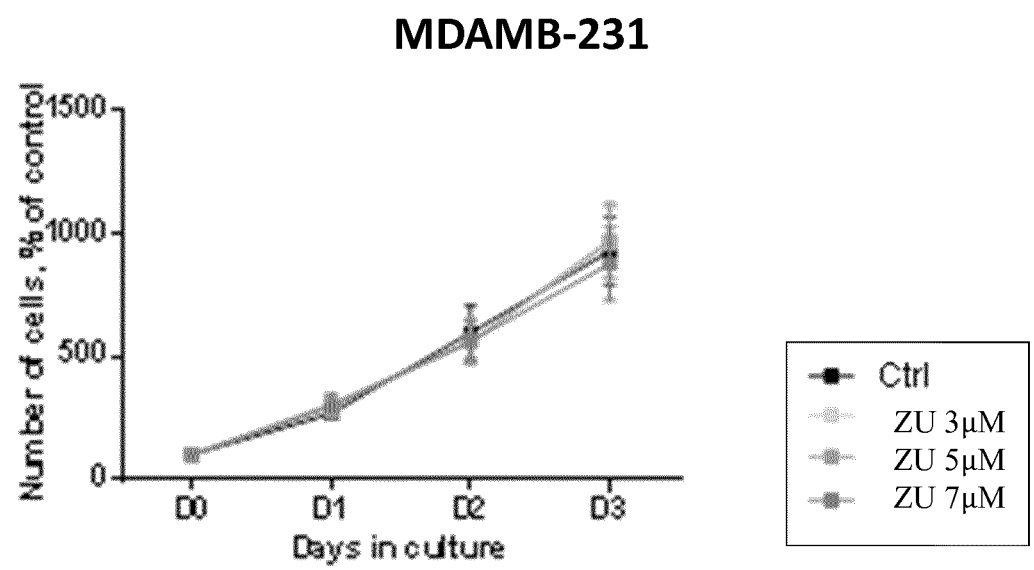

FIG. 17. represents the specific inhibition of the ErbB2-dependent cell proliferation of (A) SKOV3 by ZU measured by MTT assays as compared to an absence of inhibition of the proliferation of the ErbB2-independent (B) MDA-MB-231 cell line.

Figure 18A:
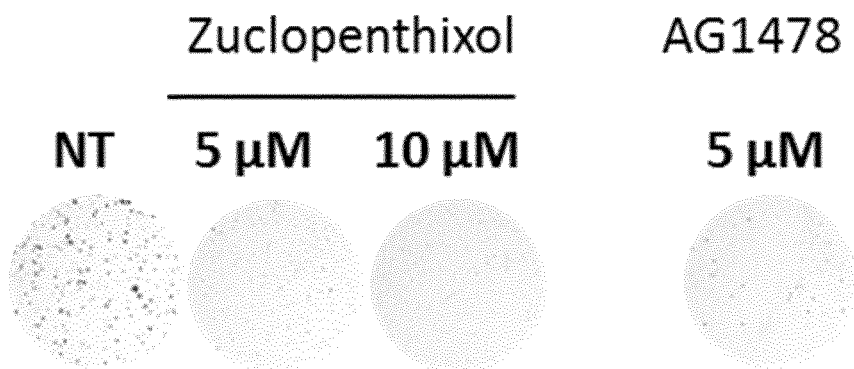
Figure 18B:
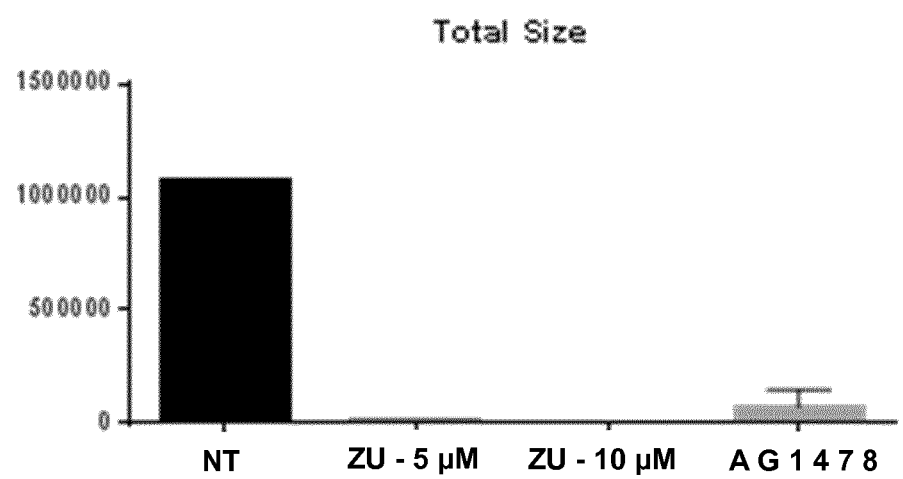

FIG. 18. represents the inhibition of the anchorage-independent growth of SKOV3 (A-B) by compound ZU measured in soft agar assays. AG1478, a tyrosine kinase inhibitor of the EGFR family members was used as a control. (A) displays representative photographs of the colonies; (B) shows the colony mean area measured for each treatment condition.

Figure 19A:
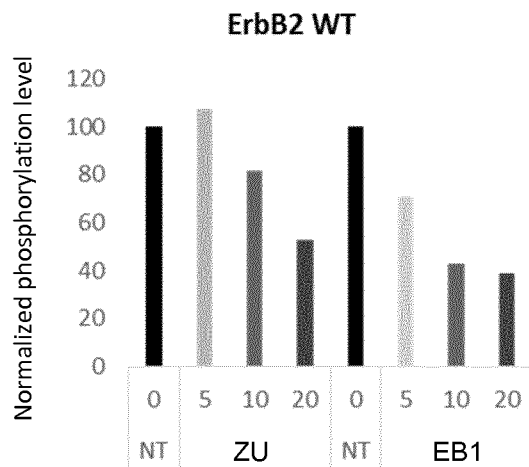
Figure 19B:
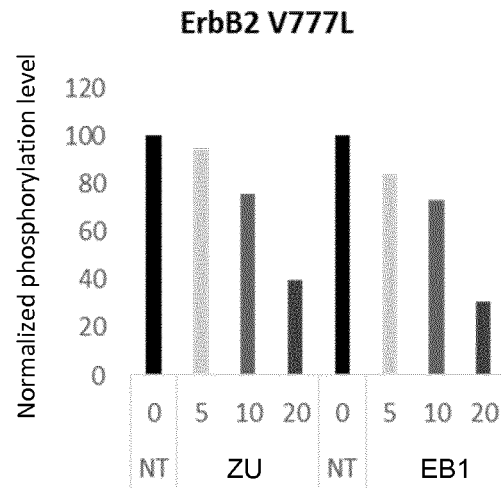
Figure 19C:
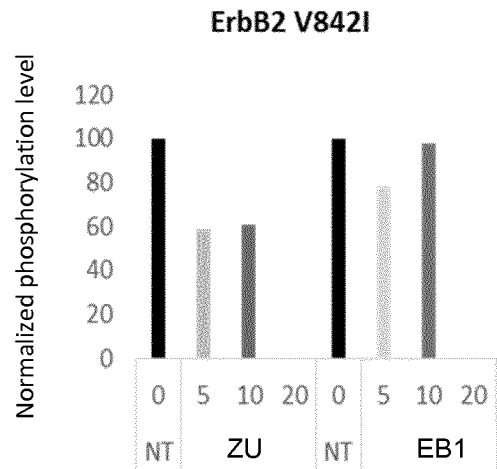
Figure 20A:
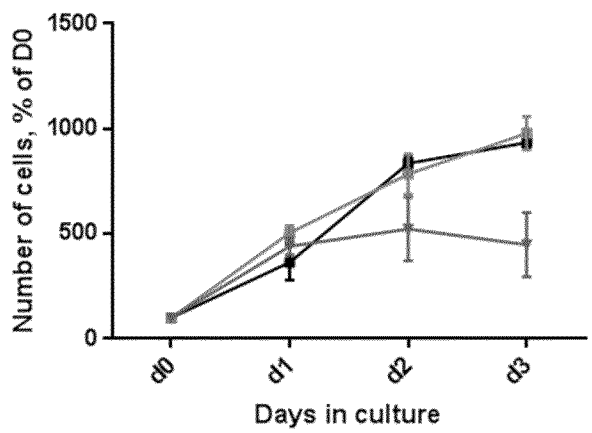
Figure 20B:
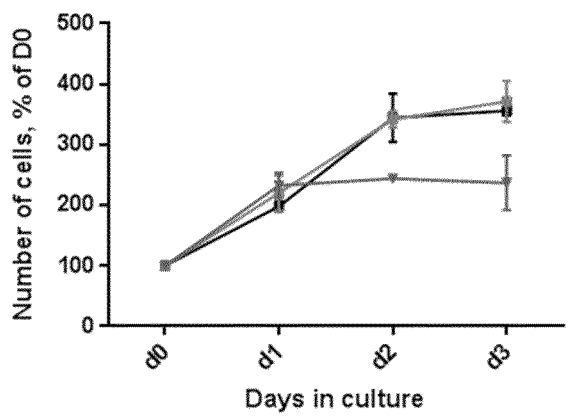
Figure 20C:
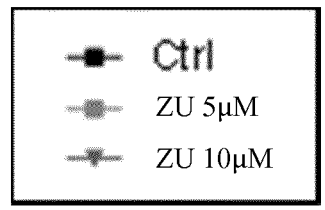
Figure 20C:
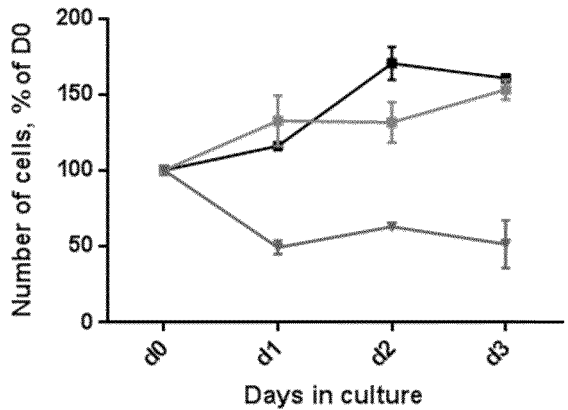
Figure 20D:
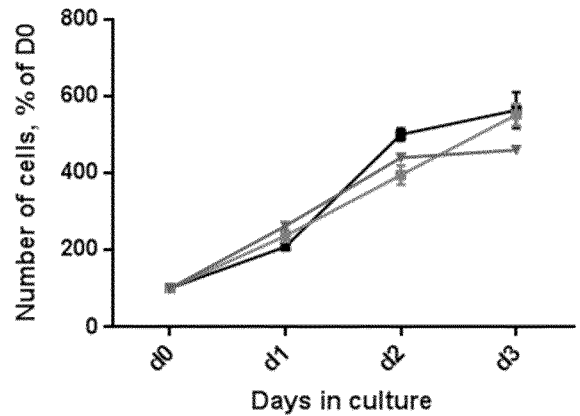
Figure 21A:
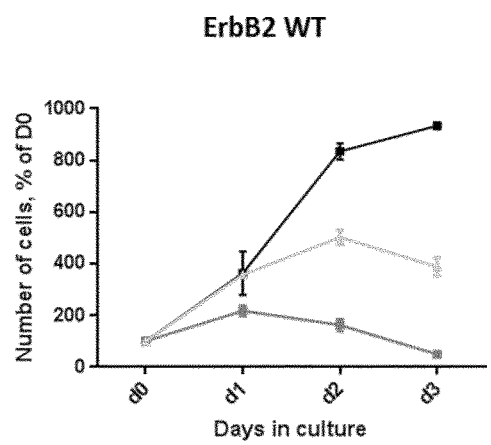
Figure 21B:
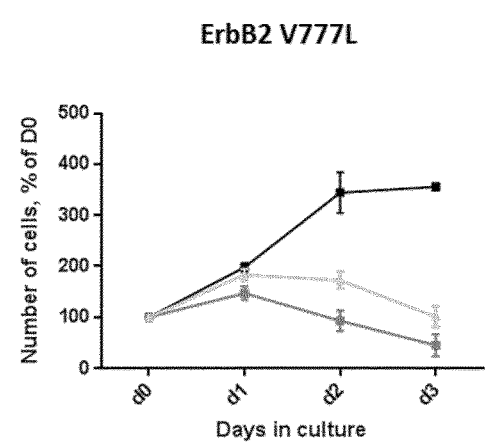
Figure 21C:
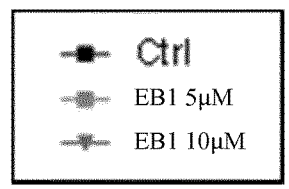
Figure 21C:
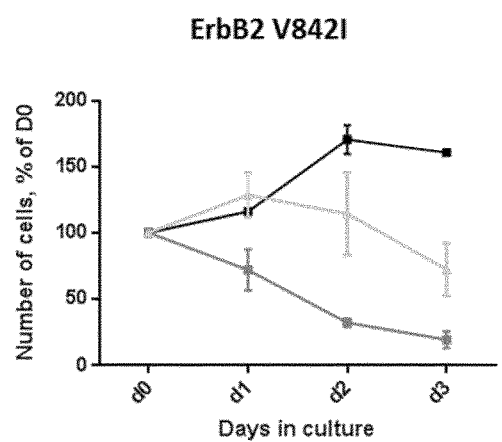
Figure 21D:
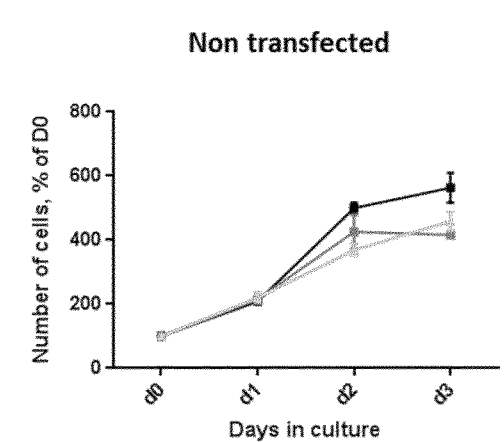

FIG. 19. represents the effect of compound ZU, compound EB1 on the activation of (A) WT, (B) V777L and (C) V842I ErbB2 measured by western blot analysis of ErbB2 phosphorylation.

FIG. 20. represents the specific inhibition of the (A) WT, (B) V777L and (C) V842I ErbB2-dependent cell proliferation by ZU measured by MTT assays as compared to an absence of inhibition of the proliferation of the ErbB2-independent (D) non transfected cells.

FIG. 21. represents the specific inhibition of the (A) WT, (B) V777L and (C) V842I ErbB2-dependent cell proliferation by EB1 measured by MTT assays as compared to an absence of inhibition of the proliferation of the ErbB2-independent (D) non transfected cells

EXAMPLES

The Following Abbreviations have been used in the Following Examples.
a.a.: Amino acid
AdoMet: S-Adenosyl-L-methionine
ATP: Adenosine triphosphate
BSA: Bovine Serum Albumin
CMV: Cytomegalovirus
DCM: Dichloromethane
DIAD: Diisopropyl azodicarboxylate
DiPEA: N,N-Diisopropylethylamine
DMF: Dimethylformamide
DMSO: Dimethylsulfoxide
DNA: Deoxyribonucleic acid
EDTA: Ethylenediaminetetraacetic acid
ESI: Electrospray ionisation
HEPES: 4-(2-Hydroxyethyl)-1-piperazineethanesulfonic acid
HPLC: High Performance Liquid Chromatography
HRMS: High Resolution Mass Spectrometry
MW: Microwave
ND: Not determined
NMR: Nuclear Magnetic Resonance
PBS: Phosphate buffered saline
PBST: Phosphate buffered saline+Tween-20
RPMI: Roswell Park Memorial Institute medium
RT: Room temperature
SAH: S-Adenosyl-L-homocysteine
SAM: S-Adenosyl-L-methionine
TEA: Triethylamine
TFA: Trifluoroacetic acid
Tris: Tris(hydroxymethyl)aminomethane I. Synthesis of the Compounds According to the Invention Example 1: Zuclopentixol Derivatives Preparation of ZU3

9-(3-(4-(2-hydroxyethyl)piperazinyl)propylidene)-thioxanthene

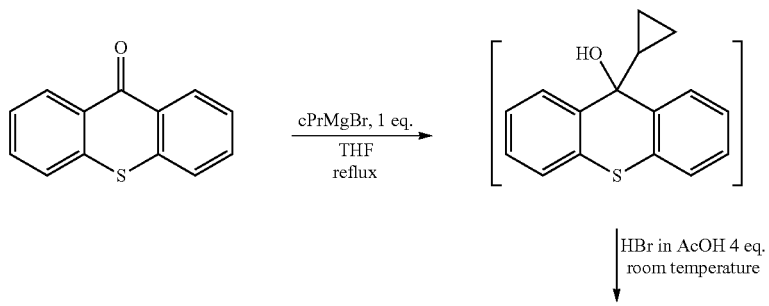

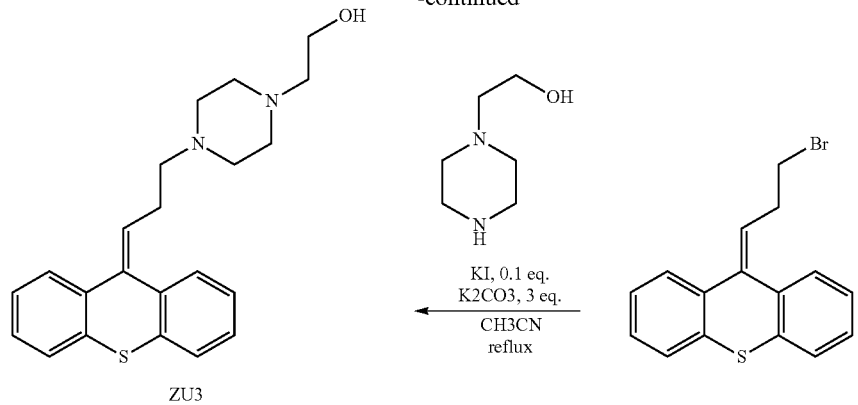

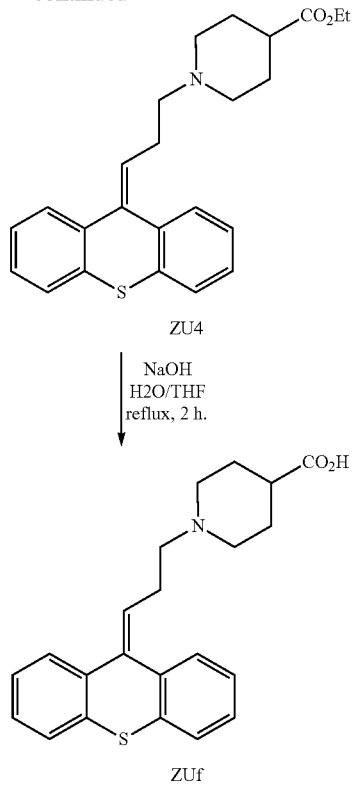

To a solution of 9-oxothioxanthene (1.0 equiv.) in THF at reflux were added a solution of cyclopropylmagnesium bromide in THF (1.0 equiv.) and stirred during 2 hours. The mixture was cooled down at room temperature and a solution of hydrogen bromide in acetic acid (4 eq.) was added and stirred at room temperature. The reaction mixture was concentrated in vacuo and purified by silica gel column chromatography to obtain 9-(3bromopropylidene)thioxanthene in 30% yield.

Then, to a solution of 9-(3bromopropylidene)thioxanthene in acetonitrile at reflux was added N-(2-hydroxyethyl)piperazine (1.5 eq.), potassium iodide (0.1 eq.) and potassium carbonate (3 eq.). The mixture was stirred at reflux then concentrated in vacuo and purified by silica gel column chromatography to afford ZU3 with 98% purity (HPLC). HPLC analysis (BEH C18 type, mobile phase: H2O/acetonitrile (HCOOH 0.1%)): $t_R$=1.68 min.

Preparation of ZUf 1-(3-(9H-thioxanthen-9-ylidene)propyl)piperidine-4-carboxylic acid, ZU4 (9-(3-(4-(ethylacetate)piperidine)propylidene)-thioxanthene

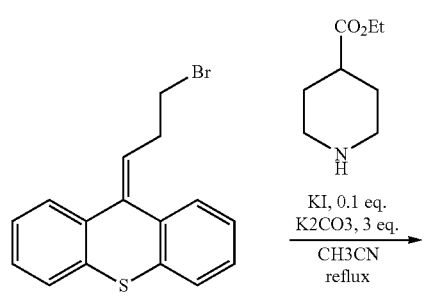

To a solution of 9-(3-bromopropylidene)thioxanthene in acetonitrile at reflux was added N-ethylacetate piperidine (1.5 eq.), potassium iodide (0.1 eq.) and potassium carbonate (3 eq.). The mixture was stirred at reflux then concentrated in vacuo and purified by silica gel column chromatography to afford ZU4 as a brown oil with a purity of 97% in HPLC analysis HPLC analysis (BEH C18 type, mobile phase: H2O/acetonitrile (HCOOH 0.1%)): $t_R$=2.07 min.

The compound ZU4 was stirred during 2 hours at reflux in a mixture of THF and a solution of NaOH in water. After phase separation, the aqueous layer was extracted twice by diethyl ether. The global organic layer was, then, washed by a saturated solution of NaCl, dried over MgSO4, filtered and concentrated in vacuo to afford ZUf HPLC analysis (BEH C18 type, mobile phase: H2O/acetonitrile (HCOOH 0.1%)): $t_R$=2.24 min.

Preparation of ZU5

(Z)-2-(4-(3-(2-chloro-9H-thioxanthen-9-ylidene)propyl)piperazin-1-yl)ethylacetate

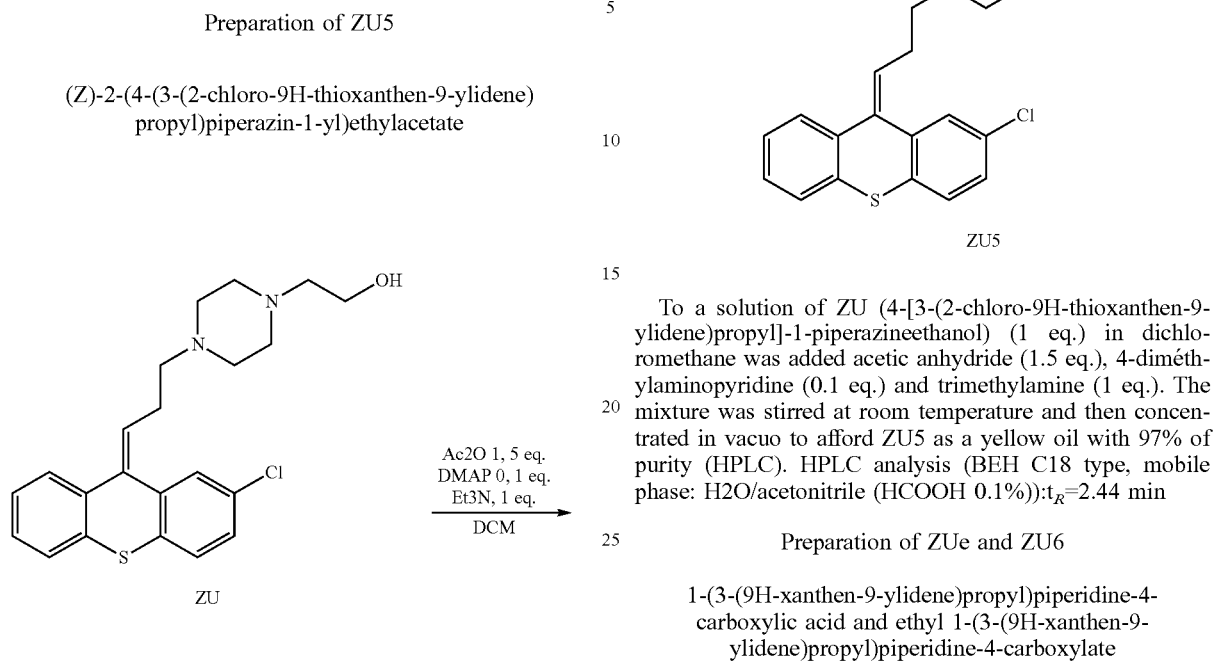

To a solution of ZU (4-[3-(2-chloro-9H-thioxanthen-9-ylidene)propyl]-1-piperazineethanol) (1 eq.) in dichloromethane was added acetic anhydride (1.5 eq.), 4-diméthylaminopyridine (0.1 eq.) and trimethylamine (1 eq.). The mixture was stirred at room temperature and then concentrated in vacuo to afford ZU5 as a yellow oil with 97% of purity (HPLC). HPLC analysis (BEH C18 type, mobile phase: H2O/acetonitrile (HCOOH 0.1%)):$t_R$=2.44 min Preparation of ZUe and ZU6

1-(3-(9H-xanthen-9-ylidene)propyl)piperidine-4-carboxylic acid and ethyl 1-(3-(9H-xanthen-9-ylidene)propyl)piperidine-4-carboxylate

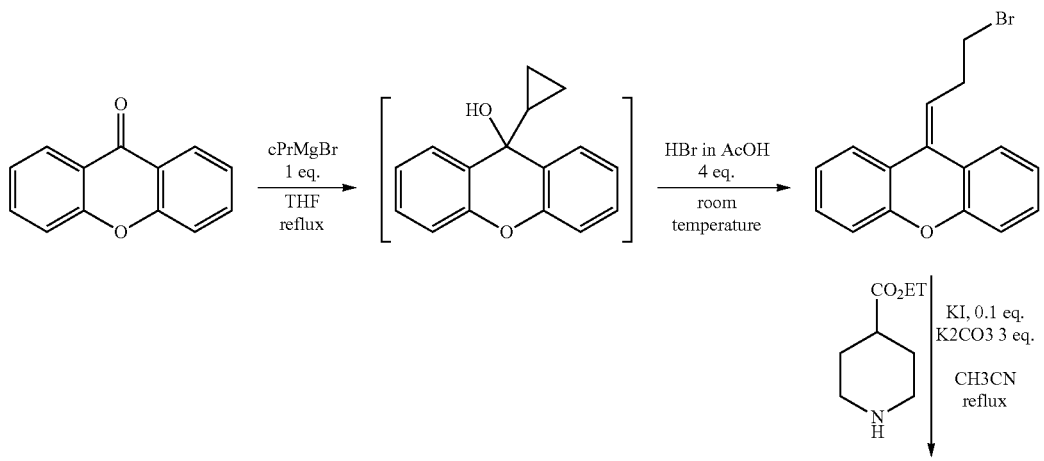

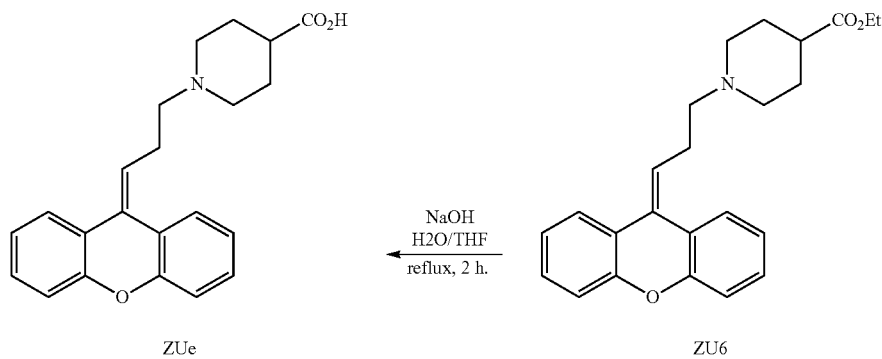

To a solution of 9-oxoxanthene (1.0 equiv.) in THF at reflux were added a solution of cyclopropylmagnesium bromide in THF (1.0 equiv.) and stirred during 2 hours. The mixture was cooled down at room temperature and a solution of hydrogen bromide in acetic acid (4 eq.) was added and stirred at room temperature. The reaction mixture was concentrated in vacuo and purified by silica gel column chromatography to obtain 9-(3bromopropylidene)-oxoxanthene.

Then, to a solution of 9-(3bromopropylidene)-oxoxanthene in acetonitrile at reflux was added Ethyl 4-piperidinecarboxylate (1.5 eq.), potassium iodide (0.1 eq.) and potassium carbonate (3 eq.). The mixture was stirred at reflux then concentrated in vacuo and purified by silica gel column chromatography to obtain ZU6 ZU6 is then dissolved in a mixture of THF and a solution of NaOH in water. After phase separation, the aqueous layer was extracted twice by diethyl ether. The global organic layer was, then, washed by a saturated solution of NaCl, dried over MgSO₄, filtered and concentrated in vacuo to afford ZUe as a white solid with a purity up to 97% in HPLC.

Preparation of ZUc (Z)-2-(4-(3-(2-(trifluoromethyl)-9H-thioxanthen-9-ylidene)propyl)piperazin-1-yl) Ethanamine

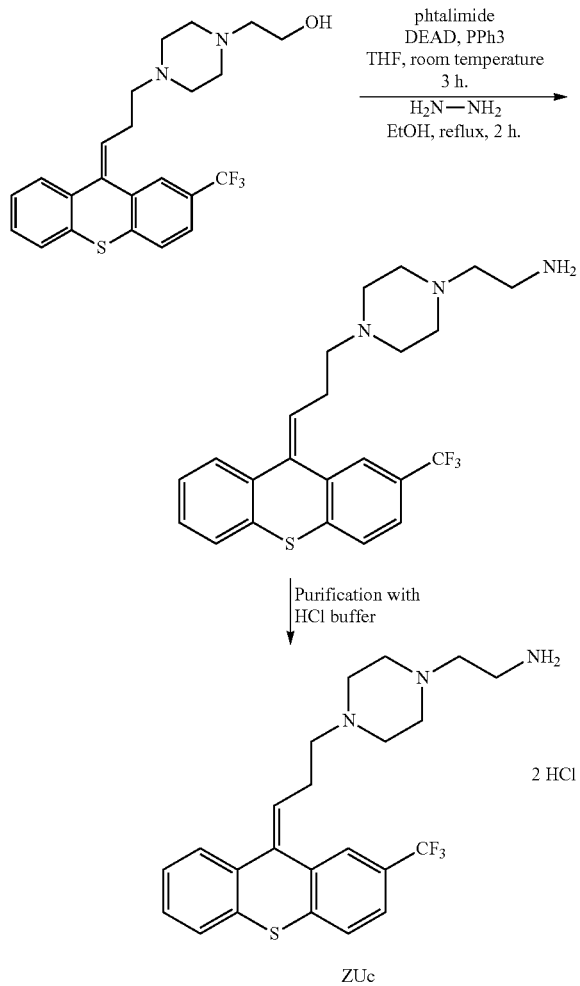

To a solution of ZU1 (2-[4-[3-[2-(trifluoromethyl)thioxanthen-9-ylidene]propyl]piperidin-1-yl]ethanol) (1 eq.) in THF was added diethylazodicarboxylate, phtalimide and triphenylphosphine. The solution was stirred at room temperature during 3 hours and then concentrated in vacuo. The crude oil was then dissolved in ethanol, hydrazine was added and the mixture was stirred at reflux during 2 hours. The crude product obtained after concentration was purified via a reversed phase chromatography using HCl as buffer to afford the compound ZUc as an hydrochloride salt (orange solid). [M+H]⁻ (ESI+): 434. HPLC analysis (BEH C18 type, mobile phase: H2O/acetonitrile (HCOOH 0.1%)): $t_R$=2.04 min Preparation of ZUd (Z)-1-(2-fluoroethyl)-4-(3-(2-(trifluoromethyl)-9H-thioxanthen-9-ylidene)propyl) Piperazine

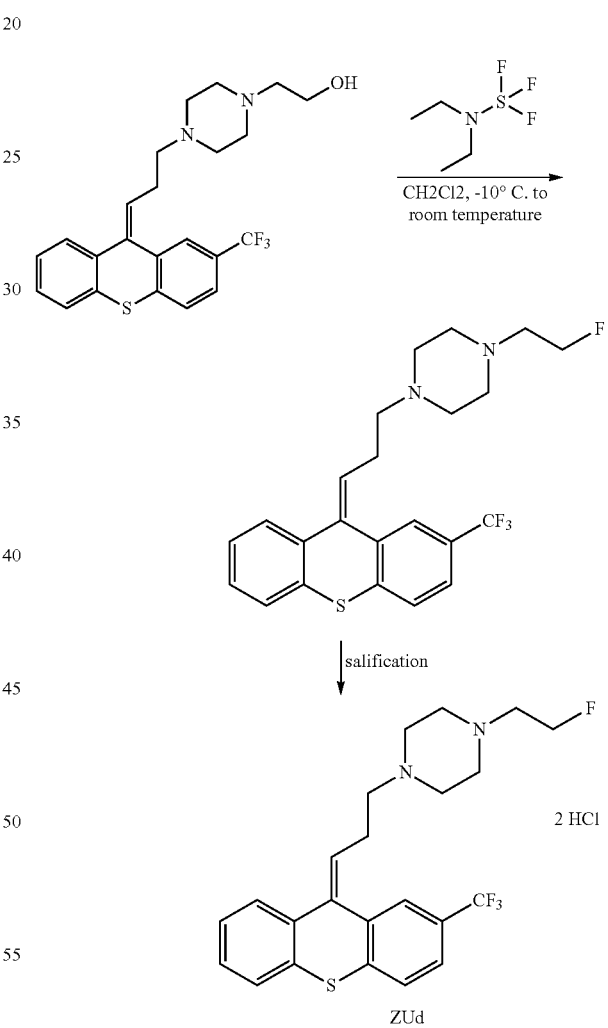

To a solution of flupenthixol in dichloromethane was added at −10° C. diethylaminosulfur trifluoride. The mixture was then stirred at room temperature. The crude product was purified via a reversed phase chromatography using HCl as buffer to afford the compound ZUd as a hydrochloride salt (orange solid) with 97% purity in HPLC. HPLC analysis (BEH C18 type, mobile phase: H2O/acetonitrile (HCOOH 0.1%)): $t_R$=3.59 min.

Compounds ZU, ZUa, ZUb, ZU1, ZU2

The Following Compounds can be easily Found in Commerce:

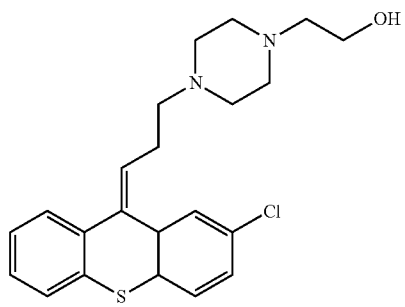
(ZU)

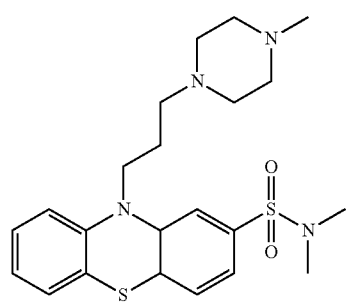
(ZUb)

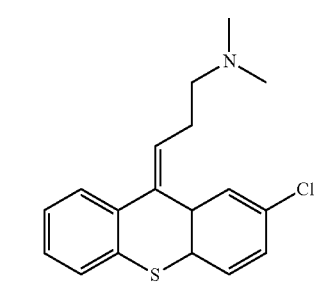
(ZUa)

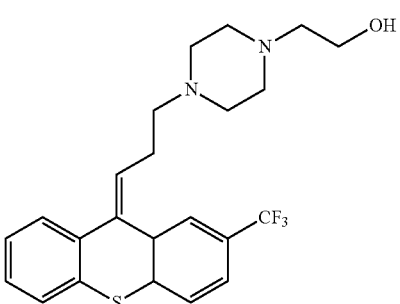
(ZU1)

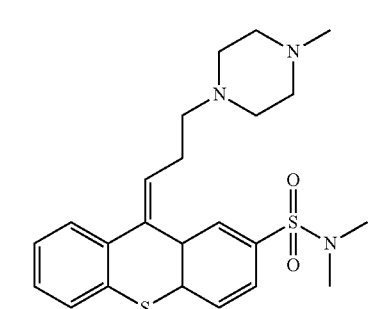
(ZU2)

Example 2: Ebselen Oxide Derivatives

The Following Compounds can be easily Found in Commerce:

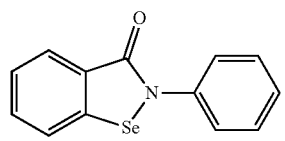
(EBa)

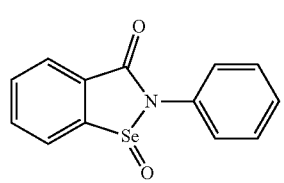
(EB1)

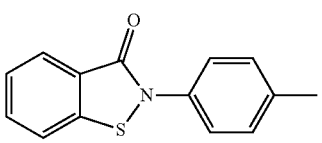
(EB2)

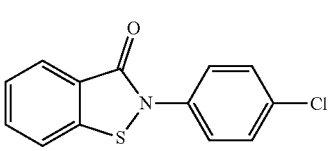
(EB3)

II. Biological Tests of the Compounds According to the Invention

Example 3: Inhibition of FERM/ErbB2 Interaction and Determination of $IC_{50}$ Values—in AlphaScreen® (Amplified Luminescent Proximity Homogenous Assay)

To validate that the Zuclopenthixol hydrochloride (ZU) and its derivatives interact with the juxtamembrane domain of ErbB2, we first analyzed in AlphaScreen® their efficiency to inhibit FERM/ErbB2 interaction in a dose-dependent manner and determined $IC_{50}$ value. Furthermore, to test the selectivity of those compounds, we tested their ability to disrupt the interaction between the FERM domain and the known ERM binding motif contained in the juxtamembrane region of CD44 as a control.

Method:
Reagents:
AlphaScreen® technology was used to assess the interaction between the Ezrin binding motif (EBM) contained in the juxtamembrane portions of ErbB2 or CD44 with the Ezrin FERM domain. For this purpose the Ezrin FERM domain in fusion with Glutathione-S-Transferase (GST) has been coupled to GSH-coated acceptor beads. Biotinylated ErbB2 peptide encoding the Ezrin binding motif (amino acid 674 to 689: biotin-ILIKRRQQKIRKYTMRRL, 26 aa) or the juxtamembrane region of CD44 (biotin-NSRRRCGQK-KKLVINSG), for the counter screen have been synthesized and coupled to streptavidin-covered donor beads. The AlphaScreen® reagents (Glutathione-coated Acceptor beads and streptavidin-coated Donor beads) were obtained from PerkinElmer.

Competition Assay:

The reaction was performed using white 384-well Optiplates (PerkinElmer, Whalham, Mass., USA) in 20 µl (total reaction volume) in a reaction buffer containing PBS, pH 7.4, 5 mM $MgCl_2$ and 0.02% CHAPS. 2.5 µL, of the compounds (0-50 µM) were transferred to the 384-well Optiplates containing 2.5 µl buffer and 5 µl of a mix solution containing 0.625 µM GST-FERM and 20 nM biotin-EBM or biotin-CD44 was added for 30 min at room temperature. 10 µl of a mix solution containing 20 µg/ml Glutathione-coated Acceptor beads and 20 µg/ml streptavidin-coated Donor beads was then added to the wells and incubation was further proceeded for 40 min or overnight in the dark and at room temperature. Light signal was detected with the EnVision® multilabel plate reader (PerkinElmer). All experiments involving AlphaScreen® beads were performed under subdued lighting.

Results:

The results of these tests obtained with the compounds of the invention are indicated in Table 1 below:

TABLE 1

| Compound | Competition assay FERM-ErbB2 interaction Max inhibition, % 20 h |
|---|---|
| ZU | 87.2 |
| ZU1 | 57 |
| ZU2 | 16 |
| ZU3 | 28 |
| ZU4 | 36 |
| ZU5 | 41 |
| ZUa | 3.9 |
| ZUb | 0 |
| ZUc | 45 |
| ZUd | 54 |
| ZUf | 11 |

ZU inhibited FERM/ErbB2 interaction in a dose-dependent manner by 72% at 1 h with an $IC_{50}$=50 µM, whereas it did not interfere with FERM/CD44 interaction (FIGS. 1A, 1B). This inhibitory effect was persistent at 24 h (>85% inhibition) with $IC_{50}$=9.8 µM. At 24 h, ZU also inhibited FERM/CD44 interaction, however to a lesser extent than FERM/ErbB2 interaction (53.32 vs. 87.2%).

ZU1, ZU2, ZU3, ZU4 and ZU5 also inhibited FERM/ErbB2 interaction in a specific and dose-dependent manner (Table 1). On the contrary, compounds ZUb, lacking a double bond between the heterocyclic groups and ZUa lacking a heterocyclic group, do not significantly inhibited FERM/ErbB2 interaction.

Figure 1C:
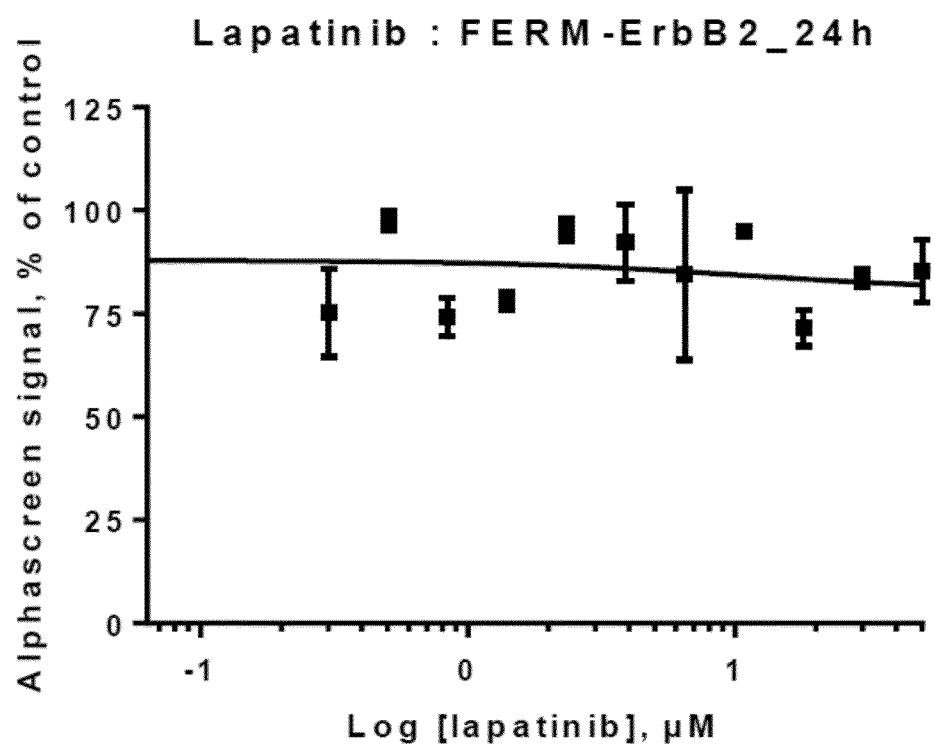
FIG. 1. represents the inhibition of (A) FERM/ErbB2 or (B) FERM/CD44 interaction by compound ZU; (C) the inhibition of FERM/ErbB2 by comparative compound lapatinib measured by Alphascreen experiments after 24 h.

EB1 efficiently inhibited FERM/ErbB2 interaction in a dose-dependent manner by 43% at 1 h, without significantly altering FERM/CD44 interaction at low doses (FIGS. 1C, 1D).

Hence, these compounds selectively disrupted the FERM/ErbB2 interaction and therefore represent very attractive compounds.

Moreover, as a comparative compound, lapatinib did not inhibit FERM/ErbB2 interaction.

Example 4: Inhibition of ErbB2 Activation and Determination of $IC_{50}$ Values—In Cellulo The ability of ZU and EB1 and their derivatives to inhibit ErbB2 activity in cellulo on a commonly used ErbB2-overexpressing breast cancer cell line SKBR3 was analyzed. SKBR3 were treated 24 h with increasing concentrations of the compounds (0.625-80 µM) and ErbB2 phosphorylation was addressed by dot blot analysis using an anti-phosphotyrosine antibody (clone 4G10). Quantifications show the result of two independent experiments.

Results:

The results of these tests obtained are indicated in Table 2 below:

TABLE 2

| | ErbB2 activation 24 h | |
|---|---|---|
| Compound | Max inhibition, % | $EC_{50}$, µM |
| ZU | 93.22 | 22.39 |
| ZU1 | 88.58 | 19.05 |
| ZU2 | 74.17 | 31.62 |
| ZU3 | 75.12 | 32.36 |
| ZU4 | 27.48 | 47.86 |
| ZU5 | 97.49 | 43.65 |
| ZU6 | 36.23 | 35.48 |
| ZUc | 90.80 | 5.13 |
| ZUd | 51.35 | 20.42 |
| ZUe | 0 | / |
| ZUf | 0 | / |
| EBa | 15.55 | 40.74 |
| EB1 | 66.86 | 23.44 |
| EB2 | 43.81 | 18.20 |
| EB3 | 66.41 | 19.50 |

Figure 2A:
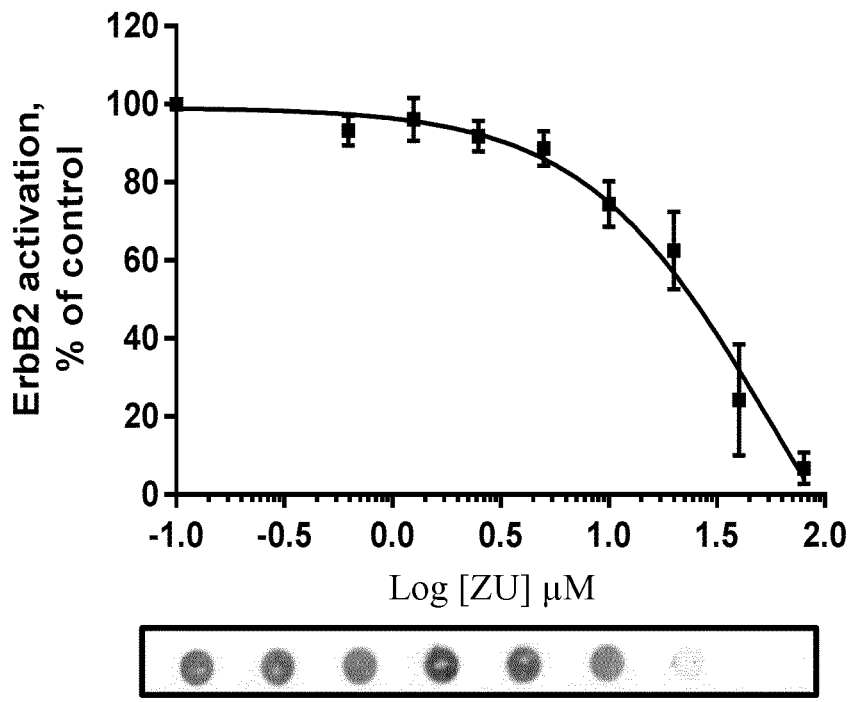
FIG. 2. represents the effect of (A) compound ZU and (B) compound EB1 on ErbB2 activation measured by dot blot analysis of ErbB2 phosphorylation in SKBR3 cells.

ZU strongly decreased ErbB2 phosphorylation in a dose-dependent manner, reaching a maximum inhibition of 90% with an $IC_{50}$=20 µM (FIG. 2A).

ZU derivatives such as ZU1, ZU2, ZU3, ZU5, ZUc and ZUd potently decreased ErbB2 phosphorylation in a dose-dependent manner (reaching a maximum of 75 to 95% inhibition with $IC_{50}$ varying from 5 to 35 µM) (Table 2). On the contrary, ZU4 and ZU6 exhibit a lower decrease of the ErbB2 phosphorylation. ZUf and ZUe had no effect on ErbB2 activation.

Figure 2B:
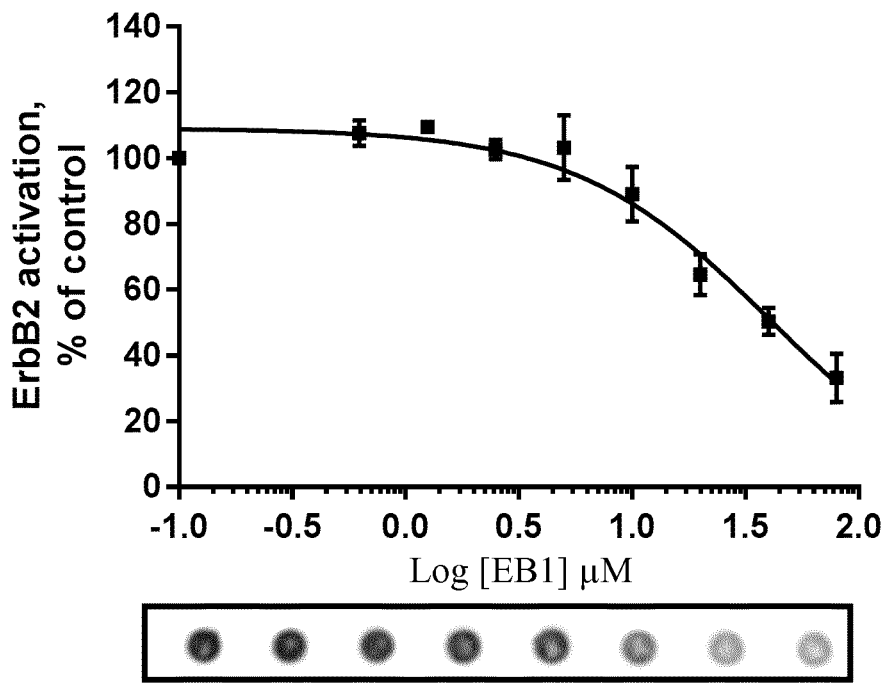
Figure 3A:
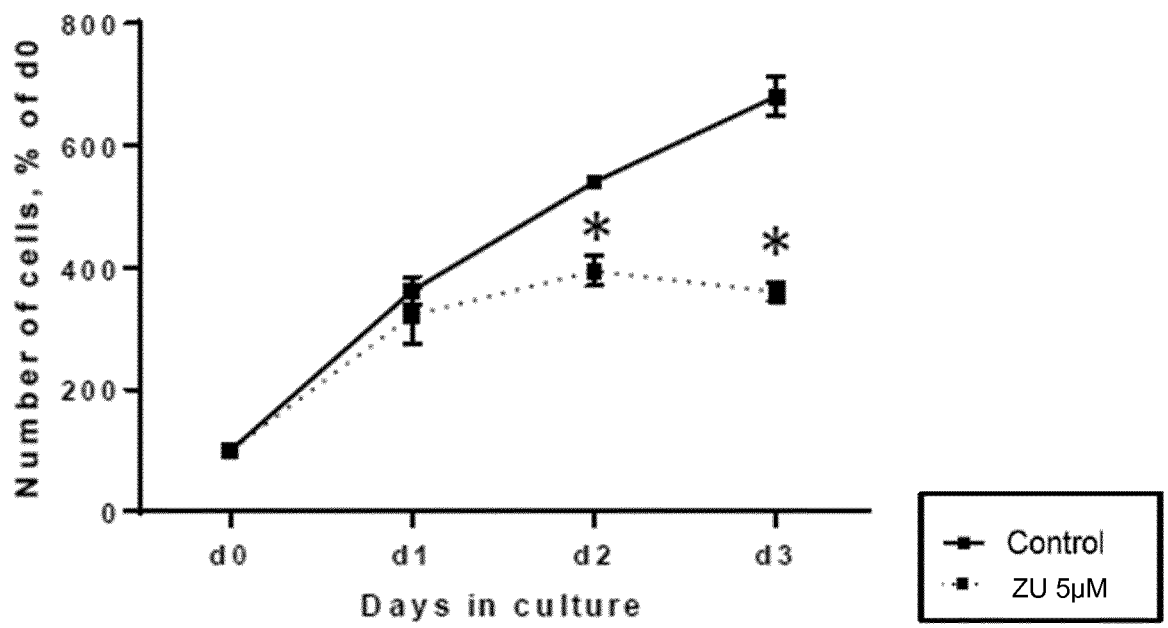
FIG. 3. represents the specific inhibition of the ErbB2-dependent cell proliferation of (A) SKBR3 and (B) BT474 by ZU measured by MTT assays as compared to an absence of inhibition of the proliferation of the ErbB2-independent (C) MCF7 cell line (D) MDA-MB-231 cell line-and the normal endothelial cell line (E) HBMEC (unpaired T-test, *$p<0.05$, significantly different from control).
Figure 3B:
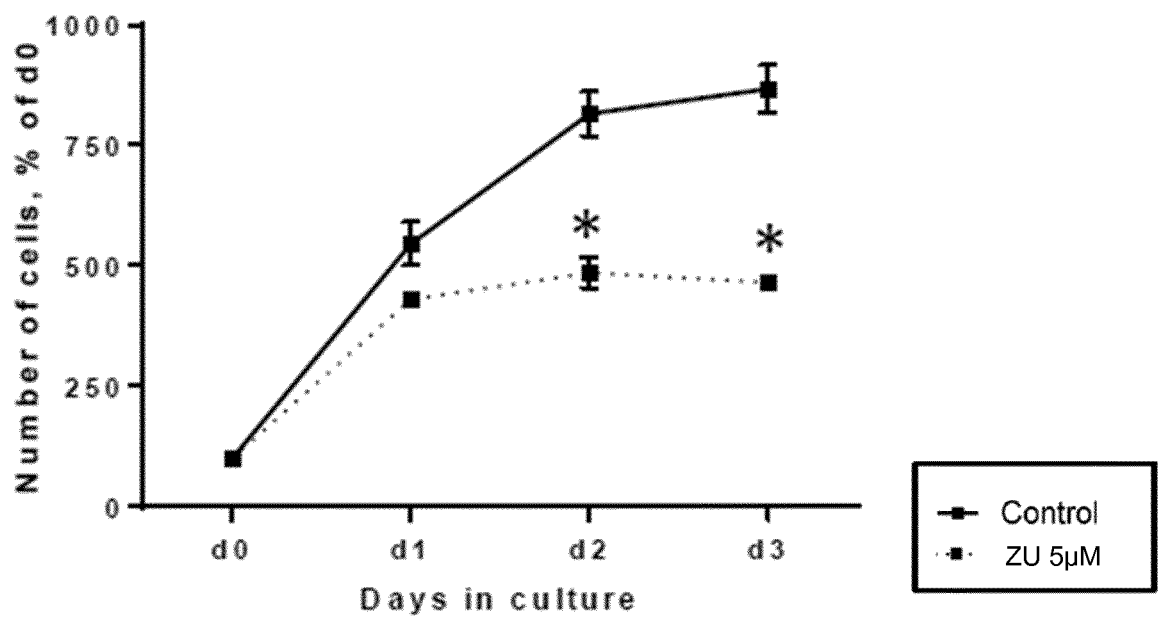
Figure 3C:
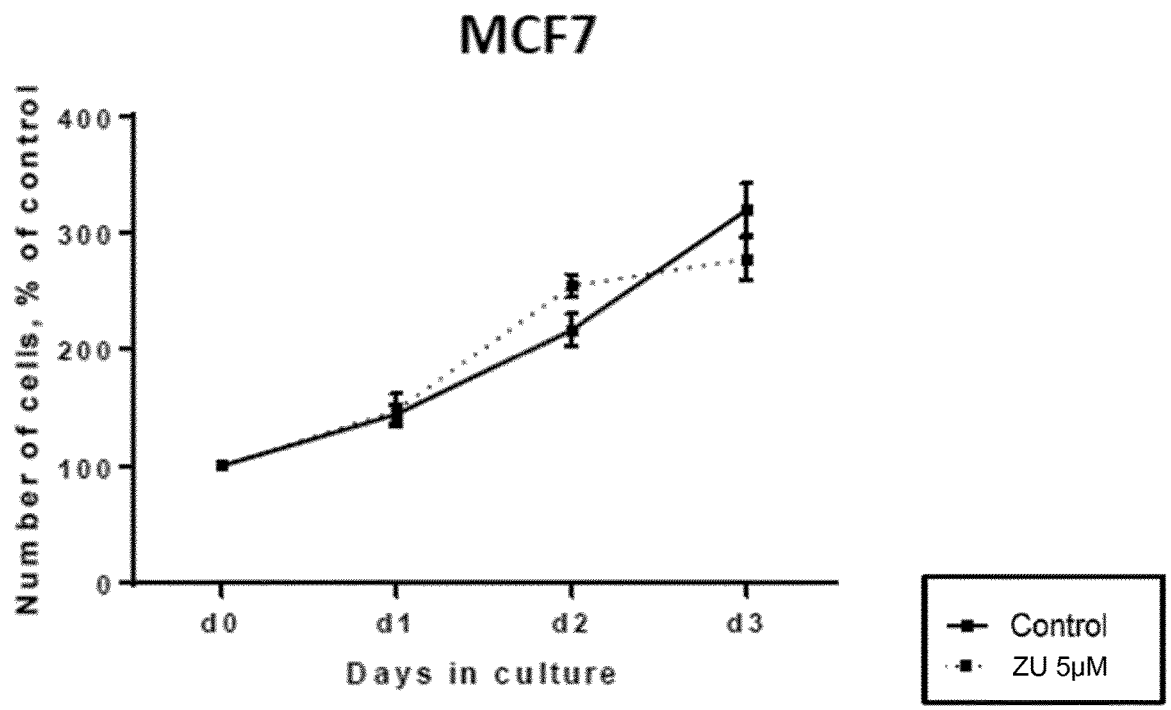
Figure 3D:
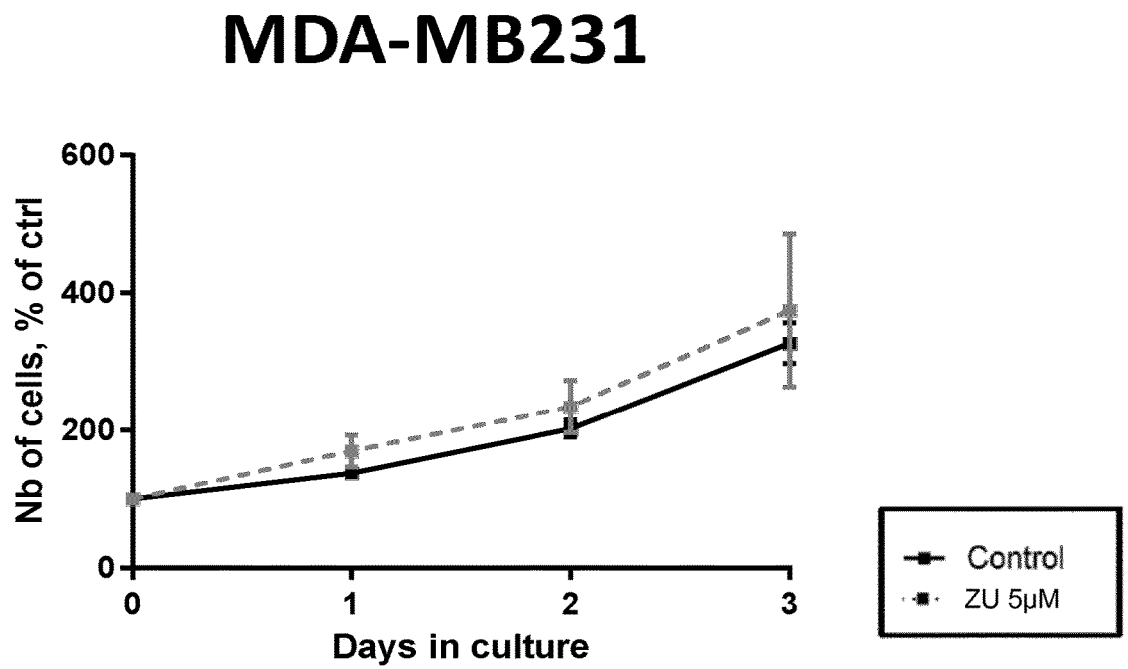
Figure 3E:
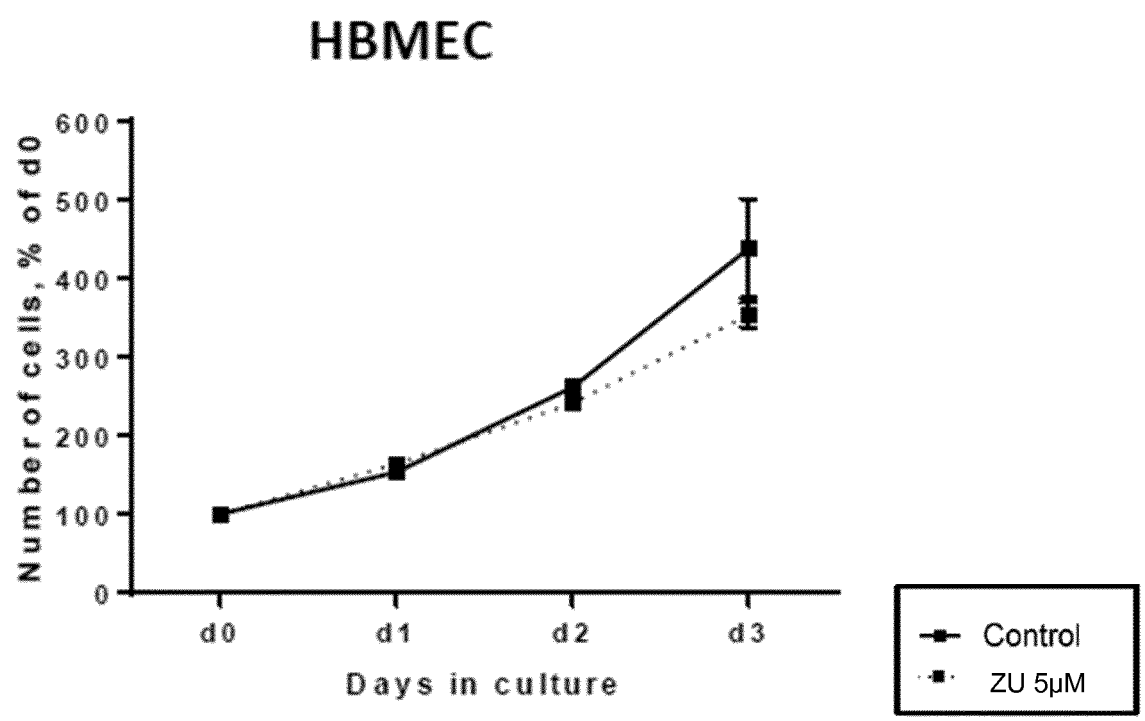
Figure 4A:
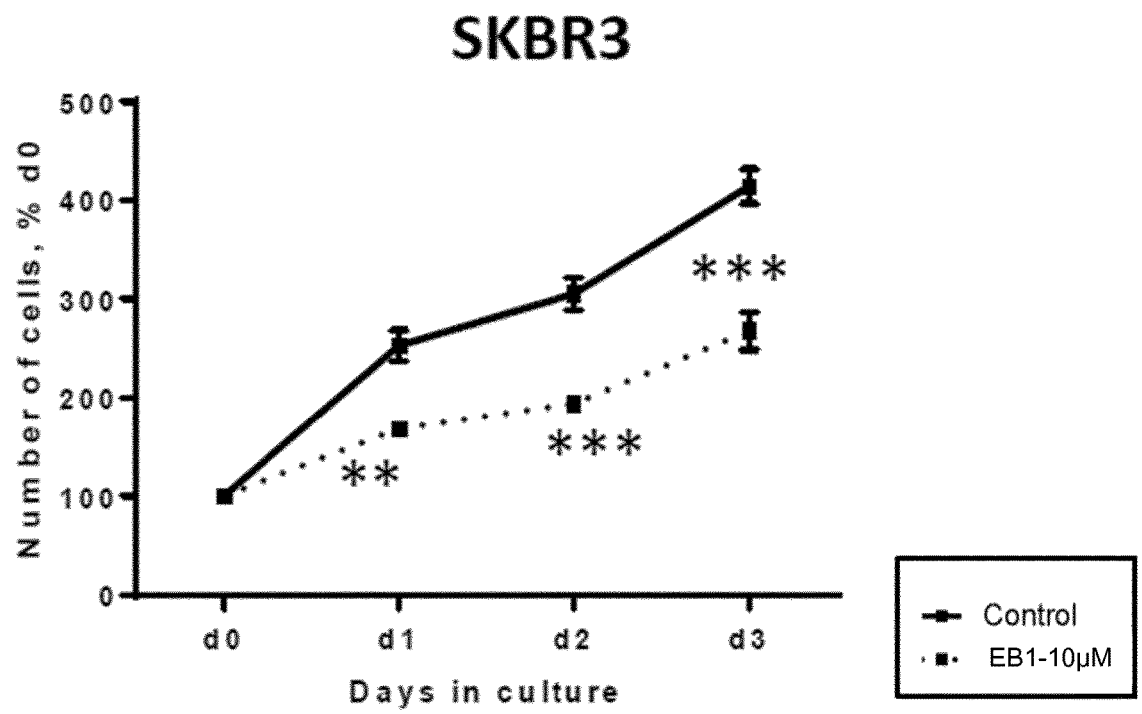
FIG. 4. represents the specific inhibition of the ErbB2-dependent cell proliferation of (A) SKBR3 and (B) BT474 by EB1 measured by MTT assays as compared to an absence of inhibition of the proliferation of the ErbB2-independent (C) MCF7 cell line (D) MDA-MB-231 cell line-and the normal endothelial cell line (E) HBMEC (unpaired T-test, $p<0.01$, *$p<0.001$, significantly different from control).
Figure 4B:
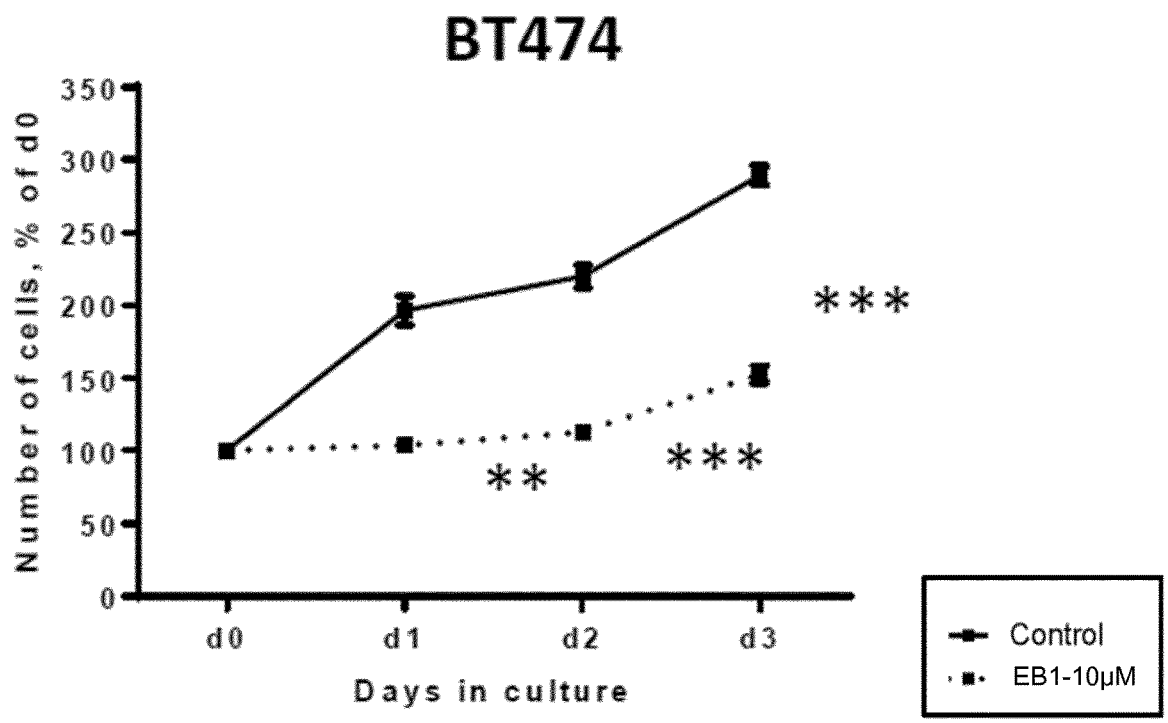
Figure 4C:
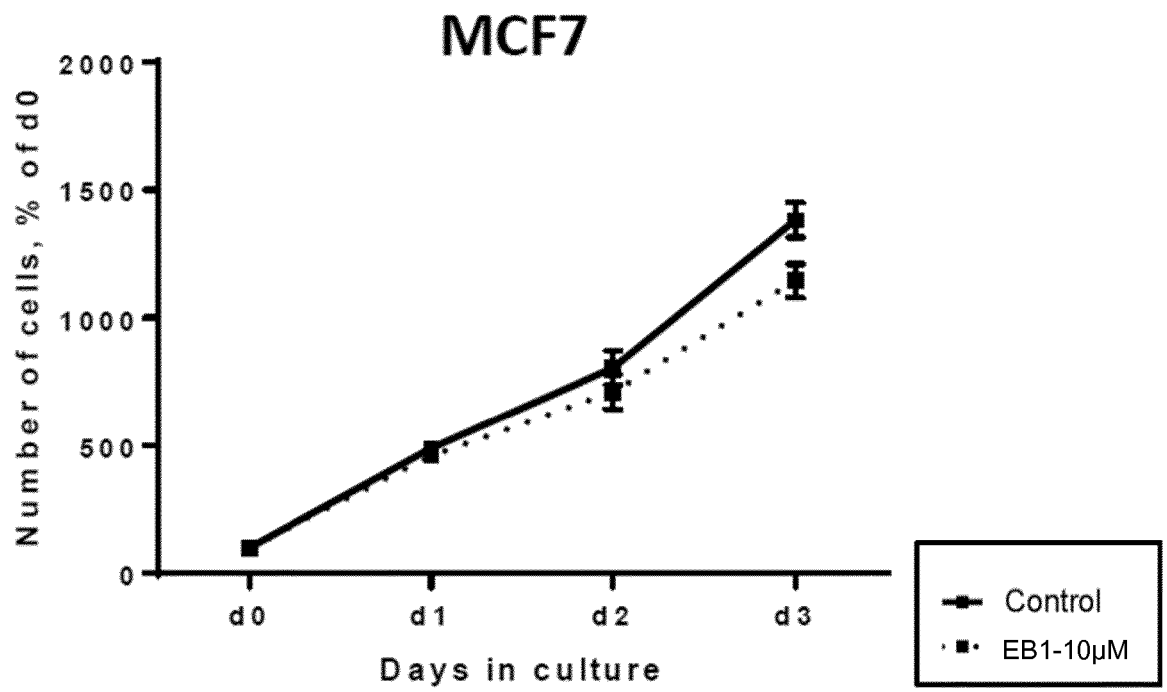
Figure 4D:
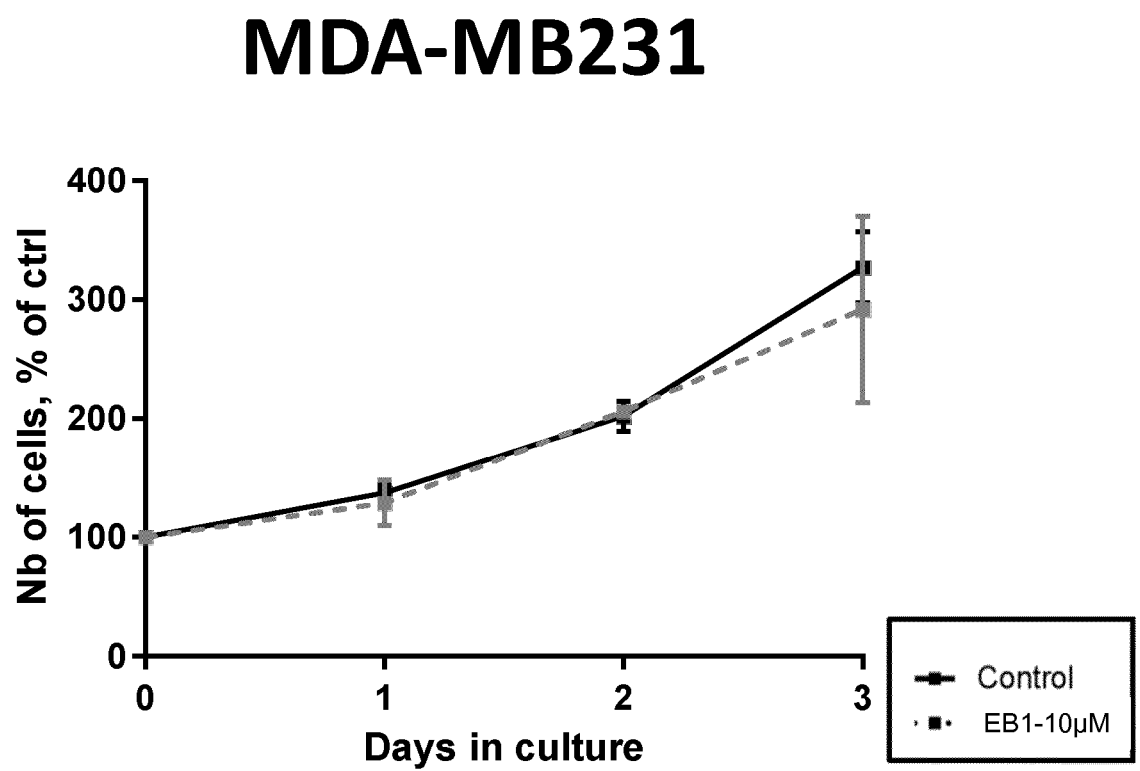
Figure 4E:
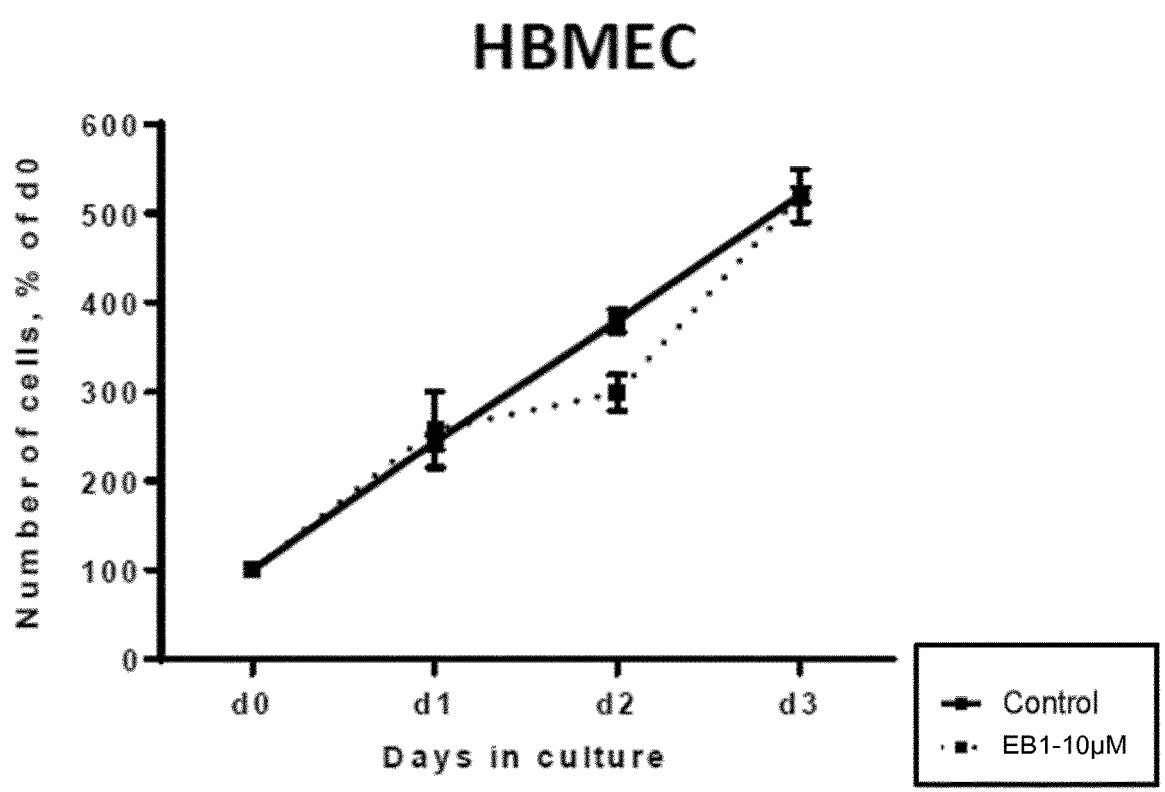

EBa only slightly reduced ErbB2 phosphorylation by 15% with concentration of 10 µM. EB1 was more efficient in preventing ErbB2 activation than EBa, as it reduced ErbB2 phosphorylation in a dose-dependent manner, reaching a maximum inhibition of 70% with an $IC_{50}$=20 µM (FIG. 2B).

EB2 and EB3 decreased ErbB2 phosphorylation in a dose-dependent manner reaching a maximum of 43 to 66% inhibition with $IC_{50}$ varying from 18 to 20 µM.

Example 5: Inhibition of ErbB2-Dependent Cell Proliferation

We then analyzed the ability of ZU and EB1 and their derivatives to decrease the ErbB2-dependent cell proliferation. We used the ErbB2-overexpressing human breast cancer cell lines SKBR3 and BT474, as well as two non ErbB2-dependent breast cancer cell lines MCF7 and MDA-MB-231 and normal human endothelial cells (HBMEC) as a control, to discard compounds presenting non-specific toxic effects.

Method:

SKBR3, BT474, MCF-7, MDA-MB-231 and HBMEC cells were treated with the compounds as indicated, and cell proliferation was determined each day during 3 days using an MTT assay. Non treated cells were included as a negative control.

Results:

The results of these tests obtained are indicated in Table 3 below:

TABLE 3

| | Cell proliferation at d 3 | | | | | |
|---|---|---|---|---|---|---|
| | SKBR3 | | BT474 | | HBMEC | |
| | Max inhibition, % | $EC_{50}$, µM | Max inhibition, % | $EC_{50}$, µM | Max inhibition, % | $EC_{50}$, µM |
| ZU | 46.2 | 14.1 | 31.5 | 6.8 | 4.7 | ND |
| ZU1 | 51.12 | 5.13 | 79.67 | 3.1 | 4.7 | ND |
| ZU3 | 32.6 | 15.5 | 31.5 | 4.2 | 0 | ND |
| ZU5 | 28.2 | 3.5 | 30.8 | 17.8 | 24.5 | 21.9 |
| ZUc | 78.9 | 0.34 | 94.9 | 0.23 | 68.8 | 0.14 |
| ZUd | 86.4 | 6.7 | 86 | 16.5 | 90 | 16.3 |
| EB1 | 96.7 | 7.4 | 100 | 5.5 | 94.4 | 99.15 |
| EB2 | 34.1 | 9.3 | 20 | 11.7 | 29.5 | 11.5 |
| EB3 | 63.5 | 8.9 | 82.7 | 6.9 | 75.1 | 2770 |

Treatment with 5 µM ZU reduced by 50% SKBR3 and BT474 proliferation at day 2 and 3, with an $IC_{50}$ of 14 µM and 7 µM respectively, without any effect on HBMEC or on MCF7 or MDA-MB-231 proliferation (FIG. 3, unpaired T-test, *p<0.05, significantly different from control).

Treatment with 5 µM ZU1 reduced SKBR3 and BT474 proliferation at day 2 and 3 by 30 to 50%, without any effect on HBMEC proliferation. This inhibition could be further enhanced to 80 to 95% when treating cells with 10 µM ZU1.

Treatment with 20 µM ZU3 decreased SKBR3 and BT474 proliferation by 30% without any effect on HBMEC cell proliferation.

Treatment with 1 and 5 µM ZU5 reduced SKBR3 and BT474 proliferation by 60% and 33% respectively, at day 3, without any effect on HBMEC proliferation.

Treatment with 0.5, 1 and 2 µM ZUc reduced SKBR3 and BT474 proliferation from 50% to 95%, at day 3, but also inhibited HBMEC proliferation from 60% to 85% at day 3.

Treatment with 20 µM ZUd reduced SKBR3 and BT474 proliferation by 86%, at day 3, but also inhibited HBMEC proliferation by 90% at day 3.

Furthermore, treatment with 10 µM EB1 potently inhibited the proliferation of both SKBR3 and BT474 at day 2 and 3, reaching a 95 to 100% inhibition at a $IC_{50}$ of 7.5 and 5.5 µM respectively, without any effect on HBMEC or on MCF7 or MDA-MB-231 proliferation (FIG. 4, unpaired T-test, p<0.01, *p<0.001, significantly different from control).

Treatment with 5 µM EB2 did not significantly decreased SKBR3 proliferation but reduced BT474 proliferation at day 2 and 3 by 30 to 35%, without any effect on HBMEC cell proliferation.

Treatment with 7 µM EB3 did not significantly decreased SKBR3 proliferation but significantly reduced BT474 proliferation by 30% at day 2, without any effect on HBMEC cell proliferation.

These results indicated that both ZU and EB1 and their derivatives ZU1, ZU2, ZU3, ZU5, EB2 and EB3 have a potent and selective inhibitory effect on human breast cancer cells overexpressing ErbB2. On the contrary, ZUc and ZUd exhibit non-specific toxic effects, since they also inhibit the proliferation of control cells.

Example 6: Inhibition of the Colony Formation of SKBR3 and of BT474 in a Soft Agar Assay To confirm the potent effect of ZU and EB1, we analyzed their efficiency to inhibit the colony formation of SKBR3 or BT474 cells in a soft agar assay.

Method:

A bottom layer of 0.8% agarose in DMEM supplemented with 20% SVF and penicillin/streptomycin was added to 24 well plates before seeding $25.10^3$ SKBR3 or BT474 cells/well in a 0.6% agarose top layer. Cells were left untreated or treated with 5 or 10 µM ZU or EB1 or 5 µM AG1478 (a non-specific ErbB2 kinase inhibitor) as a positive control. Treatments were renewed 3 times a week. After 6 weeks, the number of colonies and their size were quantified using image J software. The colony formation is illustrated for each condition. Data are presented as mean±SEM.

Results

The results of these tests are shown in FIGS. 5A to 5D.

Figure 5A:
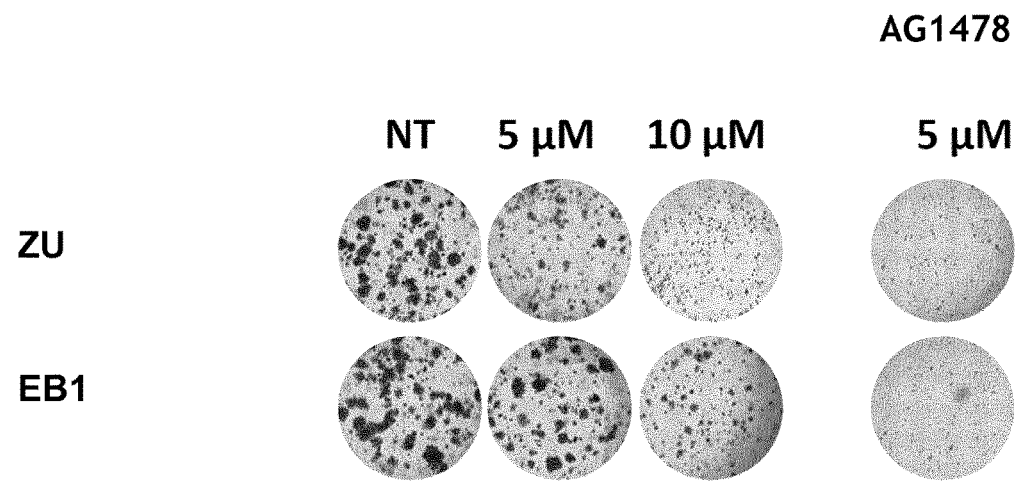
FIG. 5. represents the inhibition of the anchorage-independent growth of SKBR3 (A-B) or BT474 (C-D) cells by compound ZU and compound EB1 measured in soft agar assays. AG1478, a tyrosine kinase inhibitor of the EGFR family members was used as a control. (A) and (C) display representative photographs of the colonies; (B) and (D) show the colony mean area measured for each treatment condition (5B: One way ANOVA F(3,6)=227.5; Dunnett's Post Hoc Test, *$p<0.001$, **$p<0.0001$; 5D, One way ANOVA F(1,10)=14.03; Dunnett's Post Hoc Test *$p<0.01$).
Figure 5B:
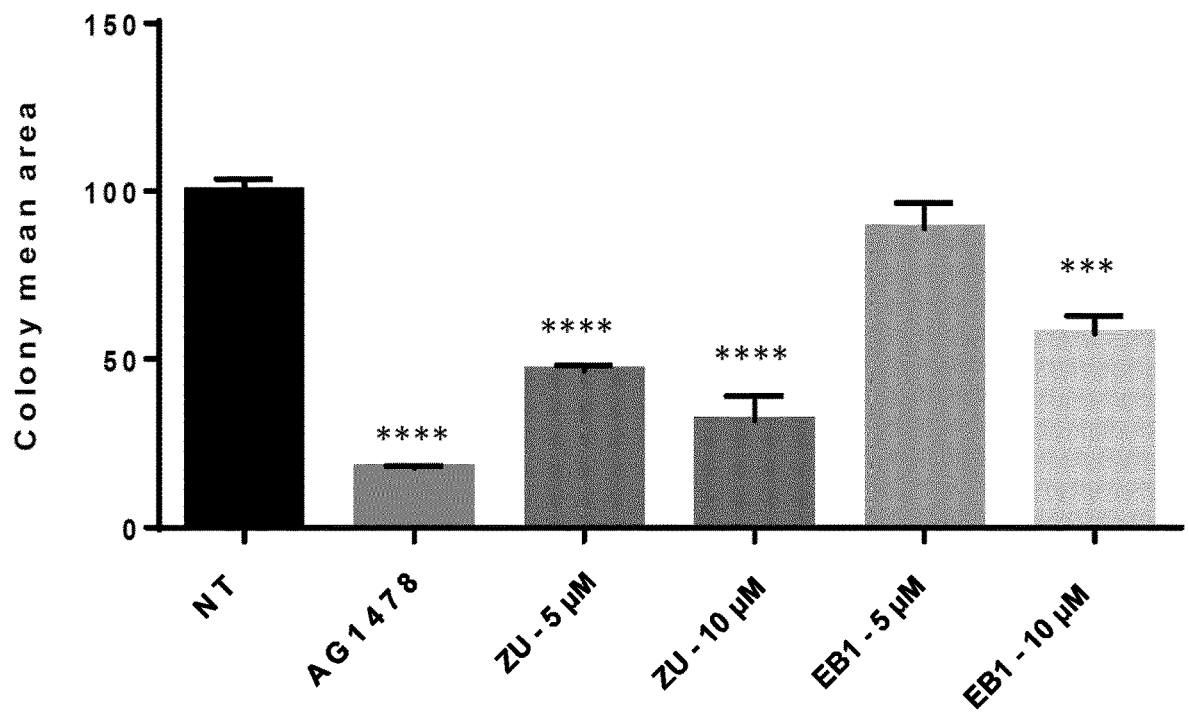
Figure 5C:
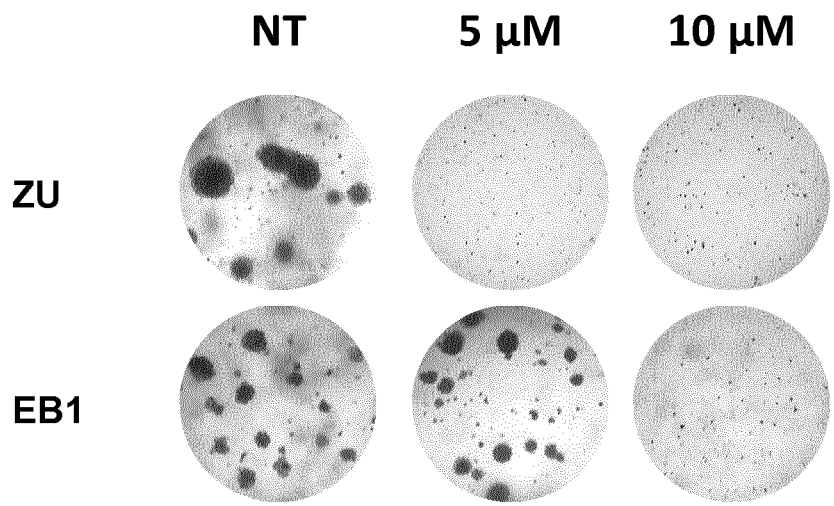
Figure 5D:
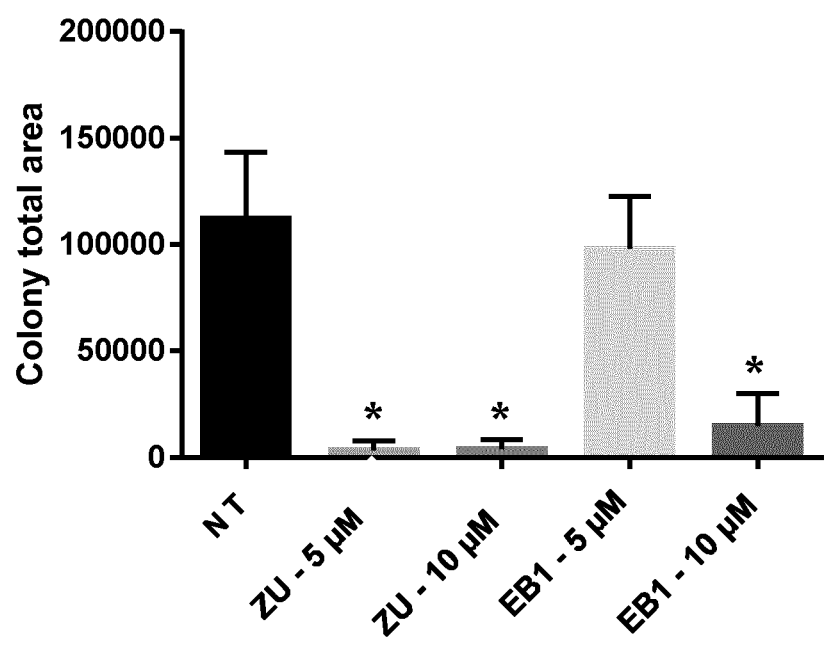

We observed that treatment with both ZU (FIGS. 5A and 5B: One way ANOVA F(3,6)=227.5; Dunnett's Post Hoc Test, *p<0.001, **p<0.0001) and EB1 (FIGS. 5C and 5D: One way ANOVA F(1,10)=14.03; Dunnett's Post Hoc Test *p<0.01) compounds inhibited the anchorage-independent growth of SKBR3 and BT474, with a potent action on the size of the colony formed.

Example 7: Inhibition of the Development In Vivo of Human Breast Cancer BT474 Cells We addressed the ability of ZU to inhibit the development in vivo of human breast cancer BT474 cells orthotopically implanted in the mammary fat pad of immunodeficient NOG mice, in the presence of estradiol supplement, as this constitutes the more relevant system comparable to the human situation to address the access of these molecules to tumors cells inside their organ of origin and their potential effect on tumoral dissemination.

Method, First Set of Experiments:

$5.10^6$ BT474 cells were implanted orthotopically in the mammary fat pad of NOD.Cg-Prkdc scid/J mice, in the presence of estradiol supplement. After 4 weeks, mice were injected with ZU (N=10, 5 mg/kg per day for 5 days a week, followed by 3 mg/kg for 5 days a week during three weeks for N=6) or vehicle (N=10, 10% DMSO in PBS). Mice weight and tumor volume were measured 3 and 2 times a week respectively.

Figure 6:
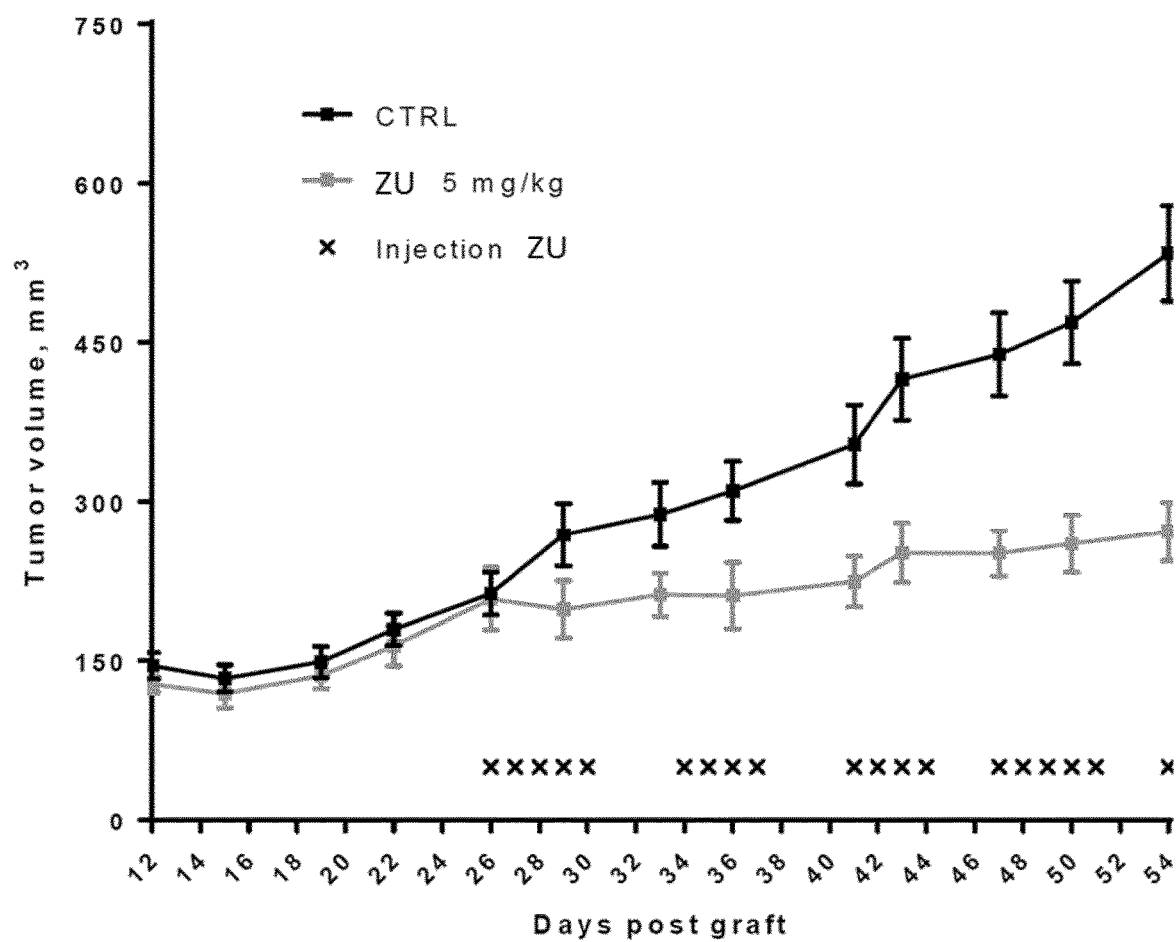
FIG. 6. represents the inhibition by compound ZU of the rate of BT474 tumor proliferation in vivo in orthotopic xenografts.
Figure 7A:
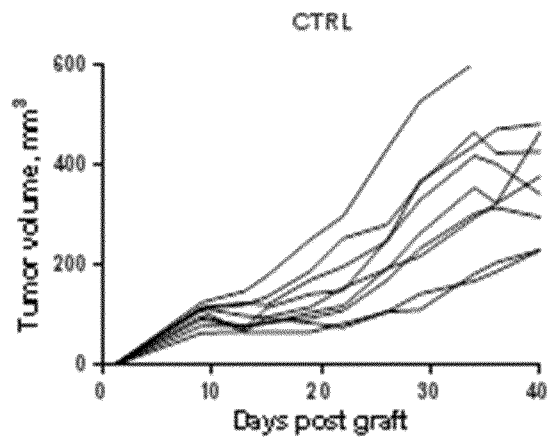
FIG. 7. represents the inhibition by compound ZU of the rate of BT474 tumor proliferation in vivo in orthotopic xenografts. (A), (B) and (C) show the quantification of the tumor volume (mm$^3$) of each mouse injected with saline, 4 mg/kg and 5 mg/kg of ZU respectively; while (D) and (E) show the normalized tumor volume (expressed as a % of tumor volume measured at day 19 (d19) post graft) of mice injected with saline and 4 mg/kg of ZU and saline and 5 mg/kg of ZU respectively. (G) displays pictures of tumors from each group. (F) and (H) display quantification of the tumor weight and body weight respectively.
Figure 7B:
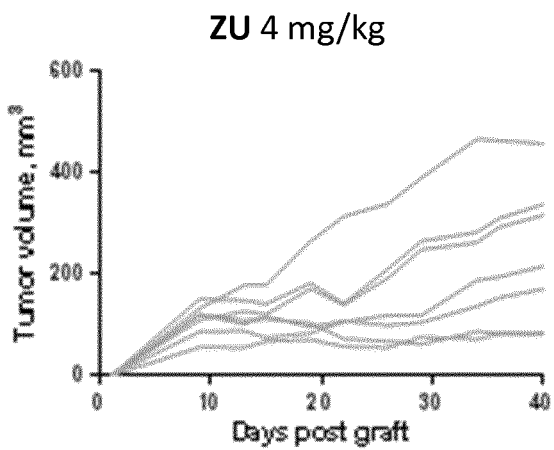
Figure 7C:
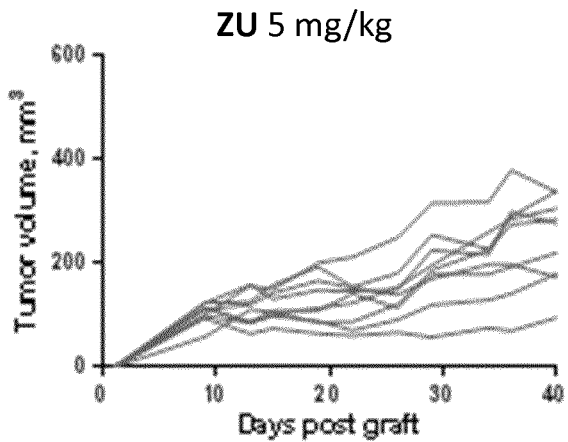
Figure 7D:
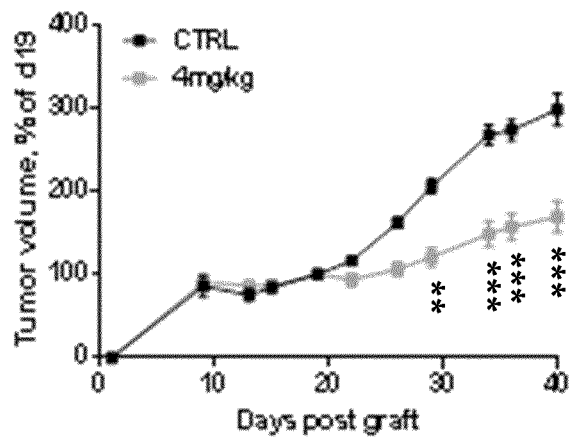
Figure 7E:
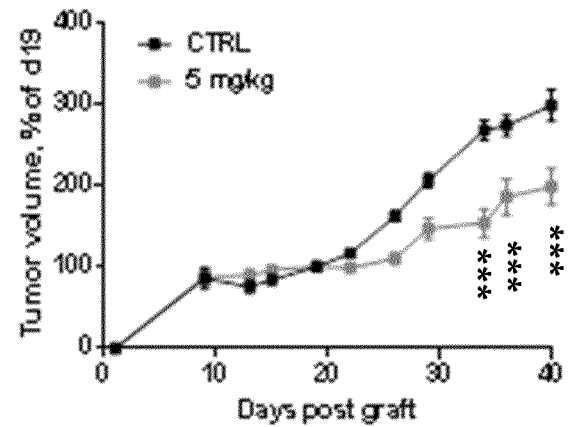
Figure 7F:
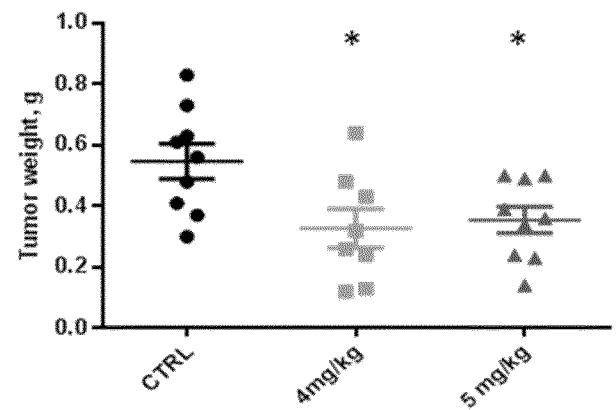
Figure 7G:
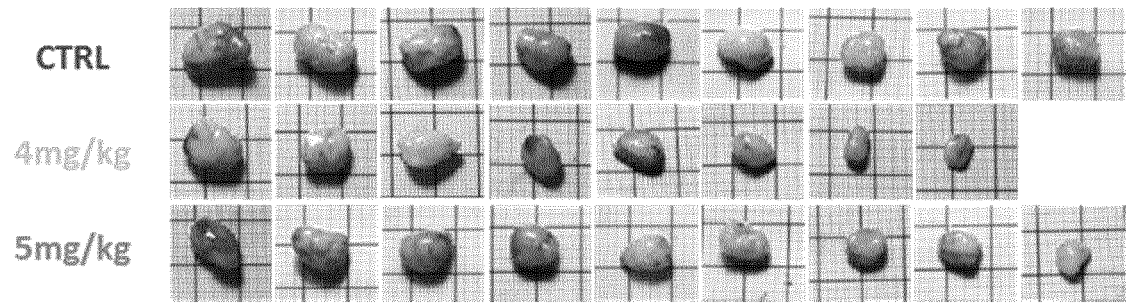
Figure 7H:
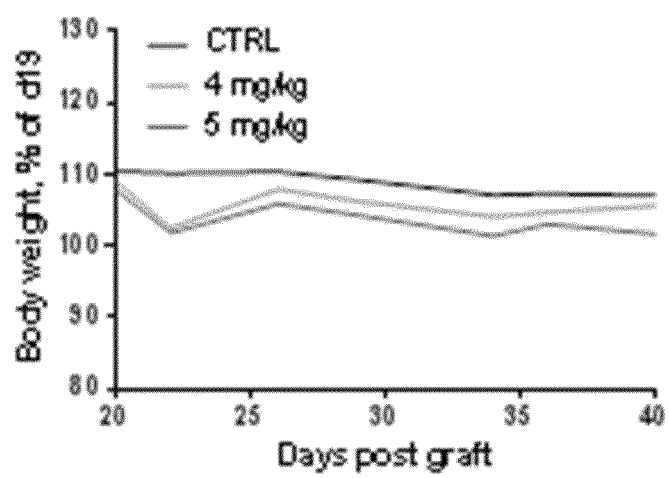

Results, First Set of Experiments:

Injection of ZU (5 mg/kg per day for 5 days a week, 10 mice per group, followed by 3 mg/kg for 5 days a week during three weeks for 6 mice) completely blocked tumor progression in vivo, in comparison to the tumor progression in mice treated with the vehicle (10 mice per group, 10% DMSO in PBS) as a control (FIG. 6).

This experiment confirmed the potent inhibitory effect of ZU on human breast cancer cells overexpressing ErbB2. Furthermore, as BT474 cells have a known Trastuzumab-resistance status, this experiment shows the efficacy of ZU to overcome Trastuzumab-resistance.

Nonetheless, at 5 mg/kg, 3 mice out of 10 were dizzy or sleepy for long, lost weight and finally died after several injections. When switched at 3 mg/kg, the treatment was well supported by the mice.

Method, Second Set of Experiments:

Drug Administration Schedules were Slightly Changed to Overcome the Potential Side Effects Detected with the 5 mg/kg Dose.

$5.10^6$ BT474 cells were implanted orthotopically in the mammary fat pad of NOD.Cg-Prkdc scid/J mice, in the presence of estradiol supplement. Nineteen days after implantation, treatment began and mice were injected i.p. with 5 m/kg ZU (5 mg/kg per day for 3 days a week, during three weeks for N=9), 4 mg/kg ZU (5 days a week during three weeks, N=8) or vehicle (N=9, 10% DMSO in PBS). Mice weight and tumor volume were measured 3 and 2 times a week respectively.

Results, Second Set of Experiment:

Injection of ZU (5 mg/kg per day, 3 days a week, or 4 mg/kg, 5 days a week) dramatically reduced tumor progression in vivo, in comparison to the tumor progression in mice treated with the vehicle as a control (FIG. 7). Of, note using this administration scheme, treatment is well tolerated.

Two-way ANOVA: interaction between time and ZU treatment $F(16,207)=8.309$, $P<0.0001$, ZU treatment effect $F(2,207)=15.97$, $P<0.0001$, time effect $F(8,207)=115.9$, $P<0.0001$. Point by point comparison with controls using the Bonferroni posttest: $P<0.01$, *$P<0.001$. Quantification of the tumor weight (F). Student T test *$P<0.05$. Pictures of tumors from each group (G) and body weight (H).

This experiment confirmed the potent inhibitory effect of ZU on human breast cancer cells overexpressing ErbB2. Furthermore, as BT474 cells have a known trastuzumab-resistance status, this experiment shows the efficacy of ZU to overcome trastuzumab-resistance.

Example 8: Surface Plasmon Resonance Assays

We analyzed the ability of ZU to directly bind to the juxtamembrane domain of ErbB2 using Surface Plasmon Resonance assays on a Biacore T200. For that, we compared the affinity of the compounds for a peptide containing the Ezrin binding motif ILIKRRQQKIRKYTMRRL of ErbB2 immobilized on sensorchips, which was reflected by the amplitude of the SPR response.

Method:

Compound ZU and EB1 were validated for their interaction with peptide encoding the juxtamembrane region of ERBB2 using a Biacore T200 (IECB, Bordeaux). Biotinylated peptide encoding the juxtamembrane region of ERBB2 (biotin-ILIKRRQQKIRKYTMRRL) has been immobilized on Streptavidin-coated sensor chips (Series S sensor chip SA, GE Healthcare). Compound ZU in PBS, 0.02% tween20 buffer was used as analyte, and the Ezrin FERM domain has been used as a positive control.

Figure 8:
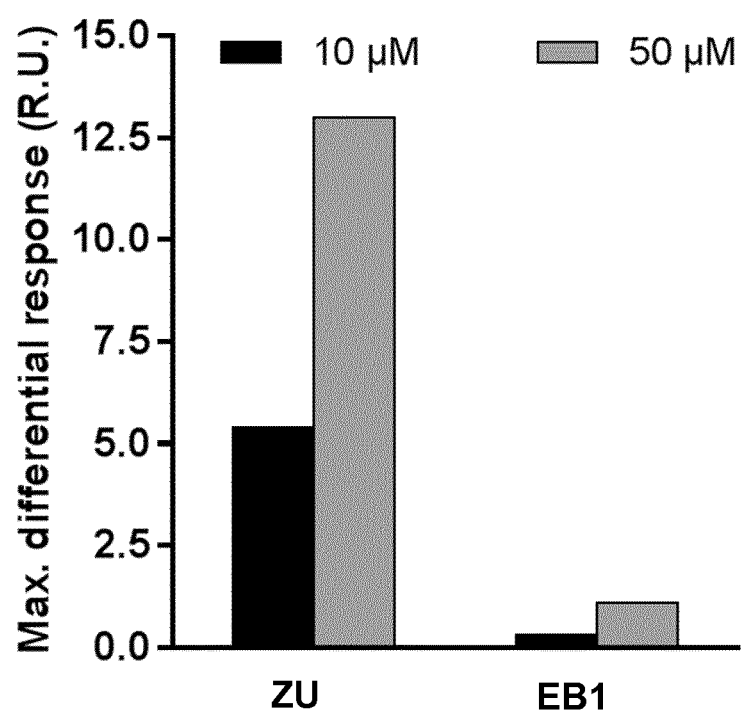
FIG. 8. represents the interaction of compound ZU with ErbB2 juxtamembrane peptide as measured by SPR experiments at 50 and 10 μM.

Results:

Both Zuclopenthixol (ZU) and Ebselen oxide (EB1) bound to the immobilized peptide, therefore confirming the molecular interaction between these compounds and ErbB2 (FIG. 8).

Example 9: ZU Conformation Tests

Zuclopenthixol is in a cis conformation. To evaluate the importance of this conformation for the biological effect of this molecule on ErbB2, we tested the effects of a mix of cis/trans isomers (50:50), as well as of a pure trans isomer of Zuclopenthixol.

Method:

A solution of ZU in cis conformation was mixed to a solution of ZU in trans conformation (1:1) to obtain ZU in a 50/50 cis/trans conformation and their respective effects on ErbB2 activation and ErbB2-dependent cell proliferation were analyzed as previously by dot blot analysis using an anti-phosphotyrosine antibody (clone 4G10) and by MTT assays in the ErbB2-overexpressing breast cancer cell line SKBR3, BT474, or HBMEC as a control.

Figure 9:
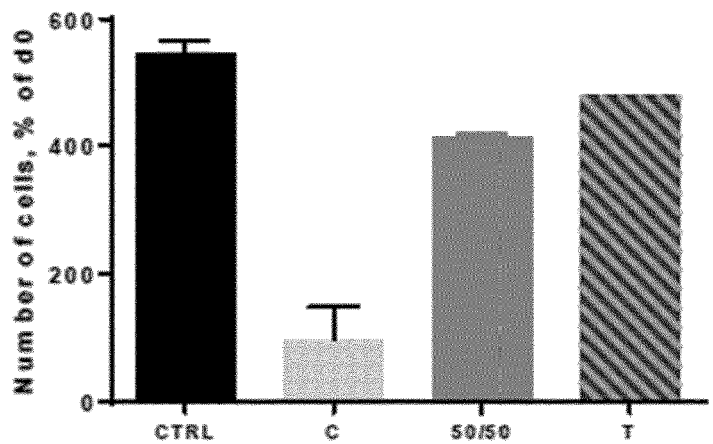
FIG. 9. represents the effect of compound ZU cis (C)/trans (T) conformation, or a mixture C/T (50/50) on the specific inhibition of the ErbB2-dependent cell proliferation of (A) SKBR3 and (B) BT474 and (C) HBMEC as a control measured by MTT assays.
Figure 9:
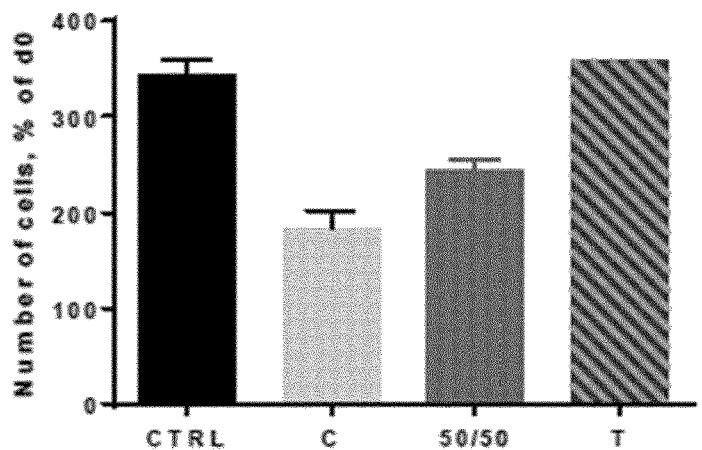
Figure 9:
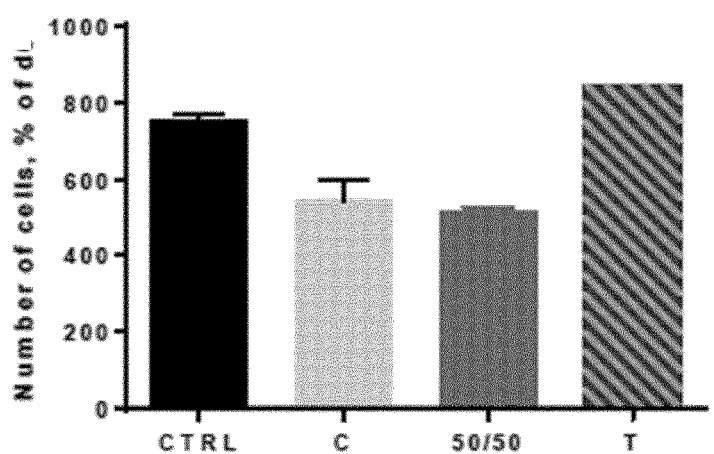

Results:

The results of these tests are indicated in FIGS. 9A to 9C.

Pure cis, or mix of cis/trans isomers of Zuclopenthixol all similarly inhibited ErbB2 activation in SKBR3. However, at 10 μM the trans isomer had no significant inhibitory effect on the proliferation of the SKBR3 and BT474 cell lines (FIG. 9B).

These results demonstrate that the cis conformation of Zuclopenthixol is particularly advantageous to ensure a specific inhibition of ErbB2.

Example 10: ZU Specifically Inhibits Overexpressed, Mutated or Truncated Forms of ErbB2

Method:

HBMECs cells were transfected with plasmids encoding WT, ΔEBM (a form of ErbB2 carrying mutations in the juxtamembrane domain and unable to bind to the Ezrin FERM domain), V659E or p95 ErbB2 and treated with 0, 5, 10 or 20 μM ZU for 24 h. ErbB2 activation was then analyzed by western blot analysis using a phospho-ErbB2-specific antibody (pY1248) and a tubulin antibody as a loading control. Histograms show optical density quantification.

Figure 10:
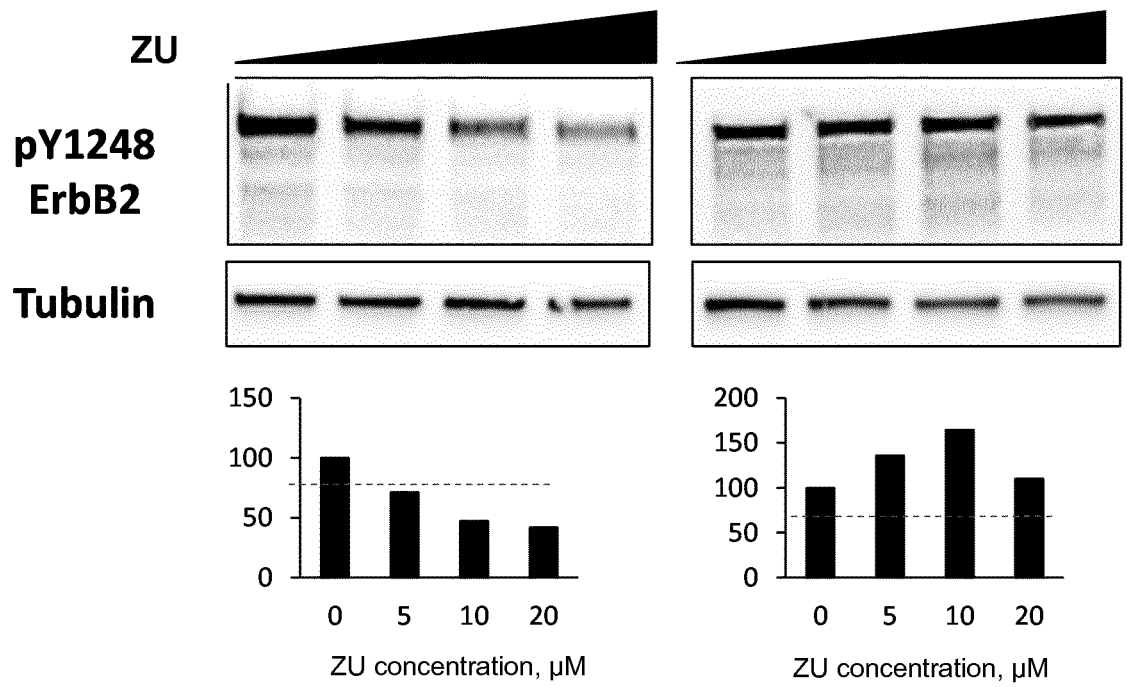
FIG. 10. represents the specific inhibition of overexpressed, mutated (V659E) or truncated (p95, DeltaEBM) forms of ErbB2 by compound ZU measured by western blot analysis of ErbB2 phosphorylation in transfected HBMECs cells. The upper line displays representative western-blots and the lower histograms displays their respective quantification for each ErbB2 form.
Figure 10:
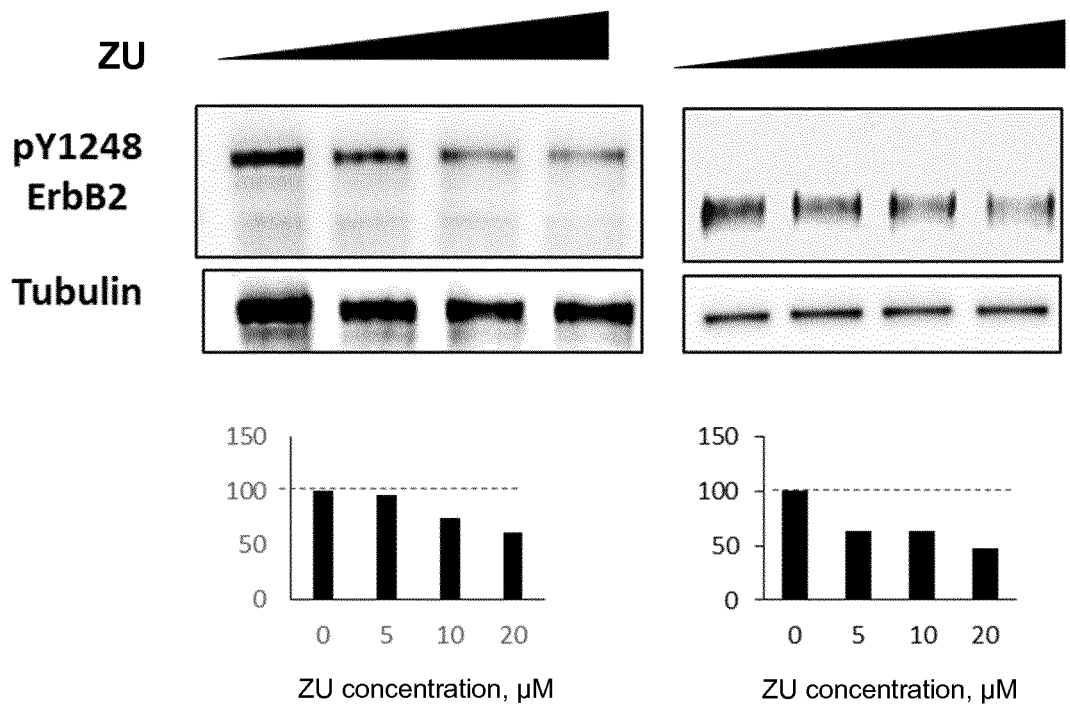

Results:

ZU decreased the activation of WT, V659E or p95 ErbB2 without any effect on ΔEBM ErbB2 mutant (FIG. 10).

These results demonstrate that ZU activity is mediated by the EBM motif in the juxtamembrane region of ErbB2, therefore confirming the molecular mechanism by which ZU inhibits ErbB2. Moreover, these results also demonstrate the activity of ZU on V659E and p95 ErbB2 that confer aggressiveness to the breast tumors and/or resistance to the actual treatments and therefore are associated with bad prognosis.

Example 11: ZU, EBa and their Derivatives do not Affect the Ligand-Dependent Activation of ErbB2

In physiological conditions, ErbB2 activation occurs in heterodimer with the other ErbB family members, such as the EGFR in response to EGF stimulation or ErbB3 in response to heregulin (HRG) stimulation. We therefore addressed whether ZU, EB1 and their derivatives also affected the ligand-dependent physiological ErbB2 activation.

Method:

16 h-starved HBMECs cells were pre-treated or not for 1 h or 24 h with ZU, EBa and their derivatives or AG1478 before EGF (50 ng/mL) or HRG1β (100 ng/mL) stimulation for 5 minutes. The activation of EGFR/ErBB2 or ErbB3/ErbB2 heterodimers-dependent signalling pathways was then analysed by western blot experiments using pAkt, Akt, pERK, ERK or 4G10 antibodies.

Figure 11A:
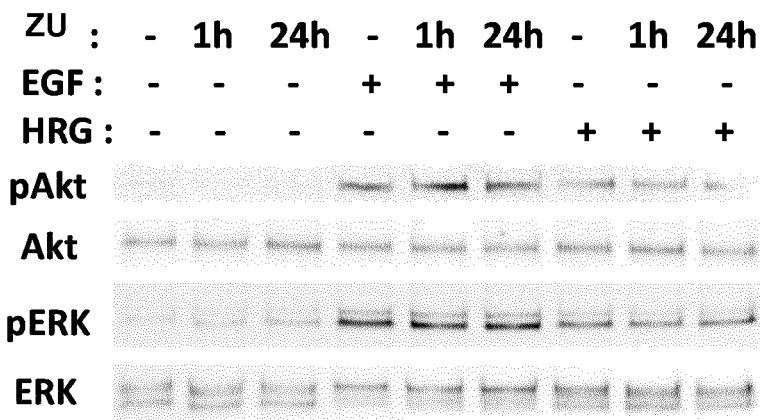
FIG. 11. represents the absence of inhibition of the ligand-dependent ErbB2 activation by compound ZU and compound EB1 measured by western blot analysis in HBMECs cells. Briefly, HBMECs cells were stimulated 5 min with EGF or HRG to induce heterodimeric activation of ErbB2 with EGFR or ErbB3 respectively in the absence or presence of (A) compound ZU, (B) compound EB1, for 1 h or 24 h. (C) As a control AG1478 strongly blocked the ligand-dependent ErbB2 activation.
Figure 11B:
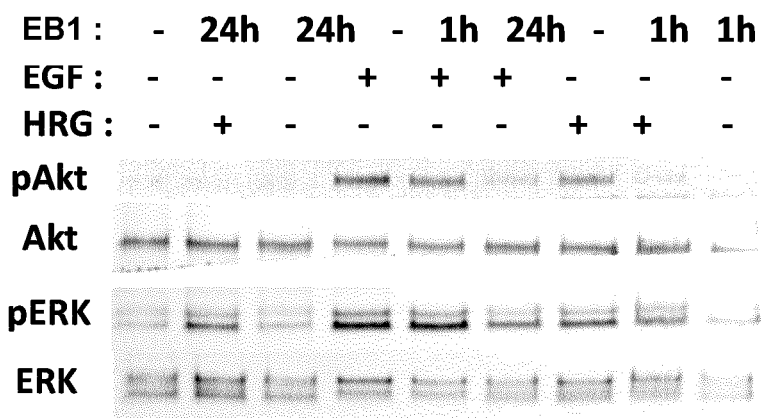
Figure 11C:
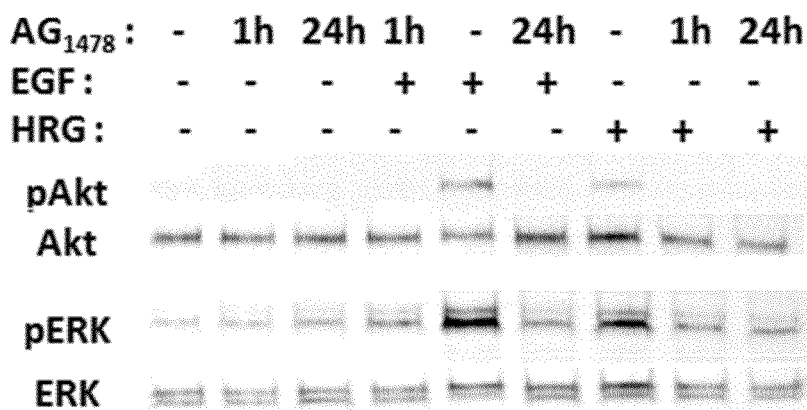

Results:

ZU, EBa and their derivatives did not block the ligand-dependent ErbB2 activation induced by EGF or HRG stimulation whereas AG1478 did (FIG. 11).

These results demonstrate that ZU and their derivatives specifically block the ligand-independent activation of ErbB2. Therefore they will not interfere with physiological ErbB2 activation.

Example 12: Inhibition of the Development In Vivo of Human Breast cancer BT474 Cells by EB1

We addressed the ability of EB1 to inhibit the development in vivo of human breast cancer BT474 cells orthotopically implanted in the mammary fat pad of immunodeficient NOG mice, as we did with ZU.

Method:
5.10$^6$ BT474 cells were implanted orthotopically in the mammary fat pad of NOD.Cg-Prkdc scid/J mice, in the presence of estradiol supplement. After 4 weeks, mice were injected with EB1 3 mg/kg (N=8), 5 mg/kg (N=6) or vehicle (N=8, 10% DMSO in PBS) twice a day for 5 days a week (2×D), during 2 weeks then once per day (1×D) during 3 days. Mice weight and tumor volume were measured 3 and 2 times a week respectively.
Results:
The result is shown in FIG. 12 (A-H). EB1 was able to decrease the tumor growth in vivo at 3 mg/kg but this was more significant at 5 mg/kg as assessed by tumor volume measurement as well as tumor weight. The treatment was well tolerated as shown by the body weight. As BT474 cells have a known trastuzumab-resistance status, EB1 can therefore overcome trastuzumab resistance.

Figure 12A:
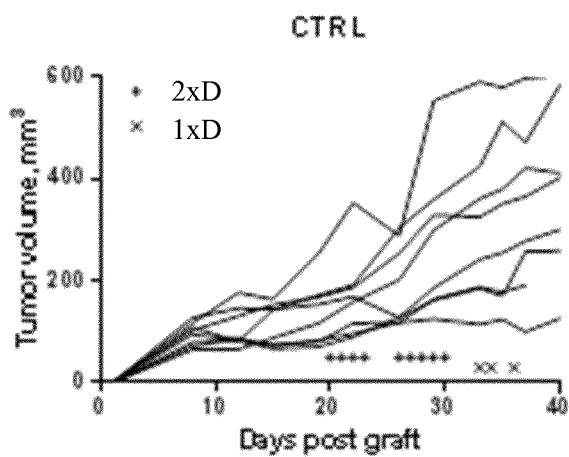
FIG. 12. represents the inhibition by compound EB1 of the rate of BT474 tumor proliferation in vivo in orthotopic xenografts. (A), (B) and (C) show the quantification of the tumor volume (mm$^3$) of each mouse injected twice a day (2×D) 5 days a week for two weeks then once a day (1×D) for 3 days a week with saline, 3 mg/kg and 5 mg/kg of EB1 respectively; while (D) and (E) show the normalized tumor volume (expressed as a % of tumor volume measured at day 19 (d19) post graft) of mice injected with saline and 3 mg/kg of EB1 and saline and 5 mg/kg of EB1 respectively (Point by point comparison with controls using the Dunnett's test: *P<0.05, **P<0.01). (F) displays pictures of tumors from each group. (G) and (H) display quantification of the tumor weight and body weight respectively.
Figure 12B:
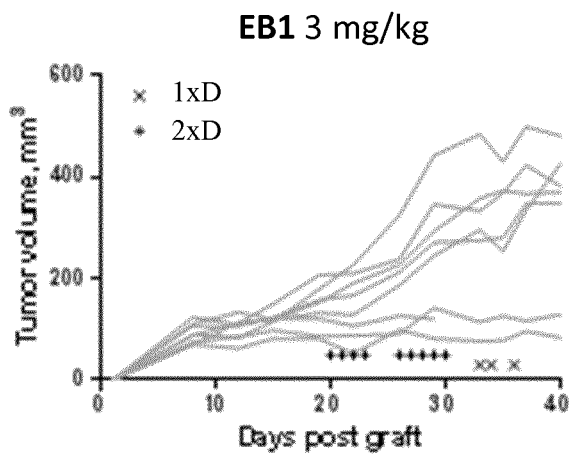
Figure 12C:
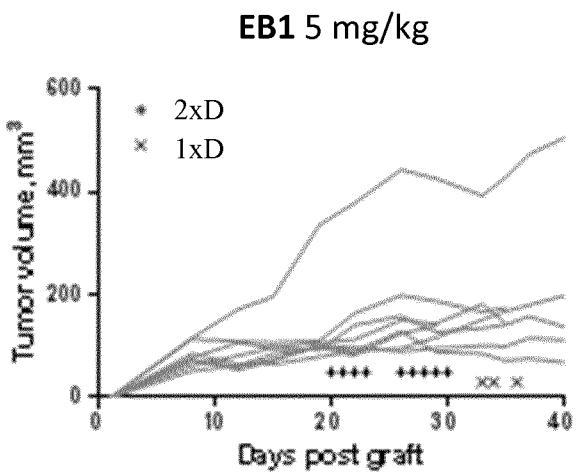
Figure 12D:
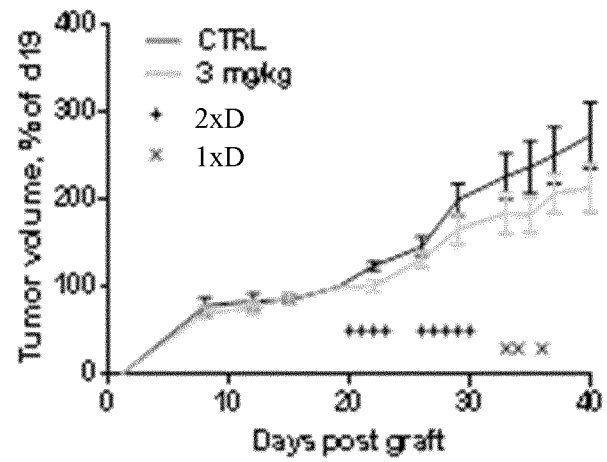
Figure 12E:
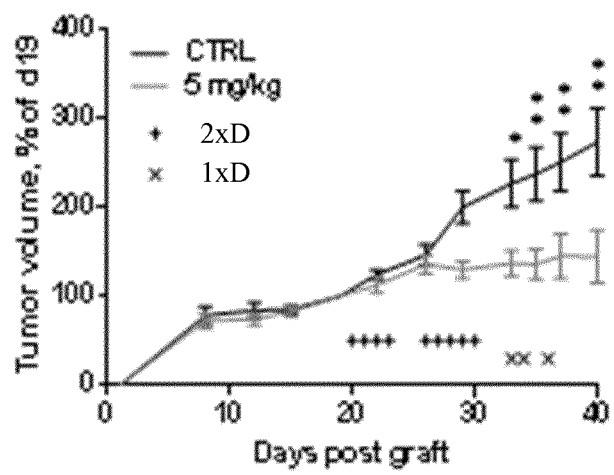
Figure 12F:
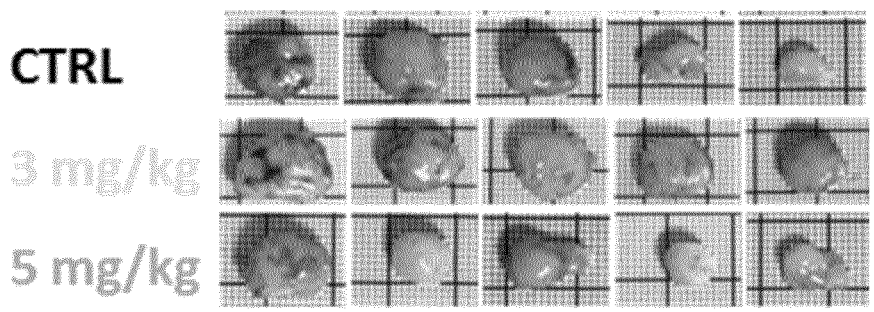
Figure 12G:
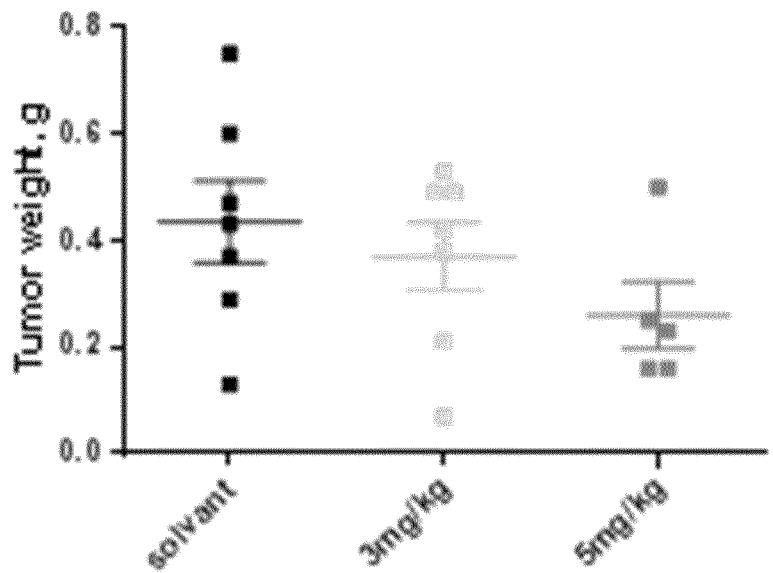
Figure 12H:
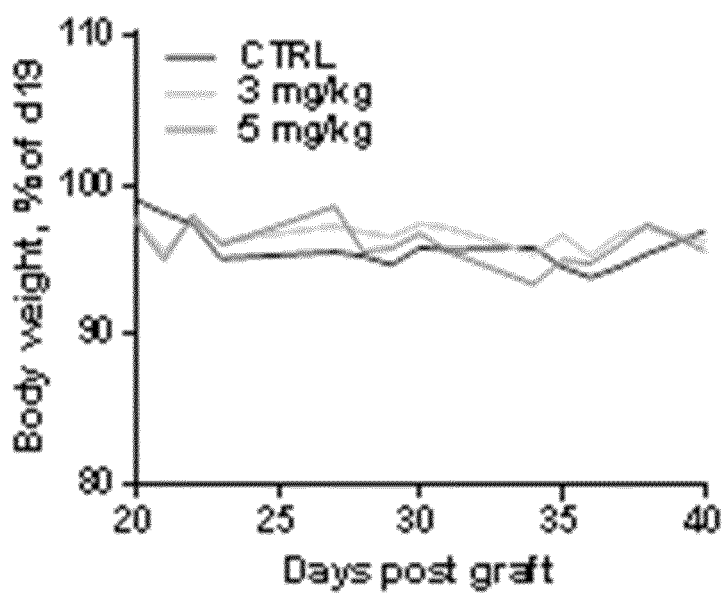

FIG. 12E: Two-way ANOVA: interaction between time and EB1 treatment $F(16,128)=2.797$, $P=0.0007$, P2 treatment effect $F(2,16)=3.196$, $P=0.068$, time effect $F(8,128)=23.69$, $P<0.0001$. Point by point comparison with controls using the Dunnett's test: *$P<0.05$, **$P<0.01$.

Example 13: Inhibition of ErbB2 Activation in N87 Gastric Carcinoma Cell Line

ErbB2 has also been shown to be overexpressed in other types of cancers such as ovarian, endometrial, salivary gland, gastric or colorectal cancers.

We therefore wanted to test the effect of ZU and EB1 to inhibit ErbB2 in other types of ErbB2-overexpressiong cancers. For this, we first used N87 a gastric carcinoma cell line overexpressing ErbB2 and analyzed the effect of ZU and EB1 on ErbB2 activation.
Method:
The phosphotyrosine content in the ErbB2-overexpressing gastric cancer cell line N87 was analyzed by dot blot using an anti-phosphotyrosine antibody (clone 4G10). As in these cells, ErbB2 is the main phosphorylated protein, decreased in total phosphotyrosine content mainly reflected inhibition of ErbB2 activity. As a control, the non-specific ErbB2 kinase inhibitor AG1478 was used. Quantifications show the result of two independent experiments.
Results:
The result is shown in FIG. 13 (A-C). ZU and EB1 were both able to potently decrease ErbB2 activation in N87 cell line.

Example 14: Inhibition of ErbB2-Dependent Proliferation of N87 Gastric Carcinoma Cell Line by ZU We then examined ZU ability to inhibit ErbB2-dependent N87 cell proliferation.
Method:
The ErbB2-overexpressing gastric cancer cell line N87 and MDAMB-231, a non ErbB2-overexpressing breast cancer cell line were treated with 3, 5 or 7 µM of ZU and cell proliferation was determined each day during 3 days using an MTT assay. Non treated cells were included as a negative control.
Results:
The result is shown in FIG. 14 (A-B). ZU 3, 5 and 7 µM induced a 35% decrease of the proliferation of N87 gastric cancer cell line at day 3 whereas there was no effect on MDAMB-231 control cell line.

Example 15: Inhibition of the Colony Formation of N87 in a Soft Agar Assay

To confirm the potent effect of ZU, we analyzed their efficiency to inhibit the colony formation of N87 cells in a soft agar assay.
Method:
A bottom layer of 0.8% agarose in DMEM supplemented with 20% SVF and penicillin/streptomycin was added to 24 well plates before seeding 15.10$^3$ N87 cells/well in a 0.6% agarose top layer. Cells were left untreated or treated with 5 or 10 µM ZU or 5 µM AG1478 (a non-specific ErbB2 kinase inhibitor) as a positive control. Treatments were renewed 3 times a week. After 6 weeks, the number of colonies and their size were quantified using image J software. The colony formation is illustrated for each condition. Data are presented as mean±SEM (One way ANOVA: $F(3, 6)=170.9$; Dunnett's Post Hoc Test ****$p<0.0001$).
Results:
The result is shown in FIG. 15 (A-B). ZU induced a 50% inhibition of N87 microcolony formation.

Example 16: Inhibition of ErbB2 Activation in SKOV3 Ovarian Carcinoma Cell Line

We then wanted to test the effect of ZU to inhibit ErbB2 in SKOV3, an ovarian carcinoma cell line overexpressing ErbB2.
Method:
The phosphotyrosine content in the ErbB2-overexpressing ovarian cancer cell line SKOV3 was analyzed by dot blot using an anti-phosphotyrosine antibody (clone 4G10). As in these cells, ErbB2 is the main phosphorylated protein, decreased in total phosphotyrosine content mainly reflected inhibition of ErbB2 activity. As a control, the non-specific ErbB2 kinase inhibitor AG1478 was used. Quantifications show the result of two independent experiments.
Results:
The result is shown in FIG. 16 (A-B). ZU potently decreases ErbB2 activation in SKOV3 cell line.

Example 17: Inhibition of ErbB2-Dependent Proliferation of SKOV3 Ovarian Carcinoma Cell Line by ZU As it was reported that SKOV3 exhibited a strong non ErbB2-dependent cell proliferation in the presence of serum, we decrease the serum content of the culture medium to 1% and examined ZU ability to inhibit ErbB2-dependent SKOV3 cell proliferation.
Method:
The ErbB2-overexpressing ovarian cancer cell line SKOV3 and MDAMB-231, a non ErbB2-overexpressing breast cancer cell line were treated with 3, 5 or 7 µM of ZU and cell proliferation was determined each day during 3 days using an MTT assay. Non treated cells were included as a negative control.
Results:
The result is shown in FIG. 17 (A-B). ZU 3, 5 and 7 µM induced a 50% decrease of the proliferation of SKOV3 ovarian carcinoma cell line at days 2 and 3 whereas there was no effect on MDAMB-231 control cell line.

Altogether these results show that ZU can actively block ErbB2 activation and ErbB2-dependent cell proliferation in the SKOV3 ovarian carcinoma cell line.

Example 18: Inhibition of the Colony Formation of SKOV3 in a Soft Agar Assay To confirm the potent effect of ZU, we analyzed their efficiency to inhibit the colony formation of SKOV3 cells in a soft agar assay.

Method:

A bottom layer of 0.8% agarose in DMEM supplemented with 2% SVF and penicillin/streptomycin was added to 24 well plates before seeding $15.10^3$ SKOV3 cells/well in a 0.6% agarose top layer. Cells were left untreated or treated with 5 or 10 µM ZU or 5 µM AG1478 (a non-specific ErbB2 kinase inhibitor) as a positive control. Treatments were renewed 3 times a week. After 6 weeks, the number of colonies and their size were quantified using image J software. The colony formation is illustrated for each condition. Data are presented as mean±SEM Results:

The result is shown in FIG. 18 (A-B). ZU totally inhibited the formation of SKOV3 microcolonies.

Altogether these results show that ZU and EB1 can actively block Erbb2 activation and ErbB2-dependent cell proliferation in other ErbB2-overexpressing cancers such as gastric or ovarian cancers.

Example 19: Inhibition of the Activation of Erbb2 Mutated in the Kinase Domain Activating mutations of ErbB2 located in its kinase domain have been reported in ErbB2-dependent cancers.

We therefore wanted to test the effect of ZU and EB1 to inhibit some of these mutated forms of ErbB2. We used ErbB2 carrying Val 777 to Leu mutation that was notably reported in cases of breast, colorectal and anal cancers as well as in neurofibroma. Of note, V777L mutated form was found as mediating resistance to trastuzumab in breast cancer. We also used ErbB2 carrying Val 842 to Ileu mutation that was reported in cases of colorectal, endometrial, gastroesophageal, ovarian and pancreatic cancers. We therefore analyzed their effect on V777L and V842I ErbB2 activation.

Method:

HBMECs cells were transfected with plasmids encoding WT, V777L or V842I and treated with 0, 5, 10 or 20 µM ZU or EB1 for 48 h. ErbB2 activation was then analyzed by western blot analysis using a phospho-ErbB2-specific antibody (pY1248) and a total ErbB2 antibody. Histograms show optical density quantification.

Results:

The result is shown in FIG. 19 (A-C). ZU and EB1 were both able to potently decrease ErbB2 WT, V777L and V842I activation.

Example 20: Inhibition of the V777L and V842I Erbb2-Dependent Cell Proliferation by ZU We then examined ZU ability to inhibit V777L and V842I ErbB2-dependent cell proliferation.

Method:

The WT, V777L or V842I ErbB2-transfected cells were treated with 5 or 10 µM of ZU and cell proliferation was determined each day during 3 days using an MTT assay. Non transfected cells were included as a negative control.

Results:

The result is shown in FIG. 20 (A-D). ZU 10 µM induced 50%, 35% and 65% decrease of the proliferation of WT, V777L and V842I transfected HBMEC at day 3, respectively, whereas there was no effect on non-transfected HBMECs cells.

Example 21: Inhibition of the V777L and V842I Erb2-Dependent Cell Proliferation by EB1

We then examined EB1 ability to inhibit V777L and V842I ErbB2-dependent cell proliferation.

Method:

The WT, V777L or V842I ErbB2-transfected cells were treated with 5 or 10 µM of EB1 and cell proliferation was determined each day during 3 days using an MTT assay. Non transfected cells were included as a negative control.

Results:

The result is shown in FIG. 21 (A-D). EB1 5 µM induced 60%, 70% and 55% decrease of the proliferation of WT, V777L and V842I transfected HBMEC at day 3, respectively. This effect reached 95%, 85% and 90% inhibition at 10 µM whereas there was no effect on non-transfected HBMECs cells.

Altogether these results show that ZU and EB1 can actively block ErbB2 activation and ErbB2-dependent cell proliferation of V777L and V842I mutated forms of ErbB2 which are notably found in breast, colorectal, anal cancers, neurofibroma, endometrial, gastroesophageal, ovarian and pancreatic cancers. Interestingly, as mentioned above, V777L mutation was found as mediating resistance to trastuzumab in breast cancer.

III—Conclusion

Altogether, these data unraveled the identification of two novel families of molecules that selectively inhibit HER2 activation by a mechanism which differs from the one of trastuzumab and lapatinib: i.e. binding to the juxtamembrane domain of ErbB2.

In conclusion, we identified 2 families of compounds exhibiting key features:

Direct interaction with the juxtamembrane domain of ErbB2

Specific inhibition of ErbB2 phosphorylation

Specific inhibition of ErbB2-dependent cell proliferation, both in vitro and in vivo on the development of orthotopic tumors.

Of note this inhibition is observed in vitro for compound concentrations below 15 µM above which nonspecific toxicity is noticed whatever the ErbB2 status of the cells.

These compounds inhibit ErbB2 activation by a mechanism which differs from the one of trastuzumab and lapatinib and efficiently blocks the activation of trastuzumab-resistant cell lines.

These novel molecules provide alternative treatment to ErbB2-dependent cancers. These molecules can be used as well in combinatory treatments and also to maximize the clinical benefit from immune therapies directed to extracellular part of ErbB2 (e.g. trastuzumab) or from inhibitor of tyrosine kinase based therapies (e.g. lapatinib), consequently allowing reducing the doses of the drug required and their associated toxicity and preventing or delaying resistance and metastases spreading.

The invention claimed is:

1. A method of inhibiting ErbB2 activation in an ErbB2 dependent cancer patient, the method comprising:
   selecting an ErbB2 dependent cancer patient that overexpresses ErbB2; and
   administering to the ErbB2 dependent cancer patient an effective amount of a compound of formula (I), or a pharmaceutically acceptable salt and/or solvate thereof for inhibiting ErbB2 activation;
   wherein compound (I) has the general formula:

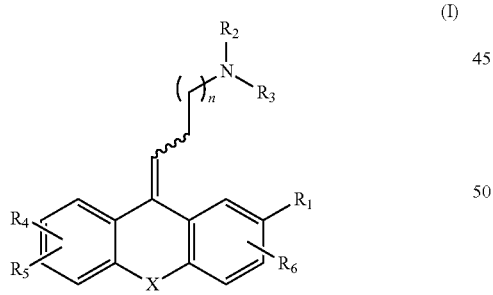

(I)

wherein:
the symbol ⌇ represents a bond in cis or trans configuration;
X is a sulfur atom;
$R_1$ is hydrogen atom, halo, —CN, —NO$_2$, —NO, —CHO, —NR$_7$R$_8$, —CO$_2$R$_9$, —SO$_2$R$_{10}$, —SO$_2$NR$_{11}$R$_{12}$, —OR$_{13}$, —COR$_{14}$, —SR$_{15}$, —CONR$_{16}$R$_{17}$, —SO$_2$(O)R$_{18}$ or a group selected from saturated (C$_1$-C$_6$)alkyl, unsaturated (C$_1$-C$_6$) alkyl and aryl, said group being optionally substituted with one or several groups selected from halo, —CF$_3$, —CN and —SO$_2$NR$_{19}$R$_{20}$;

$R_2$ and $R_3$ form together with the nitrogen atom to which they are chemically linked a piperazinyl group substituted with one or several groups selected from halo, —CO$_2$R$_{21}$ and a (C$_1$-C$_6$)alkyl group, the (C$_1$-C$_6$)alkyl group being optionally substituted with one or several groups selected from halo, —OR$_{22}$, —SR$_{23}$, —S(O)R$_{24}$, —SO$_2$R$_{25}$, —SO$_2$NR$_{26}$R$_{27}$, —OC(O)R$_{28}$, —NR$_{29}$COR$_{30}$, —NR$_{31}$CONR$_{32}$R$_{33}$, —NR$_{34}$C(O)OR$_{35}$, —CO$_2$R$_{36}$, —CONR$_{37}$R$_{38}$, —OCO$_2$R$_{39}$, —OCONR$_{40}$R$_{41}$, —COR$_{42}$, —NO$_2$, CF$_3$, and —CN;

$R_4$, $R_5$ and $R_6$ are, independently of one another, hydrogen atom, halo, —CN, —NO$_2$, —NO, —CHO, —NR$_{43}$R$_{44}$, —CO$_2$R$_{45}$, —S(O)R$_{46}$, —SO$_2$R$_{47}$, —SO$_2$NR$_{48}$R$_{49}$, —OCOR$_{50}$, —NR$_{51}$COR$_{52}$, —NR$_{53}$CO(O)R$_{54}$, —NR$_{55}$CONR$_{56}$R$_{57}$, —CO$_2$R$_{58}$, —OR$_{59}$, —COR$_{60}$, —SR$_{61}$, —CONR$_{62}$R$_{63}$, —OCONR$_{64}$R$_{65}$, —SO$_2$(O)R$_{66}$, or a group selected from saturated (C$_1$-C$_6$)alkyl, unsaturated (C$_1$-C$_6$) alkyl and aryl, said group being optionally substituted with one or several groups selected from halo, —CF$_3$, —CN, and —SO$_2$NR$_{67}$R$_{68}$;

$R_7$ to $R_{68}$ are, independently of one another, a hydrogen atom or a (C$_1$-C$_{10}$)alkyl, aryl or aryl(C$_1$-C$_6$)alkyl group, said group being optionally substituted with one or several groups selected from halo, —OH, —CF$_3$, —CN and SO$_2$NR$_{69}$R$_{70}$; with the proviso that $R_{21}$ is not an hydrogen atom;

$R_{69}$ and $R_{70}$ are independently of one another, a hydrogen atom or a (C$_1$-C$_{10}$)alkyl, aryl or aryl(C$_1$-C$_6$)alkyl group; and n is an integer selected from 1 to 6.

2. The method according to claim 1, wherein $R_1$ is hydrogen atom, halo, —CN, —$NO_2$, —NO, —CHO, —$NR_7R_8$, —$CO_2R_9$, —$SO_2R_{10}$, —$SO_2NR_{11}R_{12}$, —$COR_{14}$, —$CONR_{16}R_{17}$, —$SO_2(O)R_{18}$ or a group selected from saturated ($C_1$-$C_6$)alkyl, unsaturated ($C_1$-$C_6$)alkyl and aryl, said group being optionally substituted with one or several groups selected from halo, —$CF_3$, —CN and —$SO_2NR_{19}R_{20}$; $R_7$ to $R_{12}$, $R_{14}$ and $R_{16}$ to $R_{20}$ being as defined in claim 1.

3. The method according to claim 1, wherein $R_1$ is hydrogen atom, halo, —CN, —$SO_2NR_{11}R_{12}$ or —$CF_3$; $R_{11}$ and $R_{12}$ being as defined in claim 1.

4. The method according to claim 1, wherein $R_2$ and $R_3$ form together with the nitrogen atom to which they are chemically linked a piperazinyl group, substituted with one or several ($C_1$-$C_6$)alkyl group optionally substituted with one or several groups selected from —$OR_{22}$, —$SR_{23}$, —$S(O)R_{24}$, —$SO_2R_{25}$, —$SO_2NR_{26}R_{27}$, —$OC(O)R_{28}$, —$NR_{29}COR_{30}$, —$NR_{31}CONR_{32}R_{33}$, —$NR_{34}C(O)OR_{35}$, —$CO_2R_{36}$, —$CONR_{37}R_{38}$, —$OCO_2R_{39}$, —$OCONR_{40}R_{41}$, —$COR_{42}$, —$NO_2$ and —CN; $R_{22}$ to $R_{42}$ being as defined in claim 1.

5. The method according to claim 1, wherein $R_2$ and $R_3$ form together with the nitrogen atom to which they are chemically linked a piperazinyl group, substituted with one ($C_1$-$C_6$)alkyl group optionally substituted with one or several groups selected from —$OR_{22}$, —$SR_{23}$, —$S(O)R_{24}$, —$SO_2R_{25}$, —$SO_2NR_{26}R_{27}$, —$OC(O)R_{28}$, —$OCO_2R_{39}$ and —$COR_{42}$; and wherein $R_{22}$ to $R_{28}$, $R_{39}$ and $R_{42}$ are, independently of one another, a hydrogen atom or a ($C_1$-$C_{10}$) alkyl group.

6. The method according to claim 1, wherein $R_2$ and $R_3$ form together with the nitrogen atom to which they are chemically linked a piperazinyl group, substituted with one ($C_1$-$C_6$)alkyl group optionally substituted with one group selected from —$OR_{22}$ and —$OC(O)R_{28}$;

and wherein $R_{22}$, $R_{28}$, and $R_{31}$ to $R_{33}$ are, independently of one another, a hydrogen atom or a ($C_1$-$C_6$)alkyl group.

7. The method according to claim 1, wherein $R_4$, $R_5$ and $R_6$ are, independently of one another, hydrogen atom, halo or ($C_1$-$C_6$)alkyl.

8. The method according to claim 1, wherein the compound is of following general formula (Ia):

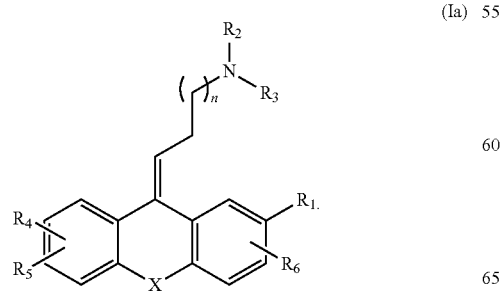

(Ia)

9. The method according to claim 1, wherein said compound is selected from the following compounds:

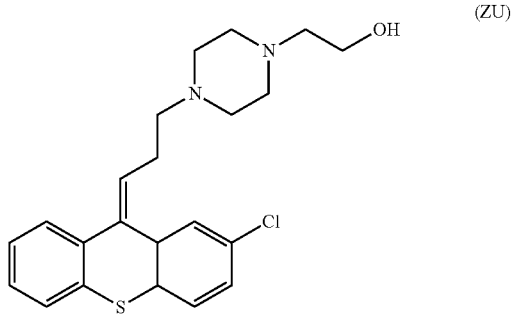

(ZU)

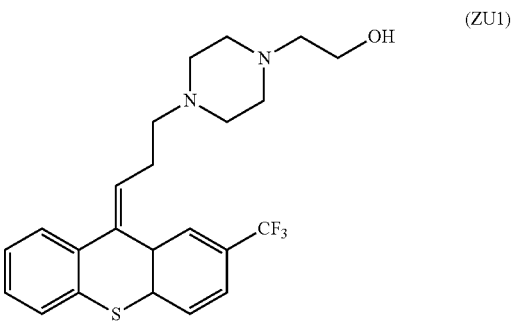

(ZU1)

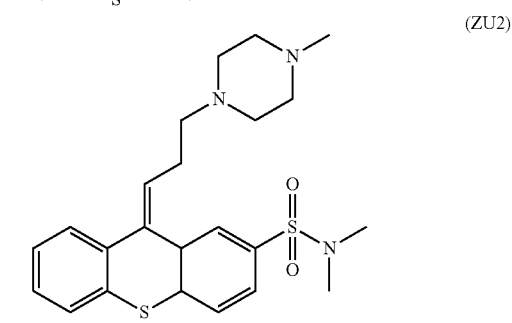

(ZU2)

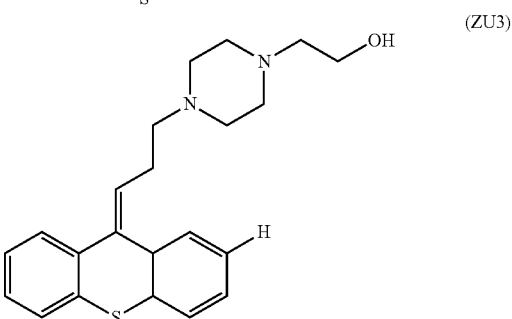

(ZU3)

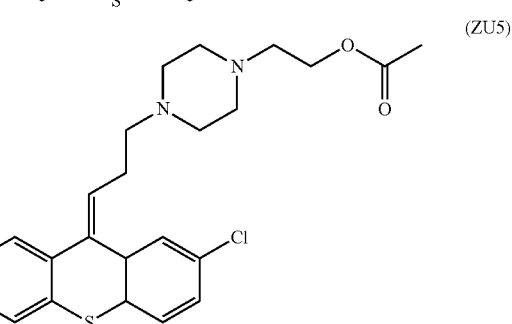

(ZU5)

and pharmaceutically acceptable salt and/or solvate thereof.

10. The method according to claim 1, wherein the ErbB2 cancer patient that overexpresses ErbB2 is a patient with metastases.

11. The method according to claim 1, wherein said ErbB2 dependent cancer is lung cancer, ovarian cancer, stomach cancer, bladder cancer, uterine cancer, pancreas cancer, liver cancer, kidney cancer, gastroeosophageal cancer, gastric cancer, colorectal cancer, female genital tract cancer, endometrial cancer, anal cancer, breast cancer or neurofibroma.

12. The method according to claim 11, wherein said ErbB2 dependent cancer is ovarian cancer, pancreas cancer, gastroeosophageal cancer, gastric cancer, colorectal cancer, endometrial cancer, anal cancer or neurofibroma.

13. The method according to claim 11, wherein said ErbB2 dependent cancer is ovarian cancer, gastric cancer or breast cancer.

14. The method according to claim 3, wherein halo is Cl or F.

* * * * *

SEQUENCE LISTING

```
<160> NUMBER OF SEQ ID NOS: 2

<210> SEQ ID NO 1
<211> LENGTH: 18
<212> TYPE: PRT
<213> ORGANISM: Artificial Sequence
<220> FEATURE:
<223> OTHER INFORMATION: ErbB2 peptide encoding the Ezrin binding motif

<400> SEQUENCE: 1

Ile Leu Ile Lys Arg Arg Gln Gln Lys Ile Arg Lys Tyr Thr Met Arg
1               5                   10                  15

Arg Leu

<210> SEQ ID NO 2
<211> LENGTH: 17
<212> TYPE: PRT
<213> ORGANISM: Artificial Sequence
<220> FEATURE:
<223> OTHER INFORMATION: Juxtamembrane region of CD44

<400> SEQUENCE: 2

Asn Ser Arg Arg Arg Cys Gly Gln Lys Lys Lys Leu Val Ile Asn Ser
1               5                   10                  15

Gly
```